(12) United States Patent
Pyzocha et al.

(10) Patent No.: US 12,195,772 B2
(45) Date of Patent: Jan. 14, 2025

(54) RNA-GUIDED NUCLEASES AND DNA BINDING PROTEINS

(71) Applicant: INARI AGRICULTURE TECHNOLOGY, INC., Cambridge, MA (US)

(72) Inventors: Neena Kenton Pyzocha, New Boston, MA (US); Adam Patrick Joyce, Stow, MA (US); Karl Anton Grothe Kremling, Somerville, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 294 days.

(21) Appl. No.: 17/753,315

(22) PCT Filed: Aug. 28, 2020

(86) PCT No.: PCT/US2020/048456
§ 371 (c)(1),
(2) Date: Feb. 28, 2022

(87) PCT Pub. No.: WO2021/041846
PCT Pub. Date: Mar. 4, 2021

(65) Prior Publication Data
US 2022/0340890 A1 Oct. 27, 2022

Related U.S. Application Data

(60) Provisional application No. 62/893,939, filed on Aug. 30, 2019, provisional application No. 62/893,937, filed on Aug. 30, 2019, provisional application No. 62/893,844, filed on Aug. 30, 2019, provisional application No. 62/893,846, filed on Aug. 30, 2019, provisional application No. 62/893,935, filed on Aug. 30, 2019, provisional application No. 62/893,928, filed on Aug. 30, 2019, provisional application No. 62/893,932, filed on Aug. 30, 2019, provisional application No. 62/893,845, filed on Aug. 30, 2019, provisional application No. 62/893,925, filed on Aug. 30, 2019, provisional application No. 62/893,936, filed on Aug. 30, 2019.

(51) Int. Cl.
C12N 15/82 (2006.01)
C12N 9/22 (2006.01)
C12N 15/11 (2006.01)
C12N 15/62 (2006.01)

(52) U.S. Cl.
CPC .............. *C12N 9/22* (2013.01); *C12N 15/11* (2013.01); *C12N 15/62* (2013.01); *C12N 15/8213* (2013.01); *C12N 15/8242* (2013.01); *C07K 2319/00* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 11,041,172 B2 | 6/2021 | Cermak |
| 11,407,995 B1 | 8/2022 | Pyzocha et al. |
| 11,459,551 B1 | 10/2022 | Joyce et al. |
| 11,479,792 B2 | 10/2022 | Joyce et al. |
| 2005/0255487 A1 | 11/2005 | Khvorova et al. |
| 2015/0232883 A1 | 8/2015 | Dahlman et al. |
| 2019/0233814 A1 | 8/2019 | Zhang et al. |
| 2019/0241954 A1 | 8/2019 | Doudna et al. |
| 2021/0166783 A1 | 6/2021 | Shmakov et al. |
| 2021/0388333 A1 | 12/2021 | Pyzocha et al. |

FOREIGN PATENT DOCUMENTS

WO WO-2018035250 A1 * 2/2018 ........... C07K 14/195

OTHER PUBLICATIONS

International Search Report and Written Opinion in PCT/US2020/048456, mailed on Jan. 29, 2021, 12 pages.

* cited by examiner

*Primary Examiner* — Matthew R Keogh
(74) *Attorney, Agent, or Firm* — McKee, Voorhees & Sease, PLC

(57) ABSTRACT

Compositions and methods related to Cas proteins, nucleic acids encoding the Cas proteins, and modified host cells comprising the Cas proteins and/or encoding nucleic acids are disclosed. Cas proteins are useful in a variety of applications. Cas proteins bind guide RNAs that in turn provide functional specificity to the Cas proteins, nucleic acids encoding the Cas guide RNAs, and modified host cells comprising the Cas guide RNAs and/or encoding nucleic acids. The Cas polypeptides and corresponding guide RNAs can be used in a variety of applications.

20 Claims, No Drawings
Specification includes a Sequence Listing.

RNA-GUIDED NUCLEASES AND DNA BINDING PROTEINS

CROSS-REFERENCE TO RELATED APPLICATIONS

This application is a PCT International Application which claims the benefit of U.S. Provisional Application Ser. No. 62/893,844 filed Aug. 30, 2019, U.S. Provisional Application Ser. No. 62/893,925 filed Aug. 30, 2019, U.S. Provisional Application Ser. No. 62/893,928 filed Aug. 30, 2019, U.S. Provisional Application Ser. No. 62/893,932 filed Aug. 30, 2019, U.S. Provisional Application Ser. No. 62/893,935 filed Aug. 30, 2019, U.S. Provisional Application Ser. No. 62/893,936 filed Aug. 30, 2019, U.S. Provisional Application Ser. No. 62/893,937 filed Aug. 30, 2019, U.S. Provisional Application Ser. No. 62/893,845 filed Aug. 30, 2019, U.S. Provisional Application Ser. No. 62/893,846 filed Aug. 30, 2019, U.S. Provisional Application Ser. No. 62/893,939 filed Aug. 30, 2019, all of which are incorporated herein by reference in their entireties.

REFERENCE TO SEQUENCE LISTING SUBMITTED ELECTRONICALLY

The content of the electronically submitted sequence listing in ASCII text file 63200_198989.ST25.txt (Size: 133,295 bytes and Date of Creation: Aug. 26, 2020), filed with the application is incorporated herein by reference in its entirety.

FIELD

The invention is generally related to CRISPR (clustered regularly interspaced short palindromic repeat) effector systems.

BACKGROUND

The CRISPR/Cas system of bacterial acquired immunity against phages and viruses has been adapted into potent new technologies for genomic modifications, as well as other research tools. A few Class 2 nucleases have been intensively used and characterized, yet a need remains for alternative nucleases with different properties that may provide optimal performance or options in a variety genome modification or diagnostic applications.

SUMMARY

The present disclosure provides RNA-guided endonuclease polypeptides and RNA-guided DNA binding proteins, referred to herein as "CasMG1" polypeptides (also referred to as "CasMG1 proteins"); nucleic acids encoding the CasMG1 polypeptides; and modified host cells comprising the CasMG1 polypeptides and/or nucleic acids encoding same. CasMG1 polypeptides are useful in a variety of applications, which are provided.

The present disclosure provides guide RNAs (referred to herein as "CasMG1 guide RNAs") that bind to and provide sequence specificity to the CasMG1 proteins; nucleic acids encoding the CasMG1 guide RNAs; and modified host cells comprising the CasMG1 guide RNAs and/or nucleic acids encoding same. CasMG1 guide RNAs are useful in a variety of applications, which are provided.

The present disclosure provides RNA-guided endonuclease polypeptides and RNA-guided DNA binding proteins, referred to herein as "CasMG2" polypeptides (also referred to as "CasMG2 proteins"); nucleic acids encoding the CasMG2 polypeptides; and modified host cells comprising the CasMG2 polypeptides and/or nucleic acids encoding same. CasMG2 polypeptides are useful in a variety of applications, which are provided.

The present disclosure provides guide RNAs (referred to herein as "CasMG2 guide RNAs") that bind to and provide sequence specificity to the CasMG2 proteins; nucleic acids encoding the CasMG2 guide RNAs; and modified host cells comprising the CasMG2 guide RNAs and/or nucleic acids encoding same. CasMG2 guide RNAs are useful in a variety of applications, which are provided.

The present disclosure provides RNA-guided endonuclease polypeptides and RNA-guided DNA binding proteins, referred to herein as "CasMG3" polypeptides (also referred to as "CasMG3 proteins"); nucleic acids encoding the CasMG3 polypeptides; and modified host cells comprising the CasMG3 polypeptides and/or nucleic acids encoding same. CasMG3 polypeptides are useful in a variety of applications, which are provided.

The present disclosure provides guide RNAs (referred to herein as "CasMG3 guide RNAs") that bind to and provide sequence specificity to the CasMG3 proteins; nucleic acids encoding the CasMG3 guide RNAs; and modified host cells comprising the CasMG3 guide RNAs and/or nucleic acids encoding same. CasMG3 guide RNAs are useful in a variety of applications, which are provided.

The present disclosure provides RNA-guided endonuclease polypeptides and RNA-guided DNA binding proteins, referred to herein as "CasMG4" polypeptides (also referred to as "CasMG4 proteins"); nucleic acids encoding the CasMG4 polypeptides; and modified host cells comprising the CasMG4 polypeptides and/or nucleic acids encoding same. CasMG4 polypeptides are useful in a variety of applications, which are provided.

The present disclosure provides guide RNAs (referred to herein as "CasMG4 guide RNAs") that bind to and provide sequence specificity to the CasMG4 proteins; nucleic acids encoding the CasMG4 guide RNAs; and modified host cells comprising the CasMG4 guide RNAs and/or nucleic acids encoding same. CasMG4 guide RNAs are useful in a variety of applications, which are provided.

The present disclosure provides RNA-guided endonuclease polypeptides and RNA-guided DNA binding proteins, referred to herein as "CasMG5" polypeptides (also referred to as "CasMG5 proteins"); nucleic acids encoding the CasMG5 polypeptides; and modified host cells comprising the CasMG5 polypeptides and/or nucleic acids encoding same. CasMG5 polypeptides are useful in a variety of applications, which are provided.

The present disclosure provides guide RNAs (referred to herein as "CasMG5 guide RNAs") that bind to and provide sequence specificity to the CasMG5 proteins; nucleic acids encoding the CasMG5 guide RNAs; and modified host cells comprising the CasMG5 guide RNAs and/or nucleic acids encoding same. CasMG5 guide RNAs are useful in a variety of applications, which are provided.

The present disclosure provides RNA-guided endonuclease polypeptides and RNA-guided DNA binding proteins, referred to herein as "CasMG6" polypeptides (also referred to as "CasMG6 proteins"); nucleic acids encoding the CasMG6 polypeptides; and modified host cells comprising the CasMG6 polypeptides and/or nucleic acids encoding same. CasMG6 polypeptides are useful in a variety of applications, which are provided.

The present disclosure provides guide RNAs (referred to herein as "CasMG6 guide RNAs") that bind to and provide sequence specificity to the CasMG6 proteins; nucleic acids encoding the CasMG6 guide RNAs; and modified host cells comprising the CasMG6 guide RNAs and/or nucleic acids encoding same. CasMG6 guide RNAs are useful in a variety of applications, which are provided.

The present disclosure provides RNA-guided endonuclease polypeptides and RNA-guided DNA binding proteins, referred to herein as "CasMG7" polypeptides (also referred to as "CasMG7 proteins"); nucleic acids encoding the CasMG7 polypeptides; and modified host cells comprising the CasMG7 polypeptides and/or nucleic acids encoding same. CasMG7 polypeptides are useful in a variety of applications, which are provided.

The present disclosure provides guide RNAs (referred to herein as "CasMG7 guide RNAs") that bind to and provide sequence specificity to the CasMG7 proteins; nucleic acids encoding the CasMG7 guide RNAs; and modified host cells comprising the CasMG7 guide RNAs and/or nucleic acids encoding same. CasMG7 guide RNAs are useful in a variety of applications, which are provided.

The present disclosure provides RNA-guided endonuclease polypeptides and RNA-guided DNA binding proteins, referred to herein as "CasMG8" polypeptides (also referred to as "CasMG8 proteins"); nucleic acids encoding the CasMG8 polypeptides; and modified host cells comprising the CasMG8 polypeptides and/or nucleic acids encoding same. CasMG8 polypeptides are useful in a variety of applications, which are provided.

The present disclosure provides guide RNAs (referred to herein as "CasMG8 guide RNAs") that bind to and provide sequence specificity to the CasMG8 proteins; nucleic acids encoding the CasMG8 guide RNAs; and modified host cells comprising the CasMG8 guide RNAs and/or nucleic acids encoding same. CasMG8 guide RNAs are useful in a variety of applications, which are provided.

The present disclosure provides RNA-guided endonuclease polypeptides and RNA-guided DNA binding proteins, referred to herein as "CasMG9" polypeptides (also referred to as "CasMG9 proteins"); nucleic acids encoding the CasMG9 polypeptides; and modified host cells comprising the CasMG9 polypeptides and/or nucleic acids encoding same. CasMG9 polypeptides are useful in a variety of applications, which are provided.

The present disclosure provides guide RNAs (referred to herein as "CasMG9 guide RNAs") that bind to and provide sequence specificity to the CasMG9 proteins; nucleic acids encoding the CasMG9 guide RNAs; and modified host cells comprising the CasMG9 guide RNAs and/or nucleic acids encoding same. CasMG9 guide RNAs are useful in a variety of applications, which are provided.

The present disclosure provides RNA-guided endonuclease polypeptides and RNA-guided DNA binding proteins, referred to herein as "CasMG10" polypeptides (also referred to as "CasMG10 proteins"); nucleic acids encoding the CasMG10 polypeptides; and modified host cells comprising the CasMG10 polypeptides and/or nucleic acids encoding same. CasMG10 polypeptides are useful in a variety of applications, which are provided.

The present disclosure provides guide RNAs (referred to herein as "CasMG10 guide RNAs") that bind to and provide sequence specificity to the CasMG10 proteins; nucleic acids encoding the CasMG10 guide RNAs; and modified host cells comprising the CasMG10 guide RNAs and/or nucleic acids encoding same. CasMG10 guide RNAs are useful in a variety of applications, which are provided.

DETAILED DESCRIPTION

Definitions

The term "and/or" where used herein is to be taken as specific disclosure of each of the two or more specified features or components with or without the other specified features. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "DNA donor template" refers to a DNA molecule having homology to the target editing site, DNA donor template molecules can be used to edit a target editing site in a genome by homology-directed repair.

"Heterologous," as used herein, means a nucleotide or polypeptide sequence that is not found in the native nucleic acid or protein, respectively. For example, relative to a CasMG polypeptide (e.g., any of CasMG1-CasMG10), a heterologous polypeptide comprises an amino acid sequence from a protein other than the same CasMG polypeptide. In some cases, a portion of a CasMG protein from one species is fused to a portion of a Cas protein from a different species. The Cas sequence from each species could therefore be considered to be heterologous relative to one another. As another example, a CasMG protein (e.g., a dCasMG protein) can be fused to an active domain from a non-CasMG protein (e.g., a histone deacetylase), and the sequence of the active domain could be considered a heterologous polypeptide (it is heterologous to the CasMG protein).

The phrase "CasMG fusion polypeptide" as used herein refers to a polypeptide comprising a CasMG polypeptide (e.g., any of CasMG1-CasMG10) fused to a heterologous polypeptide. In some cases, the CasMG polypeptide is operably linked to the heterologous polypeptide in the CasMG fusion polypeptide.

As used herein, the terms "correspond," "corresponding," and the like, when used in the context of an amino acid position, mutation, and/or substitution in any given CasMG polypeptide with respect to a reference CasMG polypeptide sequence (e.g, the reference polypeptide sequence for CasMG1 is SEQ ID NO: 1; for CasMG2 is SEQ ID NO: 59; for CasMG3 is SEQ ID NO: 66; for CasMG4 is SEQ ID NO: 73; for CasMG5 is SEQ ID NO: 80; for CasMG6 is SEQ ID NO: 87; for CasMG7 is SEQ ID NO: 94; for CasMG8 is SEQ ID NO: 101; for CasMG9 is SEQ ID NO: 108; and for CasMG10 is SEQ ID NO: 115), all refer to the position, mutation, and/or substitution of the amino acid residue in the given CasMG polypeptide that has identity or similarity to the amino acid residue in the reference CasMG polypeptide sequence when the given CasMG polypeptide is aligned to the reference CasMG polypeptide sequence using a pairwise alignment algorithm (e.g, CLUSTAL O 1.2.4 with default parameters).

As used herein, the terms "include," "includes," and "including" are to be construed as at least having the features to which they refer while not excluding any additional unspecified features.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues: immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally-occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally-occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (e.g., in vitro, ex vivo, or in vivo). A general discussion of these methods can be found in Ausubel, et al. Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multi-cellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine: a group of amino acids having aliphatic-hydroxyl side chains consists of serine and threonine: a group of amino acids having amide-containing side chains consists of asparagine and glutamine: a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), Mol. Biol. 215:403-10. Another alignment algorithm is FASTA, available in the Genetics Computing Group (GCG) package, from Madison, Wisconsin. USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle. Academic Press, Inc., a division of Harcourt Brace & Co., San Diego. California. USA. Of particular interest are alignment programs that permit gaps in the sequence. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences. See/. Mol. Biol. 48:443-453 (1970)).

As used herein, the terms "treatment," "treating," and the like, refer to obtaining a desired trait, pharmacologic and/or physiologic effect. The effect can be to confer a desired trait (e.g., improved yield, resistance to insects, fungi, bacterial pathogens, and/or nematodes, herbicide tolerance, abiotic stress tolerance (e.g., drought, cold, salt, and/or heat tolerance), protein quantity and/or quality, starch quantity and/or quality, lipid quantity and/or quality, secondary metabolite quantity and/or quality, and the like, all in comparison to a control plant that lacks the modification. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a plant or mammal, e.g., in a human, and includes: (a) preventing the disease from occurring in a subject which may be predisposed to the disease but has not yet been diagnosed as having it: (b) inhibiting the disease, e.g., arresting its development; and (c) relieving the disease, e.g., causing regression of the disease.

The terms "individual," "subject," "host," and "patient," used interchangeably herein, refer to an individual organism, e.g., a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CasMG polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Description

The present disclosure provides RNA-guided endonuclease polypeptides and RNA-guided DNA binding proteins, referred to herein as "CasMG" polypeptides (also referred to as "CasMG proteins"); nucleic acids encoding the CasMG polypeptides; and modified host cells comprising the CasMG polypeptides and/or nucleic acids encoding same. CasMG polypeptides are useful in a variety of applications, which are provided. For purposes of this disclosure, a CasMG polypeptide is a CasMG1, CasMG2, CasMG3, CasMG4, CasMG5, CasMG6, CasMG7, CasMG8, CasMG9, or CasMG10 polypeptide, fusion polypeptide, or variant thereof.

The present disclosure provides guide RNAs (referred to herein as "CasMG guide RNAs") that bind to and provide sequence specificity to the CasMG proteins; nucleic acids encoding the CasMG guide RNAs; and modified host cells comprising the CasMG guide RNAs and/or nucleic acids encoding same. CasMG guide RNAs are useful in a variety of applications, which are provided. In some cases, a CasMG guide RNA is a CasMG1, CasMG2, CasMG3, CasMG4, CasMG5, CasMG6, CasMG7, CasMG8, CasMG9, or CasMG10 guide RNA.

A CRISPR/Cas endonuclease (e.g., a CasMG polypeptide) interacts with (binds to) a corresponding guide RNA (e.g., a CasMG guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CasMG polypeptide forms a complex with a CasMG guide RNA and the guide RNA provides sequence specificity to the RNP complex via the guide sequence. The CasMG polypeptide of the complex provides the site-specific activity. In other words, the CasMG polypeptide is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the guide RNA.

The present disclosure provides compositions comprising a CasMG polypeptide, such as a CasMG1, CasMG2, CasMG3, CasMG4, CasMG5, CasMG6, CasMG7, CasMG8, CasMG9, or CasMG10 polypeptide (and/or a nucleic acid encoding the CasMG polypeptide) (e.g., where the CasMG polypeptide can be a naturally-occurring protein, a nickase CasMG protein, a dCasMG protein, a chimeric CasMG protein, or CasMG fusion polypeptide, etc.). The present disclosure also provides compositions comprising a CasMG guide RNA (and/or a nucleic acid encoding the CasMG guide RNA) (e.g., where the CasMG guide RNA can be in dual or single guide format). The present disclosure provides compositions comprising (a) a CasMG polypeptide (and/or a nucleic acid encoding the CasMG polypeptide) (e.g., wherein the CasMG polypeptide can be a naturally-occurring protein, a nickase CasMG protein, a dCasMG protein, a chimeric CasMG protein, a CasMG fusion polypeptide, etc.) and (b) a CasMG guide RNA (and/or a nucleic acid encoding the CasMG guide RNA) (e.g., where the CasMG guide RNA can be in dual or single guide format). The present disclosure provides a nucleic acid/protein complex (RNP complex) comprising: (a) a CasMG polypeptide of the present disclosure (e.g., where the CasMG polypeptide can be a naturally-occurring protein, a nickase CasMG protein, a dCasMG protein, a chimeric CasMG protein, a CasMG fusion polypeptide, etc.); and (b) a CasMG guide RNA (e.g., where the CasMG guide RNA can be in dual or single guide format).

A "CasMG polypeptide" (used interchangeably herein with the term "CasMG protein"), such as a CasMG1, CasMG2, CasMG3, CasMG4, CasMG5, CasMG6, CasMG7, CasMG8. CasMG9, or CasMG10 polypeptide, can bind and/or modify (e.g., cleave, nick, methylate, demethylate, etc.) a target nucleic acid and/or a polypeptide associated with target nucleic acid (e.g., methylation or acetylation of a histone tail) (e.g., in some cases the CasMG polypeptide includes a fusion partner with an activity, and in some cases the CasMG polypeptide provides nuclease activity). In some cases, the CasMG polypeptide is a naturally-occurring protein (e.g., naturally-occurs in prokaryotic cells). In other cases, the CasMG polypeptide is not a naturally-occurring polypeptide (e.g., the CasMG polypeptide is a variant CasMG1 protein, a chimeric protein, a CasMG fusion polypeptide, and the like).

Assays to determine whether given protein interacts with a CasMG guide RNA, such as a CasMG1, CasMG2, CasMG3, CasMG4, CasMG5, CasMG6, CasMG7, CasMG8, CasMG9, or CasMG10 guide RNA, can be any convenient binding assay that tests for binding between a protein and a nucleic acid. Suitable binding assays (e.g., gel shift assays) will be known to one of ordinary skill in the art (e.g., assays that include adding a CasMG guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally-occurring CasMG protein functions as an endonuclease that catalyzes a strand break (double or single strand) at a specific sequence in a targeted DNA. The sequence specificity is provided by the associated guide RNA, which hybridizes to a target sequence within the target DNA. The naturally-occurring guide RNA may include a tracrRNA hybridized to a crRNA or, where the crRNA includes a guide sequence that hybridizes to a target sequence in the target DNA.

As used herein. CasMG endonuclease activity refers to CRISPR endonuclease activity wherein, a guide RNA associated with a CasMG polypeptide, such as a CasMG1, CasMG2, CasMG3, CasMG4, CasMG5, CasMG6, CasMG7, CasMG8, CasMG9, or CasMG10) polypeptide, causes the CasMG-guide RNA complex to bind to a predetermined nucleotide sequence that is complementary to the gRNA; and wherein CasMG endonuclease activity can introduce a strand break at or near the site targeted by the gRNA. In some cases, this is a double-stranded break, and it may be a blunt or a staggered DNA double-stranded break. As used herein a "staggered DNA double-stranded break" can result in a double strand break with about 1, about 2, about 3, about 4, about 5, about 6, about 7, about 8, about 9, or about 10 nucleotides of overhang on either the 3' or 5' ends following cleavage. The double strand break can occur at or near the sequence to which the guide sequence is targeted.

In some cases, the CasMG protein of the subject methods and/or compositions is (or is derived from) a naturally-occurring (wild type) protein. The sequence of a naturally-occurring CasMG1 protein is shown in SEQ ID NO: 1. The sequence of a naturally-occurring CasMG2 protein is shown in SEQ ID NO: 59. The sequence of a naturally-occurring CasMG3 protein is shown in SEQ ID NO: 66. The sequence of a naturally-occurring CasMG4 protein is shown in SEQ ID NO: 73. The sequence of a naturally-occurring CasMG5 protein is shown in SEQ ID NO: 80. The sequence of a naturally-occurring CasMG6 protein is shown in SEQ ID NO: 87. The sequence of a naturally-occurring CasMG7 protein is shown in SEQ ID NO: 94. The sequence of a naturally-occurring CasMG8 protein is shown in SEQ ID NO: 101. The sequence of a naturally-occurring CasMG9 protein is shown in SEQ ID NO: 108. The sequence of a naturally-occurring CasMG10 protein is shown in SEQ ID NO: 115.

In some cases, a CasMG1 protein (of the subject compositions and/or methods) includes an amino acid sequence having 20% or more sequence identity (e.g., 30% or more, 40% or or more, 97% or more, 98% or more, 99% or more, or 100% sequence identity) with the CasMG1 protein sequence set forth as SEQ ID NO: 1. For example, in some cases, a CasMG1 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG1 protein sequence set forth as SEQ ID NO: 1. In some cases, a CasMG1 protein includes an amino acid sequence having 80% or more sequence identity (e.g., 85% or more, 90% or more, 95% or more, 97% or more, 98% or more, 99% or more, or 100% sequence identity) with the CasMG1 protein sequence set forth as SEQ ID NO: 1. In some cases, a CasMG1 protein includes an amino acid sequence having 90% or more sequence identity (e.g., 95% or more, 97% or more, 98% or more, 99% or more, 99.5%, 99.8%, 99.9%, or 100% sequence identity) with the CasMG1 protein sequence set forth as SEQ ID NO: 1. In some cases, a CasMG1 protein includes an amino acid sequence having the CasMG1 protein sequence set forth as SEQ ID NO: 1. In some cases, a CasMG1 protein includes an amino acid sequence having the CasMG1 protein sequence set forth as SEQ ID NO: 1, with the exception that the sequence includes an amino acid substitution (e.g., 1, 2, or 3 amino acid substitutions) that reduces the naturally-occurring catalytic activity of the protein (e.g., such as at amino acid positions described below). A CasMG1 fusion polypeptide can comprise any of the aforementioned CasMG1 proteins.

In some cases, a CasMG2 protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasMG2 protein sequence set forth as SEQ ID NO: 59. For example, in some cases, a CasMG2 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG2 protein sequence set forth as SEQ ID NO: 59. In some cases, a CasMG2 protein includes an amino acid sequence having 80% or more sequence identity (e.g., 85% or more, 90% or more, 95% or more, 97% or more, 98% or more, 99% or more, or 100% sequence identity) with the CasMG2 protein sequence set forth as SEQ ID NO: 59. In some cases, a CasMG2 protein includes an amino acid sequence having 90% or more sequence identity (e.g., 95% or more, 97% or more, 98% or more, 99% or more, 99.5%, 99.8%, 99.9%, or 100% sequence identity) with the CasMG2 protein sequence set forth as SEQ ID NO: 59. In some cases, a CasMG2 protein includes an amino acid sequence having the CasMG2 protein sequence set forth as SEQ ID NO: 59. In some cases, a CasMG2 protein includes an amino acid sequence having the CasMG2 protein sequence set forth as SEQ ID NO: 59, with the exception that the sequence includes an amino acid substitution (e.g., 1, 2, or 3 amino acid substitutions) that reduces the naturally-occurring catalytic activity of the protein (e.g., such as at amino acid positions described below). A CasMG2 fusion polypeptide can comprise any of the aforementioned CasMG2 proteins.

In some cases, a CasMG3 protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasMG3 protein sequence set forth as SEQ ID NO: 66. For example, in some cases, a CasMG3 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG3 protein sequence set forth as SEQ ID NO: 66. In some cases, a CasMG3 protein includes an amino acid sequence having 80% or more sequence identity (e.g., 85% or more, 90% or more, 95% or more, 97% or more, 98% or more, 99% or more, or 100% sequence identity) with the CasMG3 protein sequence set forth as SEQ ID NO: 66. In some cases, a CasMG3 protein includes an amino acid sequence having 90% or more sequence identity (e.g., 95% or more, 97% or more, 98% or more, 99% or more, 99.5%, 99.8%, 99.9%, or 100% sequence identity) with the CasMG3 protein sequence set forth as SEQ ID NO: 66. In some cases, a CasMG3 protein includes an amino acid sequence having the CasMG3 protein sequence set forth as SEQ ID NO: 66. In some cases, a CasMG3 protein includes an amino acid sequence having the CasMG3 protein sequence set forth as SEQ ID NO: 66, with the exception that the sequence includes an amino acid substitution (e.g., 1, 2, or 3 amino acid substitutions) that reduces the naturally-occurring catalytic activity of the protein (e.g., such as at amino acid positions described below). A CasMG3 fusion polypeptide can comprise any of the aforementioned CasMG3 proteins.

In some cases, a CasMG4 protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasMG4 protein sequence set forth as SEQ ID NO: 73. For example, in some cases, a CasMG4 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG4 protein sequence set forth as SEQ ID NO: 73. In some cases, a CasMG4 protein includes an amino acid sequence having 98% or more, 99% or more, or 100% sequence identity) with the CasMG4 protein sequence set forth as SEQ ID NO: 73. In some cases, a CasMG4 protein includes an amino acid sequence having 90% or more sequence identity (e.g., 95% or more, 97% or more, 98% or more, 99% or more, 99.5%, 99.8%, 99.9%, or 100% sequence identity) with the CasMG4 protein sequence set forth as SEQ ID NO: 73. In some cases, a CasMG4 protein includes an amino acid sequence having the CasMG4 protein sequence set forth as SEQ ID NO: 73. In some cases, a CasMG4 protein includes an amino acid sequence having the CasMG4 protein sequence set forth as SEQ ID NO: 73, with the exception that the sequence includes an amino acid substitution (e.g., 1, 2, or 3 amino acid substitutions) that reduces the naturally-occurring catalytic activity of the protein (e.g., such as at amino acid positions described below). A CasMG4 fusion polypeptide can comprise any of the aforementioned CasMG4 proteins.

In some cases, a CasMG5 protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasMG5 protein sequence set forth as SEQ ID NO: 80. For example, in some cases, a CasMG5 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG5 protein sequence set forth as SEQ ID NO: 80. In some cases, a CasMG2 protein includes an amino acid sequence having 80% or more sequence identity (e.g., 85% or more, 90% or more, 95% or more, 97% or more, 98% or more, 99% or more, or 100% sequence identity) with the CasMG5 protein sequence set forth as SEQ ID NO: 80. In some cases, a CasMG5 protein includes an amino acid sequence having 90% or more sequence identity (e.g., 95% or more, 97% or more, 98% or more, 99% or more, 99.5%, 99.8%, 99.9%, or 100% sequence identity) with the CasMG5 protein sequence set forth as SEQ ID NO: 80. In some cases, a CasMG5 protein includes an amino acid sequence having the CasMG5 protein sequence set forth as SEQ ID NO: 80. In some cases, a CasMG5 protein includes an amino acid sequence having the CasMG5 protein sequence set forth as SEQ ID NO: 80, with the exception that the sequence includes an amino acid substitution (e.g., 1, 2, or 3 amino acid substitutions) that reduces the naturally-occurring catalytic activity of the protein (e.g., such as at amino acid positions described below). A CasMG5 fusion polypeptide can comprise any of the aforementioned CasMG5 proteins.

In some cases, a CasMG6 protein (of the subject compositions and/or methods) includes an amino acid sequence having 20% or more sequence identity (e.g., 30% or more, 40% or or more, 97% or more, 98% or more, 99% or more, or 100% sequence identity) with the CasMG6 protein sequence set forth as SEQ ID NO: 87. For example, in some cases, a CasMG6 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG6 protein sequence set forth as SEQ ID NO: 87. In some cases, a CasMG6 protein includes an amino acid sequence having 80% or more sequence identity (e.g., 85% or more, 90% or more, 95% or more, 97% or more, 98% or more, 99% or more, or 100% sequence identity) with the CasMG6 protein sequence set forth as SEQ ID NO: 87. In some cases, a CasMG6 protein includes an amino acid sequence having 90% or more sequence identity (e.g., 95% or more, 97% or more, 98% or more, 99% or more, 99.5%, 99.8%, 99.9%, or 100% sequence identity) with the CasMG6 protein sequence set forth as SEQ ID NO: 87. In some cases, a CasMG6 protein includes an amino acid sequence having the CasMG6 protein sequence set forth as SEQ ID NO: 87. In some cases, a CasMG6 protein includes an amino acid sequence having the CasMG6 protein sequence set forth as SEQ ID NO: 87, with the exception that the sequence includes an amino acid substitution (e.g., 1, 2, or 3 amino acid substitutions) that reduces the naturally-occurring catalytic activity of the protein (e.g., such as at amino acid positions described below). A CasMG6 fusion polypeptide can comprise any of the aforementioned CasMG6 proteins.

In some cases, a CasMG7 protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasMG7 protein sequence set forth as SEQ ID NO: 94. For example, in some cases, a CasMG7 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG7 protein sequence set forth as SEQ ID NO: 94. In some cases, a CasMG7 protein includes an amino acid sequence having 80% or more sequence identity (e.g., 85% or more, 90% or more, 95% or more, 97% or more, 98% or more, 99% or more, or 100% sequence identity) with the CasMG7 protein sequence set forth as SEQ ID NO: 94. In some cases, a CasMG7 protein includes an amino acid sequence having 90% or more sequence identity (e.g., 95% or more, 97% or more, 98% or more, 99% or more, 99.5%, 99.8%, 99.9%, or 100% sequence identity) with the CasMG7 protein sequence set forth as SEQ ID NO: 94. In some cases, a CasMG7 protein includes an amino acid sequence having the CasMG7 protein sequence set forth as SEQ ID NO: 94. In some cases, a CasMG7 protein includes an amino acid sequence having the CasMG7 protein sequence set forth as SEQ ID NO: 94, with the exception that the sequence includes an amino acid substitution (e.g., 1, 2, or 3 amino acid substitutions) that reduces the naturally-occurring catalytic activity of the protein (e.g., such as at amino acid positions described below). A CasMG7 fusion polypeptide can comprise any of the aforementioned CasMG7 proteins.

In some cases, a CasMG8 protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasMG8 protein sequence set forth as SEQ ID NO: 101. For example, in some cases, a CasMG8 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG8 protein sequence set forth as SEQ ID NO: 101. In some cases, a CasMG8 protein includes an amino acid sequence having 80% or more sequence identity (e.g., 85% or more, 90% or more, 95% or more, 97% or more, 98% or more, 99% or more, or 100% sequence identity) with the CasMG8 protein sequence set forth as SEQ ID NO: 101. In some cases, a CasMG8 protein includes an amino acid sequence having 90% or more sequence identity (e.g., 95% or more, 97% or more, 98% or more, 99% or more, 99.5%, 99.8%, 99.9%, or 100% sequence identity) with the CasMG8 protein sequence set forth as SEQ ID NO: 101. In some cases, a CasMG8 protein includes an amino acid sequence having the CasMG8 protein sequence set forth as SEQ ID NO: 101. In some cases, a CasMG8 protein includes an amino acid sequence having the CasMG8 protein sequence set forth as SEQ ID NO: 101, with the exception that the sequence includes an amino acid substitution (e.g., 1, 2, or 3 amino acid substitutions) that reduces the naturally-occurring catalytic activity of the protein (e.g., such as at amino acid positions described below). A CasMG8 fusion polypeptide can comprise any of the aforementioned CasMG8 proteins.

In some cases, a CasMG9 protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasMG9 protein sequence set forth as SEQ ID NO: 108. For example, in some cases, a CasMG9 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG9 protein sequence set forth as SEQ ID NO: 108. In some cases, a CasMG9 protein includes an amino acid sequence having 98% or more, 99% or more, or 100% sequence identity) with the CasMG9 protein sequence set forth as SEQ ID NO: 108. In some cases, a CasMG9 protein includes an amino acid sequence having 90% or more sequence identity (e.g., 95% or more, 97% or more, 98% or more, 99% or more, 99.5%, 99.8%, 99.9%, or 100% sequence identity) with the CasMG9 protein sequence set forth as SEQ ID NO: 108. In some cases, a CasMG9 protein includes an amino acid sequence having the CasMG9 protein sequence set forth as SEQ ID NO: 108. In some cases, a CasMG9 protein includes an amino acid sequence having the CasMG9 protein sequence set forth as SEQ ID NO: 108, with the exception that the sequence includes an amino acid substitution (e.g., 1, 2, or 3 amino acid substitutions) that reduces the naturally-occurring catalytic activity of the protein (e.g., such as at amino acid positions described below). A CasMG9 fusion polypeptide can comprise any of the aforementioned CasMG9 proteins.

In some cases, a CasMG10 protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasMG10 protein sequence set forth as SEQ ID NO: 115. For example, in some cases, a CasMG10 protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasMG10 protein sequence set forth as SEQ ID NO: 115. In some cases, a CasMG10 protein includes an amino acid sequence having 80% or more sequence identity (e.g., 85% or more, 90% or more, 95% or more, 97% or more, 98% or more, 99% or more, or 100% sequence identity) with the CasMG10) protein sequence set forth as SEQ ID NO: 115. In some cases, a CasMG10 protein includes an amino acid sequence having 90% or more sequence identity (e.g., 95% or more, 97% or more, 98% or more, 99% or more, 99.5%, 99.8%, 99.9%, or 100% sequence identity) with the CasMG10 protein sequence set forth as SEQ ID NO: 115. In some cases, a CasMG10 protein includes an amino acid sequence having the CasMG10 protein sequence set forth as SEQ ID NO: 115. In some cases, a CasMG10 protein includes an amino acid sequence having the CasMG10 protein sequence set forth as SEQ ID NO: 115, with the exception that the sequence includes an amino acid substitution (e.g., 1, 2, or 3 amino acid substitutions) that reduces the naturally-occurring catalytic activity of the protein (e.g., such as at amino acid positions described below). A CasMG10 fusion polypeptide can comprise any of the aforementioned CasMG10 proteins.

A CasMG protein includes 3 partial RuvC domains (RuvC-I, RuvC-II, and RuvC-III, also referred to herein as subdomains) that are not contiguous with respect to the primary amino acid sequence of the CasMG protein, but form a RuvC domain once the protein is produced and folds.

In some cases, a CasMG1 protein (of the subject compositions and/or methods) includes a split RuvC domain (e.g., 3 partial RuvC domains-RuvC-I, RuvC-II, and RuvC-III) with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 1. The catalytic residues of the RuvC domain of CasMG1 are SEQ ID NO: 54 for RuvC-I, SEQ ID NO: 55 for RuvC-II, and SEQ ID NO: 56 for RuvC-III. In certain embodiments. CasMG1 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity) with the CasMG1 protein sequence set forth as SEQ ID NO: 1, wherein at least one of the RuvC subdomains of SEQ ID NO: 54, SEQ ID NO: 55, and/or SEQ ID NO: 56 are present. A CasMG1 fusion polypeptide can comprise any of the aforementioned CasMG1 proteins.

In some cases, a CasMG2 protein (of the subject compositions and/or methods) includes a split RuvC domain (e.g., 3 partial RuvC domains-RuvC-I, RuvC-II, and RuvC-III)

with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 59. The catalytic residues of the RuvC domain of CasMG2 are SEQ ID NO: 63 for RuvC-I, SEQ ID NO: 64 for RuvC-II, and SEQ ID NO: 65 for RuvC-III. In certain embodiments. CasMG2 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity) with the CasMG2 protein sequence set forth as SEQ ID NO: 59, wherein at least one of the RuvC subdomains of SEQ ID NO: 63, SEQ ID NO: 64, and/or SEQ ID NO: 65 are present. A CasMG2 fusion polypeptide can comprise any of the aforementioned CasMG2 proteins.

In some cases, a CasMG3 protein (of the subject compositions and/or methods) includes a split RuvC domain (e.g., 3 partial RuvC domains-RuvC-I, RuvC-II, and RuvC-III) with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 66. The catalytic residues of the RuvC domain of CasMG3 are SEQ ID NO: 70 for RuvC-I, SEQ ID NO: 71 for RuvC-II, and SEQ ID NO: 72 for RuvC-III. In certain embodiments. CasMG3 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity) with the CasMG3 protein sequence set forth as SEQ ID NO: 66, wherein at least one of the RuvC subdomains of SEQ ID NO: 70, SEQ ID NO: 71, and/or SEQ ID NO: 72 are present. A CasMG3 fusion polypeptide can comprise any of the aforementioned CasMG3 proteins.

In some cases, a CasMG4 protein (of the subject compositions and/or methods) includes a split RuvC domain (e.g., 3 partial RuvC domains-RuvC-I, RuvC-II, and RuvC-III) with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 73. The catalytic residues of the RuvC domain of CasMG4 are SEQ ID NO: 77 for RuvC-I, SEQ ID NO: 78 for RuvC-II, and SEQ ID NO: 79 for RuvC-III. In certain embodiments. CasMG4 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity) with the CasMG4 protein sequence set forth as SEQ ID NO: 73, wherein at least one of the RuvC subdomains of SEQ ID NO: 77, SEQ ID NO: 78, and/or SEQ ID NO: 79 are present. A CasMG4 fusion polypeptide can comprise any of the aforementioned CasMG4 proteins.

In some cases, a CasMG5 protein (of the subject compositions and/or methods) includes a split RuvC domain (e.g., 3 partial RuvC domains-RuvC-I, RuvC-II, and RuvC-III) with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 80. The catalytic residues of the RuvC domain of CasMG5 are SEQ ID NO: 84 for RuvC-I, SEQ ID NO: 85 for RuvC-II, and SEQ ID NO: 86 for RuvC-III. In certain embodiments. CasMG5 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity) with the CasMG5 protein sequence set forth as SEQ ID NO: 80, wherein at least one of the RuvC subdomains of SEQ ID NO: 84, SEQ ID NO: 85, and/or SEQ ID NO: 86 are present. A CasMG5 fusion polypeptide can comprise any of the aforementioned CasMG5 proteins.

In some cases, a CasMG6 protein (of the subject compositions and/or methods) includes a split RuvC domain (e.g., 3 partial RuvC domains-RuvC-I, RuvC-II, and RuvC-III) with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 87. The catalytic residues of the RuvC domain of CasMG6 are SEQ ID NO: 91 for RuvC-I, SEQ ID NO: 92 for RuvC-II, and SEQ ID NO: 93 for RuvC-III. In certain embodiments. CasMG6 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity) with the CasMG6 protein sequence set forth as SEQ ID NO: 87, wherein at least one of the RuvC subdomains of SEQ ID NO: 91, SEQ ID NO: 92, and/or SEQ ID NO: 93 are present. A CasMG6 fusion polypeptide can comprise any of the aforementioned CasMG6 proteins.

In some cases, a CasMG7 protein (of the subject compositions and/or methods) includes a split RuvC domain (e.g., 3 partial RuvC domains-RuvC-I, RuvC-II, and RuvC-III) with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 94. The catalytic residues of the RuvC domain of CasMG7 are SEQ ID NO: 98 for RuvC-I, SEQ ID NO: 99 for RuvC-II, and SEQ ID NO: 100 for RuvC-III. In certain embodiments. CasMG7 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity) with the CasMG7 protein sequence set forth as SEQ ID NO: 94, wherein at least one of the RuvC subdomains of SEQ ID NO: 98, SEQ ID NO:

99, and/or SEQ ID NO: 100 are present. A CasMG7 fusion polypeptide can comprise any of the aforementioned CasMG7 proteins.

In some cases, a CasMG8 protein (of the subject compositions and/or methods) includes a split RuvC domain (e.g., 3 partial RuvC domains-RuvC-I, RuvC-II, and RuvC-III) with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 101. The catalytic residues of the RuvC domain of CasMG8 are SEQ ID NO: 105 for RuvC-I, SEQ ID NO: 106 for RuvC-II, and SEQ ID NO: 107 for RuvC-III. In certain embodiments. CasMG8 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity) with the CasMG8 protein sequence set forth as SEQ ID NO: 101, wherein at least one of the RuvC subdomains of SEQ ID NO: 105, SEQ ID NO: 106, and/or SEQ ID NO: 107 are present. A CasMG8 fusion polypeptide can comprise any of the aforementioned CasMG8 proteins.

In some cases, a CasMG9 protein (of the subject compositions and/or methods) includes a split RuvC domain (e.g., 3 partial RuvC domains-RuvC-I, RuvC-II, and RuvC-III) with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 108. The catalytic residues of the RuvC domain of CasMG9 are SEQ ID NO: 112 for RuvC-I, SEQ ID NO: 113 for RuvC-II, and SEQ ID NO: 114 for RuvC-III. In certain embodiments. CasMG9 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity) with the CasMG9 protein sequence set forth as SEQ ID NO: 108, wherein at least one of the RuvC subdomains of SEQ ID NO: 112, SEQ ID NO: 113, and/or SEQ ID NO: 114 are present. A CasMG9 fusion polypeptide can comprise any of the aforementioned CasMG9 proteins.

In some cases, a CasMG10 protein (of the subject compositions and/or methods) includes a split RuvC domains (e.g., 2 partial RuvC domains-RuvC-I, and RuvC-II) with amino acid sequence having 20% or more sequence identity (e.g., 30% or more, 40% or more, 50% or more, 60) % or more, 70% or more, 80% or more, 85% or more, 90% or more, 95% or more, 97% or more, 98% or more, 99% or more, or 100% sequence identity) with the split RuvC domain of SEQ ID NO: 115. The catalytic residues of the RuvC domain of CasMG10 are SEQ ID NO: 119 for RuvC-I, and SEQ ID NO: 120 for RuvC-II. In certain embodiments. CasMG10 proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity with the CasMG10 protein sequence set forth as SEQ ID NO: 115, wherein at least one of the RuvC subdomains of SEQ ID NO: 119 and/or SEQ ID NO: 120 are present. In certain embodiments, a CasMG10 protein can further comprise a third RuvC-III amino acid sequence located C-terminal to the Ruv-CII sequence. Examples of such RuvC-III amino acid sequences that can be used in CasMG10 protein include SEQ ID NO: 121 and other sequences having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) to SEQ ID NO: 121. A CasMG10 fusion polypeptide can comprise any of the aforementioned CasMG10) proteins.

A variant CasMG protein (e.g., a variant CasMG1, variant CasMG2, variant CasMG3, variant CasMG4, variant CasMG5, variant CasMG6, variant CasMG7, variant CasMG8, variant CasMG9, or variant CasMG10 protein) has an amino acid sequence that is different by at least one amino acid (e.g., has a deletion, insertion, substitution, fusion) when compared to the amino acid sequence of the corresponding wild-type CasMG protein. A CasMG protein that cleaves one strand but not the other of a double stranded target nucleic acid is referred to herein as a "nickase" (e.g., a "nickase CasMG1," "nickase CasMG2," "nickase CasMG3," "nickase CasMG4," "nickase CasMG5," "nickase CasMG6," "nickase CasMG7," "nickase CasMG8," "nickase CasMG9," or "nickase CasMG10"). A CasMG protein that has substantially no nuclease activity is referred to herein as a dead CasMG protein (e.g., "dCasMG1," "dCasMG2," "dCasMG 3," "dCasMG4," "dCasMG5," "dCasMG6," "dCasMG7," "dCasMG8," "dCasMG9," or "dCasMG10") (with the caveat that nuclease activity can be provided by a heterologous polypeptide—a fusion partner—in the case of a chimeric CasMG protein (e.g., a chimeric CasMG1, chimeric CasMG2, chimeric CasMG3, chimeric CasMG4, chimeric CasMG5, chimeric CasMG6, chimeric CasMG7, chimeric CasMG8, chimeric CasMG9, or chimeric CasMG10 protein) or a CasMG fusion polypeptide (e.g., a CasMG1 fusion polypeptide, a CasMG2 fusion polypeptide, a CasMG3 fusion polypeptide, a CasMG4 fusion polypeptide, a CasMG5 fusion polypeptide, a CasMG6 fusion polypeptide, a CasMG7 fusion polypeptide, a CasMG8 fusion polypeptide, a CasMG9 fusion polypeptide, or a CasMG10 fusion polypeptide), which are described in more detail below. For any of the CasMG variant proteins described herein (e.g., nickase CasMG, dCasMG, chimeric CasMG. CasMG fusion polypeptide), the CasMG variant can include a CasMG protein sequence with the same parameters described above (e.g., domains that are present, percent identity, and the like).

In certain embodiments, a CasMG protein as described anywhere herein is a variant CasMG protein, e.g., mutated relative to the naturally-occurring catalytically active sequence, and exhibits reduced cleavage activity (e.g., exhibits 90%, or less, 80% or less, 70% or less, 60% or less, 50% or less, 40% or less, 30% or less, 20% or less, 10% or less, 5% or less, or 1% or less cleavage activity) when compared to the corresponding naturally-occurring sequence. In some cases, such a variant CasMG protein is a catalytically 'dead' protein (has substantially no cleavage activity) and can be referred to as a 'dCasMG.' In some cases, the variant CasMG protein is a nickase (cleaves only one strand of a double stranded target nucleic acid, e.g., a double stranded target DNA). As described in more detail herein, in some cases, a CasMG protein (in some case a CasMG protein with wild type cleavage activity and in some cases a variant CasMG with reduced cleavage activity, e.g., a dCasMG or a nickase CasMG) is fused (conjugated) to a heterologous polypeptide that has an activity of interest (e.g., a catalytic activity of interest) to form a fusion protein (e.g., a chimeric CasMG protein or a CasMG fusion polypeptide).

A variant CasMG polypeptide (e.g., a variant CasMG1, variant CasMG2, variant CasMG3, variant CasMG4, variant CasMG5, variant CasMG6, variant CasMG7, variant CasMG8, variant CasMG9, or variant CasMG10 polypeptide) can include one or more mutations that enhance protein function. In certain embodiments. CasMG protein enhancement mutations alter the level of gene editing by the CasMG scaffold protein polypeptide, as compared to a CasMG polypeptide lacking the mutations. In certain embodiments, the effect of the CasMG enhancement mutations may include: altered translation, folding, and/or stability of the protein or RNP; altered affinity and/or specificity of target binding; altered nuclease efficiency on target and/or non-target strands; altered PAM recognition specificity; altered half-life as it may be measured in vivo and/or in vitro; and altered DNA repair outcomes (e.g., increased frequencies of target gene editing and/or decreased frequencies of non-target gene mutations). In certain embodiments, characteristics altered by the CasMG enhancement mutations include: higher solubility, longer active lifespan in vivo or in vitro (e.g., increased half-life), or improved enzymatic activity as may be measured by higher Kcat and or/lower Km, or higher substrate specificity. CasMG1 protein enhancement mutations include mutations comprising or corresponding to Y277P, A487K, T880A, A904F/Q, Q934E, I956K, I964V, N1004D, T1012F/Y, Y1116F, and/or C1140G substitutions in SEQ ID NO: 1, CasMG2 protein enhancement mutations include mutations comprising or corresponding to R545K, S957A, Q981F, T1041V, N1082D, F1092Y, and Y1205F in SEQ ID NO: 59, CasMG3 protein enhancement mutations include mutations comprising or corresponding to Y296F, T920A, F944Q, C1047N/D, F1057Y, and K1213L in SEQ ID NO: 66, CasMG4 protein enhancement mutations include mutations comprising or corresponding to D505N, Q513K, C912A, D919N, I936F/Q, A966E, N1037D, F1047Y, Y1159F, A1186G, and P1204L in SEQ ID NO: 73, CasMG5 protein enhancement mutations include mutations comprising or corresponding to D291P, D505N, Q513K, V913A, L937F/Q, I958L, D967E, N989K, I997V, D1038N, I1048F/Y, Y1158F, and F1198L in SEQ ID NO: 80, CasMG6 protein enhancement mutations include mutations comprising or corresponding to D508N, Q516K, C921A, D928N, V945F/Q, R994K. N1043D, I1053F/Y, Y1167F, and A1196G in SEQ ID NO: 87, CasMG7 protein enhancement mutations include mutations comprising or corresponding to L464I, D513N, Q521K, D944N. F961Q, L1012K, D1061N, I1071F/Y, and A1209G in SEQ ID NO: 94, CasMG8 protein enhancement mutations include mutations comprising or corresponding to L294F, F927Q, F948L, D957E, D1032N, F1042Y, and K1194L in SEQ ID NO: 101, CasMG9 protein enhancement mutations include mutations comprising or corresponding to L295F, F928Q. D1034N, F1044Y, and A1196L in SEQ ID NO: 108, CasMG10 protein enhancement mutations include mutations comprising or corresponding to I277F, V411I, S461N, V907A, K931F/Q, F952L, R980K, D1030N, F1038Y, and/or L1156G in SEQ ID NO: 115.

To initiate DNA cleavage, a CasMG polypeptide (e.g., a CasMG1, CasMG2, variant CasMG3, CasMG4, CasMG5, CasMG6, CasMG7, CasMG8, CasMG9, or CasMG10 polypeptide) complexes with one or more RNA molecules (guide RNA) comprising a sequence complementary to the intended target site. To cleave DNA in vitro, a purified wild-type or mutated CasMG polypeptide is pre-complexed to guide RNA and incubated with linear double-stranded DNA (e.g., linearized plasmid DNA) having a sequence region complementary to that of the guide RNA. The extent of the cleavage reaction is monitored at different time points or enzyme concentrations by, for example, polyacrylamide gel electrophoresis (Kleinstiver et al. Nat Biotechnol. 2019, 37 (3): 276-282, doi: 10.1038/s41587-018-0011-0). Compared to the wild type CasMG1 polypeptide, digestion by the mutant CasMG1 polypeptide comprising one or more of the CasMG1 protein mutations that include mutations comprising or corresponding to Y277P, A487K, T880A, A904F/Q, Q934E, I956K, I964V, N1004D, T1012F/Y, Y1116F, and/or C1140G in SEQ ID NO: 1 may differ in reaction rate, specificity toward the target sequence, enzymatic turnover, product composition (e.g., nicked dsDNA), and/or temperature optimality. In certain embodiments, a mutant CasMG1 polypeptide comprising one or more of the CasMG1 protein mutations that include mutations comprising or corresponding to Y277P, A487K. T880A, A904F/Q, Q934E, I956K, I964V, N1004D, T1012F/Y, Y1116F, and/or C1140G in SEQ ID NO: 1 may differ from the wild-type CasMG1 polypeptide in processing or binding the guide RNA, or may enable non-natural modifications, insertions, 5' or 3' extensions, or 5' or 3' truncations of the guide RNA. In certain embodiments, such mutant CasMG1 polypeptides including those comprising one or more of the CasMG1 protein mutations that include mutations comprising or corresponding to Y277P, A487K, T880A, A904F/Q, Q934E, I956K, I964V, N1004D, T1012F/Y, Y1116F, and/or C1140G in SEQ ID NO: 1 may demonstrate enhanced efficiency of RNP formation, reduced sensitivity to reaction temperature, or reduced dependence on cofactors for complex assembly. Compared to the wild-type CasMG2 polypeptide, digestion by the mutant CasMG2 polypeptide comprising one or more of the CasMG2 protein mutations that include mutations comprising or corresponding to R545K, S957A, Q981F, T1041V, N1082D, F1092Y, and Y1205F in SEQ ID NO: 59 may differ in reaction rate, specificity toward the target sequence, enzymatic turnover, product composition (e.g., nicked dsDNA), and/or temperature optimality. In certain embodiments, a mutant CasMG2 polypeptide comprising one or more of the CasMG2 protein mutations that include mutations comprising or corresponding to R545K, S957A, Q981F, T1041V, N1082D, F1092Y, and Y1205F in SEQ ID NO: 59 may differ from the wild-type CasMG2 polypeptide in processing or binding the guide RNA, or may enable non-natural modifications, insertions, 5' or 3' extensions, or 5' or 3' truncations of the guide RNA. In certain embodiments, such mutant CasMG2 polypeptides including those comprising one or more of the CasMG2 protein mutations that include mutations comprising or corresponding to R545K, S957A, Q981F, T1041V, N1082D, F1092Y, and Y1205F in SEQ ID NO: 59 may demonstrate enhanced efficiency of RNP formation, reduced sensitivity to reaction temperature, or reduced dependence on cofactors for complex assembly. Compared to the wild type CasMG3 polypeptide, digestion by the mutant CasMG3 polypeptide comprising one or more of the CasMG3 protein mutations that include mutations comprising or corresponding to Y296F, T920A, F944Q, C1047N/D, F1057Y, K1213L, and/or T799I in SEQ ID NO: 66 may differ in reaction rate, specificity toward the target sequence, enzymatic turnover, product composition (e.g., nicked dsDNA), and/or temperature optimality. In certain embodiments, a mutant CasMG3 polypeptide comprising one or more of the CasMG3 protein mutations that include mutations comprising or corresponding to Y296F, T920A, F944Q, C1047N/D, F1057Y. K1213, and/or T799I in SEQ ID NO: 66 may differ from the wild-type CasMG3 polypeptide in processing or binding the guide RNA, or may enable non-natural modifications, insertions, 5' or 3' extensions, or 5' or 3' truncations of the guide RNA. In certain embodiments, such mutant CasMG3 polypeptides including those comprising one or more of the CasMG3 protein mutations that include mutations comprising or corresponding to Y296F, T920A, F944Q. C1047N/D, F1057Y, K1213, and/or T799I in SEQ ID NO: 66 may demonstrate enhanced efficiency of RNP formation, reduced sensitivity to reaction temperature, or reduced dependence on cofactors for complex assembly. Compared to the wild type CasMG4 polypeptide, digestion by the mutant CasMG4 polypeptide comprising one or more of the CasMG4 protein mutations that include mutations comprising or corresponding to D505N, Q513K, C912A, D919N, I936F/Q, A966E, N1037D, F1047Y, Y1159F, A1186G, P1204L, and/or L783I in SEQ ID NO: 73 may differ in reaction rate, specificity toward the target sequence, enzymatic turnover, product composition (e.g., nicked dsDNA), and/or temperature optimality. In certain embodiments, a mutant CasMG4 polypeptide comprising one or more of the CasMG4 protein mutations that include mutations comprising or corresponding to D505N, Q513K, C912A. D919N, I936F/Q, A966E, N1037D, F1047Y, Y1159F, A1186G, P1204L, and/or L783I in SEQ ID NO: 73 may differ from the wild-type CasMG4 polypeptide in processing or binding the guide RNA, or may enable non-natural modifications, insertions, 5' or 3' extensions, or 5' or 3' truncations of the guide RNA. In certain embodiments, such mutant CasMG4 polypeptides including those comprising one or more of the CasMG4 protein mutations that include mutations comprising or corresponding to D505N, Q513K, C912A, D919N, I936F/Q, A966E, N1037D. F1047Y, Y1159F, A1186G, P1204L, and/or L783I in SEQ ID NO: 73 may demonstrate enhanced efficiency of RNP formation, reduced sensitivity to reaction temperature, or reduced dependence on cofactors for complex assembly. Compared to the wild type CasMG5 polypeptide, digestion by the mutant CasMG5 polypeptide comprising one or more of the CasMG5 protein mutations that include mutations comprising or corresponding to D291P, D505N, Q513K, V913A, L937F/Q, I958L, D967E, N989K, I997V, D1038N, I1048F/Y, Y1158F, F1198L, and/or L782I in SEQ ID NO: 80 may differ in reaction rate, specificity toward the target sequence, enzymatic turnover, product composition (e.g., nicked dsDNA), and/or temperature optimality. In certain embodiments, a mutant CasMG5 polypeptide comprising one or more of the CasMG5 protein mutations that include mutations comprising or corresponding to D291P, D505N, Q513K, V913A, L937F/Q, I958L, D967E, N989K, I997V, D1038N, I1048F/Y. Y1158F, F1198L, and/or L782I in SEQ ID NO: 80 may differ from the wild-type CasMG5 polypeptide in processing or binding the guide RNA, or may enable non-natural modifications, insertions, 5' or 3' extensions, or 5' or 3' truncations of the guide RNA. In certain embodiments, such mutant CasMG5 polypeptides including those comprising one or more of the CasMG5 protein mutations that include mutations comprising or corresponding to D291P, D505N. Q513K, V913A, L937F/Q, I958L, D967E, N989K, I997V, D1038N, I1048F/Y, Y1158F, F1198L, and/or L782I in SEQ ID NO: 80 may demonstrate enhanced efficiency of RNP formation, reduced sensitivity to reaction temperature, or reduced dependence on cofactors for complex assembly. Compared to the wild type CasMG6 polypeptide, digestion by the mutant CasMG6 polypeptide comprising one or more of the CasMG6 protein mutations that include mutations comprising or corresponding to D508N, Q516K, C921A, D928N, V945F/Q, R994K. N1043D, I1053F/Y, Y1167F, and A1196G and/or L787I in SEQ ID NO: 87 may differ in reaction rate, specificity toward the target sequence, enzymatic turnover, product composition (e.g., nicked dsDNA), and/or temperature optimality. In certain embodiments, a mutant CasMG6 polypeptide comprising one or more of the CasMG6 protein mutations that include mutations comprising or corresponding to D508N, Q516K, C921A, D928N, V945F/Q, R994K, N1043D, I1053F/Y, Y1167F, and A1196G and/or L787I in SEQ ID NO: 87 may differ from the wild-type CasMG6 polypeptide in processing or binding the guide RNA, or may enable non-natural modifications, insertions, 5' or 3' extensions, or 5' or 3' truncations of the guide RNA. In certain embodiments, such mutant CasMG6 polypeptides including those comprising one or more of the CasMG6 protein mutations that include mutations comprising or corresponding to D508N, Q516K, C921A, D928N, V945F/Q, R994K. N1043D, I1053F/Y, Y1167F, A1196G, and/or L787I in SEQ ID NO: 87 may demonstrate enhanced efficiency of RNP formation, reduced sensitivity to reaction temperature, or reduced dependence on cofactors for complex assembly. Compared to the wild type CasMG7 polypeptide, digestion by the mutant CasMG7 polypeptide comprising one or more of the CasMG7 protein mutations that include mutations comprising or corresponding to L464I, D513N, Q521K, D944N, F961Q, L1012K, D1061N. I1071F/Y, A1209G, and/or L816I in SEQ ID NO: 94 may differ in reaction rate, specificity toward the target sequence, enzymatic turnover, product composition (e.g., nicked dsDNA), and/or temperature optimality. In certain embodiments, a mutant CasMG7 polypeptide comprising one or more of the CasMG7 protein mutations that include mutations comprising or corresponding to L464I, D513N, Q521K, D944N, F961Q, L1012K, D1061N, I1071F/Y. A1209G, and/or L816I in SEQ ID NO: 94 may differ from the wild-type CasMG7 polypeptide in processing or binding the guide RNA, or may enable non-natural modifications, insertions, 5' or 3' extensions, or 5' or 3' truncations of the guide RNA. In certain embodiments, such mutant CasMG7 polypeptides including those comprising one or more of the CasMG7 protein mutations that include mutations comprising or corresponding to L464I, D513N, Q521K. D944N, F961Q, L1012K, D1061N, I1071F/Y, A1209G, and/or L816I in SEQ ID NO: 94 may demonstrate enhanced efficiency of RNP formation, reduced sensitivity to reaction temperature, or reduced dependence on cofactors for complex assembly. Compared to the wild type CasMG8 polypeptide, digestion by the mutant CasMG8 polypeptide comprising one or more of the CasMG8 protein mutations that include mutations comprising or corresponding to L294F, F927Q, F948L, D957E, D1032N, F1042Y, and/or K1194L in SEQ ID NO: 101 may differ in reaction rate, specificity toward the target sequence, enzymatic turnover, product composition (e.g., nicked dsDNA), and/or temperature optimality. In certain embodiments, a mutant CasMG8 polypeptide comprising one or more of the CasMG8 protein mutations that include mutations comprising or corresponding to L294F, F927Q, F948L, D957E, D1032N, F1042Y, and/or K1194L in SEQ ID NO: 101 may differ from the wild-type CasMG8 polypeptide in processing or binding the guide RNA, or may enable non-natural modifications, insertions, 5' or 3' extensions, or 5' or 3' truncations of the guide RNA. In certain embodiments, such mutant CasMG8 polypeptides including those comprising one or more of the CasMG8 protein mutations that include mutations comprising or corresponding to L294F, F927Q, F948L, D957E, D1032N, F1042Y, and/or K1194L in SEQ ID NO: 101 may demonstrate enhanced efficiency of RNP formation, reduced sensitivity to reaction temperature, or reduced dependence on cofactors for complex assembly. Compared to the wild type CasMG9 polypeptide, digestion by the mutant CasMG9 polypeptide comprising one or more of the CasMG9 protein mutations that include mutations comprising or corresponding to L295F, F928Q, D1034N, F1044Y, and/or A1196L in SEQ ID NO: 108 may differ in reaction rate, specificity toward the target sequence, enzymatic turnover, product composition (e.g., nicked dsDNA), and/or temperature optimality. In certain embodiments, a mutant CasMG9 polypeptide comprising one or more of the CasMG9 protein mutations that include mutations comprising or corresponding to L295F, F928Q, D1034N, F1044Y, and/or A1196L in SEQ ID NO: 108 may differ from the wild-type CasMG9 polypeptide in processing or binding the guide RNA, or may enable non-natural modifications, insertions, 5' or 3' extensions, or 5' or 3' truncations of the guide RNA. In certain embodiments, such mutant CasMG9 polypeptides including those comprising one or more of the CasMG9 protein mutations that include mutations comprising or corresponding to L295F, F928Q. D1034N, F1044Y, and/or A1196L in SEQ ID NO: 108 may demonstrate enhanced efficiency of RNP formation, reduced sensitivity to reaction temperature, or reduced dependence on cofactors for complex assembly. Compared to the wild type CasMG10 polypeptide, digestion by the mutant CasMG10 polypeptide comprising one or more of the CasMG10 protein mutations that include mutations comprising or corresponding to I277F, V411I, S46 IN, V907A, K931F/Q, F952L, R980K, D1030N, F1038Y. L1156G, and/or L789I in SEQ ID NO: 115 may differ in reaction rate, specificity toward the target sequence, enzymatic turnover, product composition (e.g., nicked dsDNA), and/or temperature optimality. In certain embodiments, a mutant CasMG10 polypeptide comprising one or more of the CasMG10 protein mutations that include mutations comprising or corresponding to I277F, V411I, S46 IN, V907A, K931F/Q, F952L. R980K, D1030N, F1038Y. L1156G, and/or L789I in SEQ ID NO: 115 may differ from the wild-type CasMG10 polypeptide in processing or binding the guide RNA, or may enable non-natural modifications, insertions, 5' or 3' extensions, or 5' or 3' truncations of the guide RNA. In certain embodiments, such mutant CasMG10 polypeptides including those comprising one or more of the CasMG10 protein mutations that include mutations comprising or corresponding to I277F, V411I, S461N, V907A, K931F/Q, F952L, R980K, D1030N, F1038Y. L1156G, and/or L789I in SEQ ID NO: 115 may demonstrate enhanced efficiency of RNP formation, reduced sensitivity to reaction temperature, or reduced dependence on cofactors for complex assembly.

A variant CasMG polypeptide (e.g., a variant CasMG1, variant CasMG2, variant CasMG3, variant CasMG4, variant CasMG5, variant CasMG6, variant CasMG7, variant CasMG8, variant CasMG9, or variant CasMG10 polypeptide) can include but is not limited to one or more mutations that enhance the variant CasMG protein's ability to bind, process, and/or stabilize guide RNA. In certain embodiments, mutations that confer improved ability to bind/stabilize guide RNA may alter target DNA binding affinity and/or sequence specificity of the mutated CasMG polypeptide, and/or DNA editing outcome as compared to a wild-type CasMG polypeptide lacking the mutation(s). An enhanced CasMG3 polypeptide guide RNA binding, processing, and/or stabilization mutation includes a mutation comprising or corresponding to T799I in SEQ ID NO: 66. An enhanced CasMG4 polypeptide guide RNA binding, processing, and/or stabilization mutation includes a mutation comprising or corresponding to L783I in SEQ ID NO: 73. An enhanced CasMG5 polypeptide guide RNA binding, processing, and/or stabilization mutation includes a mutation comprising or corresponding to L782I in SEQ ID NO: 80. An enhanced CasMG6 polypeptide guide RNA binding, processing, and/or stabilization mutation includes a mutation comprising or corresponding to L787I in SEQ ID NO: 87. An enhanced CasMG7 polypeptide guide RNA binding, processing, and/or stabilization mutation includes a mutation comprising or corresponding to L816I in SEQ ID NO: 94. An enhanced CasMG10 polypeptide guide RNA binding, processing, and/or stabilization mutation includes a mutation comprising or corresponding to L789I in SEQ ID NO: 115.

Conserved catalytic residues of CasMG1 include the RuvC subdomain residues identified above. N799, E893, and D1129 numbered according to SEQ ID NO: 1, are residues that can be mutated, for example as N799A, E893A, and/or D1129A, to decrease the catalytic activity of a CasMG1 polypeptide. Thus, in some cases, the CasMG1 protein has reduced activity in one or more of the above described amino acids (or one or more corresponding amino acids of any CasMG1 protein) are mutated (e.g., substituted with an alanine). In some cases, the variant CasMG1 protein is a catalytically 'dead' protein (is catalytically inactive) and is referred to as 'dCasMG1.' A dCasMG1 protein can be fused to a fusion partner that provides an activity, and in some cases, the dCasMG1 (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG1 protein is a nickase (cleaves only one strand of a double stranded target nucleic acid, e.g., a double stranded target DNA). A CasMG1 fusion polypeptide can comprise any of the aforementioned dCasMG1 proteins.

Conserved catalytic residues of CasMG2 include the RuvC subdomain residues identified above. D877, E970, and D1219, numbered according to SEQ ID NO: 59, are residues that can be mutated, for example as D877A, E970A, or D1219A, to decrease the catalytic activity of a CasMG2 polypeptide. Thus, in some cases, the CasMG2 protein has reduced activity in one or more of the above described amino acids (or one or more corresponding amino acids of any CasMG2 protein) are mutated (e.g., substituted with an alanine). In some cases, the variant CasMG2 protein is a catalytically 'dead' protein (is catalytically inactive) and is referred to as 'dCasMG2.' A dCasMG2 protein can be fused to a fusion partner that provides an activity, and in some cases, the dCasMG2 (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG2 protein is a nickase (cleaves only one strand of a double stranded target nucleic acid, e.g., a double stranded target DNA). A CasMG2 fusion polypeptide can comprise any of the aforementioned dCasMG2 proteins.

Conserved catalytic residues of CasMG3 include the RuvC subdomain residues identified above. D848, E933, and D1184 numbered according to SEQ ID NO: 66, are residues that can be mutated, for example as D848A, E933A, or D1184A, to decrease the catalytic activity of a CasMG3 polypeptide. Thus, in some cases, the CasMG3 protein has reduced activity in one or more of the above described amino acids (or one or more corresponding amino acids of any CasMG3 protein) are mutated (e.g., substituted with an alanine). In some cases, the variant CasMG3 protein is a catalytically 'dead' protein (is catalytically inactive) and is referred to as 'dCasMG3.' A dCasMG3 protein can be fused to a fusion partner that provides an activity, and in some cases, the dCasMG3 (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG3 protein is a nickase (cleaves only one strand of a double stranded target nucleic acid, e.g., a double stranded target DNA). A CasMG3 fusion polypeptide can comprise any of the aforementioned dCasMG3 proteins.

Conserved catalytic residues of CasMG4 include the RuvC subdomain residues identified above. D832, E925, and D1175, numbered according to SEQ ID NO: 73, are residues that can be mutated, for example as D832A, E925A, or D1175A, to decrease the catalytic activity of a CasMG4 polypeptide. Thus, in some cases, the CasMG4 protein has reduced activity in one or more of the above described amino acids (or one or more corresponding amino acids of any CasMG4 protein) are mutated (e.g., substituted with an alanine). In some cases, the variant CasMG4 protein is a catalytically 'dead' protein (is catalytically inactive) and is referred to as 'dCasMG4.' A dCasMG4 protein can be fused to a fusion partner that provides an activity, and in some cases, the dCasMG4 (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG4 protein is a nickase (cleaves only one strand of a double stranded target nucleic acid, e.g., a double stranded target DNA). A CasMG4 fusion polypeptide can comprise any of the aforementioned dCasMG4 proteins.

Conserved catalytic residues of CasMG5 include the RuvC subdomain residues identified above. D833, E926, or D1172, numbered according to SEQ ID NO: 80, are residues that can be mutated, for example as D833A, E926A, or D1172A, to decrease the catalytic activity of a CasMG5 polypeptide. Thus, in some cases, the CasMG5 protein has reduced activity in one or more of the above described amino acids (or one or more corresponding amino acids of any CasMG5 protein) are mutated (e.g., substituted with an alanine). In some cases, the variant CasMG5 protein is a catalytically 'dead' protein (is catalytically inactive) and is referred to as 'dCasMG5.' A dCasMG5 protein can be fused to a fusion partner that provides an activity, and in some cases, the dCasMG5 (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG5 protein is a nickase (cleaves only one strand of a double stranded target nucleic acid, e.g., a double stranded target DNA). A CasMG5 fusion polypeptide can comprise any of the aforementioned dCasMG5 proteins.

Conserved catalytic residues of CasMG6 include the RuvC subdomain residues identified above. D836, E934, and D1185, numbered according to SEQ ID NO: 87, are residues that can be mutated, for example as D836A, E934A, or D1185A, to decrease the catalytic activity of a CasMG6 polypeptide. Thus, in some cases, the CasMG6 protein has reduced activity in one or more of the above described amino acids (or one or more corresponding amino acids of any CasMG6 protein) are mutated (e.g., substituted with an alanine). In some cases, the variant CasMG6 protein is a catalytically 'dead' protein (is catalytically inactive) and is referred to as 'dCasMG6.' A dCasMG6 protein can be fused to a fusion partner that provides an activity, and in some cases, the dCasMG6 (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG6 protein is a nickase (cleaves only one strand of a double stranded target nucleic acid, e.g., a double stranded target DNA). A CasMG6 fusion polypeptide can comprise any of the aforementioned dCasMG6 proteins.

Conserved catalytic residues of CasMG7 include the RuvC subdomain residues identified above. D865, E950, and/or D1198, numbered according to SEQ ID NO: 94, are residues that can be mutated, for example as D865A, E950A, and/or D1198A, to decrease the catalytic activity of a CasMG7 polypeptide. Thus, in some cases, the CasMG7 protein has reduced activity in one or more of the above described amino acids (or one or more corresponding amino acids of any CasMG7 protein) are mutated (e.g., substituted with an alanine). In some cases, the variant CasMG7 protein is a catalytically 'dead' protein (is catalytically inactive) and is referred to as 'dCasMG7.' A dCasMG7 protein can be fused to a fusion partner that provides an activity, and in some cases, the dCasMG7 (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG7 protein is a nickase (cleaves only one strand of a double stranded target nucleic acid, e.g., a double stranded target DNA). A CasMG7 fusion polypeptide can comprise any of the aforementioned dCasMG7 proteins.

Conserved catalytic residues of CasMG8 include the RuvC subdomain residues identified above. D827, E916, or D1165, numbered according to SEQ ID NO: 101, are residues that can be mutated, for example as D827A, E916A, or D1165A, to decrease the catalytic activity of a CasMG8 polypeptide. Thus, in some cases, the CasMG8 protein has reduced activity in one or more of the above described amino acids (or one or more corresponding amino acids of any CasMG8 protein) are mutated (e.g., substituted with an alanine). In some cases, the variant CasMG8 protein is a catalytically 'dead' protein (is catalytically inactive) and is referred to as 'dCasMG8.' A dCasMG8 protein can be fused to a fusion partner that provides an activity, and in some cases, the dCasMG8 (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG8 protein is a nickase (cleaves only one strand of a double stranded target nucleic acid, e.g., a double stranded target DNA). A CasMG8 fusion polypeptide can comprise any of the aforementioned dCasMG8 proteins.

Conserved catalytic residues of CasMG9 include the RuvC subdomain residues identified above. D828, E917, and D1167, numbered according to SEQ ID NO: 108, are residues that can be mutated, for example as D828A, E917A, and/or D1167A, to decrease the catalytic activity of a CasMG9 polypeptide. Thus, in some cases, the CasMG9 protein has reduced activity in one or more of the above described amino acids (or one or more corresponding amino acids of any CasMG9 protein) are mutated (e.g., substituted with an alanine). In some cases, the variant CasMG9 protein is a catalytically 'dead' protein (is catalytically inactive) and is referred to as 'dCasMG9.' A dCasMG9 protein can be fused to a fusion partner that provides an activity, and in some cases, the dCasMG9 (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG9 protein is a nickase (cleaves only one strand of a double stranded target nucleic acid, e.g., a double stranded target DNA). A CasMG9 fusion polypeptide can comprise any of the aforementioned dCasMG9 proteins.

Conserved catalytic residues of CasMG10 include the RuvC subdomain residues identified above, I837, E920, and/or S1145, numbered according to SEQ ID NO: 115, are residues that can be mutated, for example as I837A, E920A, or S1145A, to decrease the catalytic activity of a CasMG10 polypeptide. Thus, in some cases, the CasMG10 protein has reduced activity in one or more of the above described amino acids (or one or more corresponding amino acids of any CasMG10 protein) are mutated (e.g., substituted with an alanine). In some cases, the variant CasMG10 protein is a catalytically 'dead' protein (is catalytically inactive) and is referred to as 'dCasMG10.' A dCasMG10 protein can be fused to a fusion partner that provides an activity, and in some cases, the dCasMG10) (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasMG10 protein is a nickase (cleaves only one strand of a double stranded target nucleic acid, e.g., a double stranded target DNA). A CasMG10 fusion polypeptide can comprise any of the aforementioned dCasMG10 proteins.

As noted above, in some cases, a CasMG protein (in some cases a CasMG protein with wild type cleavage activity and in some cases a variant CasMG with reduced cleavage activity, e.g., a dCasMG or a nickase CasMG) is fused (conjugated) to a heterologous polypeptide that has an activity of interest (e.g., a catalytic activity of interest) to form a fusion protein (a chimeric CasMG protein or CasMG fusion polypeptide). A heterologous polypeptide to which a CasMG protein can be fused is referred to herein as a 'fusion partner.

In some cases the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a chimeric CasMG protein or CasMG fusion polypeptide includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric CasMG protein or CasMG fusion polypeptide includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity. SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD) TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain: the Mad mSIN3 interaction domain (SID): the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7. HDAC9, SIRT1, SIRT2, HDAC11, and the like; DNA methylases such as Hhal DNA m5c-methyltransferase (M.Hhal), DNA methyltransferase 1 (DNMT1), DNA methyltransferase 3a (DNMT3a), DNA methyltransferase 3b (DNMT3b), MET1, DRM3 (plants), ZMET2, CMT1. CMT2 (plants), and the like; and periphery recruitment elements such as Lamin A, Lamin B, and the like.

In some cases the fusion partner used in a CasMG fusion polypeptide has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase, M.HhaI), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS 1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y: human immunodeficiency virus type 1 integrase (IN): Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases the fusion partner used in a CasMG fusion polypeptide has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMTIA), euchromatic histone lysine methyltransferase 2 (G9A, also known as KMT1C and EHMT2), SUV39H2, ESET/SETDB 1, and the like, SET1A, SET1B, MLL1 to 5, ASHI, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX. JARID1D/SMCY. UTX. JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HB01/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity. SUMOylating activity, deSUMOylating activity, ribosylation activity, deribosylation activity, myristoylation activity, and demyristoylation activity.

An additional examples of a suitable fusion partners used in a CasMG fusion polypeptide are dihydrofolate reductase (DHFR) destabilization domain (e.g., to generate a chemically controllable chimeric CasMG protein or CasMG fusion polypeptide), and a chloroplast transit peptide. Suitable chloroplast transit peptides (CTPs) include, but are not limited to, CTPs having an amino acid sequence with at least 98%, 99%, or 100% sequence identity to SEQ ID NO: 3, 4, 5, 6, 7, 8, 9, 10, 11, 12, and 13.

In some case, a CasMG fusion polypeptide of the present disclosure comprises: a) a CasMG polypeptide of the present disclosure; and b) a chloroplast transit peptide. Thus, for example, a CRISPR-CasMG complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g., chloroplast).

Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the amino terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

The CasMG polypeptide disclosed herein can further comprise at least one plastid targeting signal peptide, at least one mitochondrial targeting signal peptide, or a signal peptide targeting the CasMG polypeptide to both plastids and mitochondria. Plastid, mitochondrial, and dual-targeting signal peptide localization signals are known in the art (see, e.g., Nassoury and Morse (2005) Biochim Biophys Acta 1743:5-19; Kunze and Berger (2015) Front Physiol dx.doi.org/10.3389/fphys.2015.00259; Herrmann and Neupert (2003) IUBMB Life 55:219-225; Soll (2002) Curr Opin Plant Biol 5:529-535; Carrie and Small (2013) Biochim Biophys Acta 1833:253-259; Carrie et al. (2009) FEBS J 276:1187-1195; Silva-Filho (2003) Curr Opin Plant Biol 6:589-595; Peeters and Small (2001) Biochim Biophys Acta 1541:54-63; Murcha et al. (2014) J Exp Bot 65:6301-6335: Mackenzie (2005) Trends Cell Biol 15:548-554; Glaser et al. (1998) Plant Mol Biol 38:311-338). The plastid, mitochondrial, or dual-targeting signal peptide can be located at the N-terminus, the C-terminus, or in an internal location of the CasMG polypeptide.

In some cases, a CasMG fusion polypeptide of the present disclosure can comprise: a) a CasMG polypeptide of the present disclosure; and b) an endosomal escape peptide (EEP). In some cases, an endosomal escape polypeptide comprises the amino acid sequence of SEQ ID NO: 16 or SEQ ID NO: 17.

For examples of some of the above fusion partners (and more) used in the context of fusions with Cas9. Zinc Finger, and/or TALE proteins (for site specific target nucleic modification, modulation of transcription, and/or target protein modification, e.g., histone modification), see, e.g.: Nomura et al J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et al, Cell. 2013 Jul. 18; 154(2):442-51; Kearns et al. Nat Methods. 2015 May; 12(5):401-3; Mendenhall et al. Nat Biotechnol. 2013 December; 31(12): 1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA, 2003 Jul. 22; 100(15):

8688-91: Tan et al., J Virol. 2006 February; 80(4): 1939-48; Tan et al., Proc Natl Acad Sci USA, 2003 Oct. 14; 100(21): 11997-2002; Papworth et al., Proc Natl Acad Sci USA, 2003 Feb. 18; 100(4): 1621-6; Sanjana et al., Nat Protoc. 2012 Jan. 5; 7(1): 171-92: Beerli et al., Proc Natl Acad Sci USA, 1998 Dec. 8; 95(25): 14628-33; Snowden et al., Curr Biol. 2002 Dec. 23; 12(24):2159-66; Xu et. al., Cell Discov. 2016 May 3; 2: 16009; Komor et al., Nature. 2016 Apr. 20; 533(7603):420-4; Chaikind et al., Nucleic Acids Res. 2016 Aug. 11; Choudhury at. al., Oncotarget. 2016 Jun. 23; Du et al., Cold Spring Harb Protoc. 2016 Jan. 4; Pham et al. Methods Mol Biol. 2016; 1358:43-57; Balboa et al., Stem Cell Reports. 2015 Sep. 8; 5(3):448-59; Hara et al., Sci Rep. 2015 Jun. 9; 5: 11221; Piatek et al., Plant Biotechnol J. 2015 May; 13(4):578-89; Hu et al., Nucleic Acids Res. 2014 April; 42(7):4375-90; Cheng et al., Cell Res. 2013 October; 23(10): 1163-71; Cheng et al, Cell Res. 2013 October; 23(10):1 163-71; and Maeder et al., Nat Methods. 2013 October; 10(10):977-9.

Additional suitable heterologous polypeptides that can be used in a CasMG fusion polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric CasMG polypeptide or CasMG fusion polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include but are not limited to: splicing factors (e.g., RS domains); protein translation components (e.g., translation initiation, elongation, and/or release factors; e.g., eIF4G): RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject chimeric CasMG polypeptide or CasMG fusion polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising: Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP SI, Y14. DEK. REF2, and SRml60); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI DI and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric CasMG polypeptide or CasMG fusion polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example. Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cc-elements that are located in either the core exon region or the exon extension region (i.e., between the two alternative 5' splice sites). For more examples, see WO2010075303, which is hereby incorporated by reference in its entirety.

Further suitable fusion partners or CasMG fusion polypeptide CasMG fusion polypeptide include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pill/Abyl, etc.).

Examples of various additional suitable heterologous polypeptide (or fragments thereof) that can be adapted for use in a subject chimeric CasMG polypeptide or CasMG fusion polypeptide include, but are not limited to those described in the following applications (which publications are related to other CRISPR endonucleases such as Cas9, but the described fusion partners can also be used with CasMG instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) or CasMG fusion polypeptide provides for subcellular localization, e.g., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CasMG fusion polypeptide does not include a NLS so that the protein is not targeted to the nucleus (which can be advantageous, e.g., when the target nucleic acid is an RNA that is present in the cytosol). In some embodiments, the heterologous polypeptide can provide a tag (e.g., the heterologous polypeptide is a detectable label) for ease of tracking and/or purification (e.g., a fluorescent protein, e.g., green fluorescent protein (GFP), YFP, RFP, CFP, mCherry, tdTomato, mScarlett, and the like: a histidine tag, e.g., a 6×His tag; a hemagglutinin (HA) tag; a FLAG tag; a Myc tag; and the like).

In some cases a CasMG protein (e.g., a wild type CasMG protein, a variant CasMG protein, a chimeric CasMG protein. CasMG fusion polypeptide, a dCasMG protein, a chimeric CasMG protein or CasMG fusion polypeptide where the CasMG portion has reduced nuclease activity— such as a dCasMG protein fused to a fusion partner, and the like) includes (is fused to) a nuclear localization signal (NLS) (e.g, in some cases 2 or more, 3 or more, 4 or more, or 5 or more NLSs). Thus, in some cases, a CasMG polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more. 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a CasMG protein (e.g., a wild type CasMG protein, a variant CasMG protein, a chimeric CasMG protein, or CasMG fusion polypeptide, a dCasMG protein, a chimeric CasMG protein or CasMG fusion polypeptide where the CasMG portion has reduced nuclease activity-such as a dCasMG protein fused to a fusion partner, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a CasMG protein (e.g., a wild type CasMG protein, a variant CasMG protein, a chimeric CasMG protein, a dCasMG protein, a chimeric CasMG protein or CasMG fusion polypeptide where the CasMG portion has reduced nuclease activity-such as a dCasMG protein fused to a fusion partner, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence of SEQ ID NO: 57; the NLS from nucleoplasmin (e.g., the nucleoplasmin bipartite NLS with the sequence of SEQ ID NO: 18); the c-myc NLS having the amino acid sequence of SEQ ID NO: 19 or SEQ ID NO: 20; the hRNPA1 M9 NLS having the sequence of SEQ ID NO: 21: the sequence of SEQ ID NO: 22 of the IBB domain from importin-alpha: the sequences of SEQ ID NO: 23 or SEQ ID NO: 24 of the myoma T protein: the sequence of SEQ ID NO: 25 of human p53: the sequence of SEQ ID NO: 26 of mouse c-abl IV: the sequences of SEQ ID NO: 27 or SEQ ID NO: 28 of the influenza virus NS1; the sequence of SEQ ID NO: 29 of the Hepatitis virus delta antigen: the sequence of SEQ ID NO: 30 of the mouse Mxl protein: the sequence of SEQ ID NO: 31 of the human poly(ADP-ribose) polymerase; and the sequence of SEQ ID NO: 32 of a steroid hormone receptor (e.g., human glucocorticoid receptor). In general. NLS (or multiple NLSs) are of sufficient strength to drive accumulation of the CasMG protein in a detectable amount in the nucleus of a eukaryotic cell. Detection of accumulation in the nucleus may be performed by any suitable technique. For example, a detectable marker may be fused to the CasMG protein such that location within a cell may be visualized. Cell nuclei may also be isolated from cells, the contents of which may then be analyzed by any suitable process for detecting protein, such as immunohistochemistry. Western blot, or enzyme activity assay. Accumulation in the nucleus may also be determined indirectly.

In some cases, a CasMG fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type CasMG to generate a fusion protein, or linked to a variant CasMG protein such as a dCasMG, nickase CasMG, or chimeric CasMG protein or CasMG fusion polypeptide to generate a fusion protein). In some embodiments, a PTD is covalently linked to the carboxyl terminus of a polypeptide (e.g., linked to a wild type CasMG to generate a fusion protein, or linked to a variant CasMG protein such as a dCasMG, nickase CasMG, or chimeric CasMG protein or CasMG fusion polypeptide to generate a fusion protein). In some cases, the PTD is inserted internally in the CasMG fusion polypeptide (i.e., is not at the N- or C-terminus of the CasMG fusion polypeptide) at a suitable insertion site. In some cases, a subject CasMG fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a CasMG fusion polypeptide includes one or more NLSs (e.g., 2 or more, 3 or more, 4 or more, or 5 or more NLSs). In some embodiments, a PTD is covalently linked to a nucleic acid (e.g., a CasMG guide nucleic acid, a polynucleotide encoding a CasMG guide nucleic acid, a polynucleotide encoding a CasMG1 fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR (SEQ ID NO: 33); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7): 1732-1737); a truncated human calcitonin peptide (Trehin et al. (2004) Pharm. Research 21: 1248-1256); polylysine (Wender et al. (2000) Proc. Natl. Acad. Sci. USA 97: 13003-13008); RRQRRTSKLMKR (SEQ ID NO: 34); Transportan (e.g., SEQ ID NO: 35, SEQ ID NO: 36, or SEQ ID NO: 37). Exemplary PTDs include but are not limited to, SEQ ID NO: 38, SEQ ID NO: 39; an arginine homopolymer of from 3 arginine residues to 50) arginine residues; Exemplary PTD domain amino acid sequences include, but are not limited to, any of the following: SEQ ID NO: 40; SEQ ID NO: 41; SEQ ID NO: 42: SEQ ID NO: 43; and SEQ ID NO: 44. In some embodiments, the PTD is an activatable CPP (ACPP) (Aguilera et al. (2009) Integr Biol (Camb) June; 1 (5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

In some embodiments, a subject CasMG protein can fused to a fusion partner via a linker polypeptide (e.g., one or more linker polypeptides). The linker polypeptide may have any of a variety of amino acid sequences, Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers (G) n, glycine-serine polymers (including, for example, $(GS)_n$, $GSGGS_n$ (SEQ ID NO: 45), $GGSGGS_n$ (SEQ ID NO: 46), and $GGGS_n$ (SEQ ID NO: 47), where n is an integer of at least one), glycine-alanine polymers, alanine-serine polymers. Exemplary linkers can comprise amino acid sequences including, but not limited to, the amino acid sequences of SEQ ID NO: 48, SEQ ID NO: 49, SEQ ID NO: 50. SEQ ID NO: 51, SEQ ID NO: 52, SEQ ID NO: 53, and the like. The ordinarily skilled artisan will recognize that design of a peptide conjugated to any desired element can include linkers that are all or partially flexible, such that the linker can include a flexible linker as well as one or more portions that confer less flexible structure.

In some cases, a CasMG polypeptide or CasMG fusion polypeptide of the present disclosure comprises a detectable label. Suitable detectable labels and/or moieties that can provide a detectable signal can include, but are not limited to, an enzyme, a radioisotope, a member of a specific binding pair: a fluorophore: a fluorescent protein: a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2 (12), mRFPl, pocilloporin, *Renilla* GFP, Monster GFP, paGFP, Kaede protein and kindling protein. Phycobiliproteins and Phycobiliprotein conjugates including B-Phycoerythrin. R-Phycoerythrin and Allophycocyanin. Other examples of fluorescent proteins include mHoneydew, mBanana, mOrange, dTomato, tdTomato, mScarlett, mTangerine, mStrawberry, mCherry, mGrapel, mRaspberry, mGrape2, mPlum (Shaner et al. (2005) Nat. Methods 2:905-909), and the like. Any of a variety of fluorescent and colored proteins from Anthozoan species, as described in, e.g., Matz et al. (1999) Nature Biotechnol. 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase. Xanthine Oxidase, firefly luciferase, glucose oxidase (GO), and the like.

A CasMG protein binds to target DNA at a target sequence defined by the region of complementarity between the DNA-targeting RNA and the target DNA, As is the case for many CRISPR endonucleases, site-specific binding (and/or cleavage) of a double stranded target DNA occurs at locations determined by both (i) base-pairing complementarity between the guide RNA and the target DNA; and (ii) a short motif, referred to as the protospacer adjacent motif (PAM), in the target DNA.

In some embodiments, the PAM for a CasMG protein is immediately 5' of the target sequence of the non-complementary strand of the target DNA (the complementary strand hybridizes to the guide sequence of the guide RNA while the non-complementary strand does not directly hybridize with the guide RNA and is the reverse complement of the complementary strand). In some embodiments (e.g., when CasMG as described herein is used), the PAM consensus sequence of the non-complementary strand is T-rich. Examples of PAM sequences include, but are not limited to, TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide).

In some cases, different CasMG proteins (e.g., CasMG proteins from various species) may be advantageous to use in the various provided methods in order to capitalize on various enzymatic characteristics of the different CasMG proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like), CasMG proteins may require different PAM sequences in the target DNA, Thus, for a particular CasMG protein of choice, the PAM sequence requirement may be different than the T-rich sequence described above. Various methods (including in silico and/or wet lab methods) for identification of the appropriate PAM sequence are known in the art and are routine, and any convenient method can be used. A PAM sequence can be identified using a PAM depletion assay.

A nucleic acid molecule that binds to a CasMG protein, forming a ribonucleoprotein complex (RNP), and targets the complex to a specific location within a target nucleic acid (e.g., a target DNA) is referred to herein as a "CasMG guide RNA" or simply as a "guide RNA," It is to be understood that in some cases, a hybrid DNA/RNA can be made such that a CasMG guide RNA includes DNA bases in addition to RNA bases, but the term "CasMG guide RNA" is still used to encompass such a molecule herein.

A CasMG guide RNA can be said to include two segments, a targeting segment and a protein-binding segment. The targeting segment of a CasMG guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). Site-specific binding and/or cleavage of a target nucleic acid (e.g., genomic DNA) can occur at locations (e.g., target sequence of a target locus) determined by base-pairing complementarity between the CasMG guide RNA (the guide sequence of the CasMG guide RNA) and the target nucleic acid.

The protein-binding segment (or "protein-binding sequence") interacts with (binds to) a CasMG polypeptide.

In some cases the protein-binding segment is made up of a short sequence of 17-20 nucleotides, such as a sequence of 18 or 19 nucleotides. This protein binding segment forms a double-stranded RNA duplex of five paired residues in length. The 5' terminus has about three residues upstream from the first RNA duplexed residue. A stem structure of 4-5 residues separates the double stranded regions. A CasMG1 protein binding segment can be made up, for example, of an RNA encoded by residues 16-36 of SEQ ID NO: 2 (i.e., an RNA encoded by SEQ ID NO: 15). A CasMG2 protein binding segment can be made up, for example, of an RNA encoded by residues 18-36 of SEQ ID NO: 60 (i.e., an RNA encoded by SEQ ID NO: 62). A CasMG3 protein binding segment can be made up, for example, of an RNA encoded by residues 18-36 of SEQ ID NO: 67 (i.e., an RNA encoded by SEQ ID NO: 69). A CasMG4 protein binding segment can be made up, for example, of an RNA encoded by residues 18-36 of SEQ ID NO: 74 (i.e., an RNA encoded by SEQ ID NO: 76). A CasMG5 protein binding segment can be made up, for example, of an RNA encoded by residues 18-36 of SEQ ID NO: 81 (i.e., an RNA encoded by SEQ ID NO: 83). A CasMG6 protein binding segment can be made up, for example, of an RNA encoded by residues 18-36 of SEQ ID NO: 88 (i.e., an RNA encoded by SEQ ID NO: 90). A CasMG7 protein binding segment can be made up, for example, of an RNA encoded by residues 18-36 of SEQ ID NO: 95 (i.e., an RNA encoded by SEQ ID NO: 97). A CasMG8 protein binding segment can be made up, for example, of an RNA encoded by residues 18-36 of SEQ ID NO: 102 (i.e., an RNA encoded by SEQ ID NO: 104). A CasMG9 protein binding segment can be made up, for example, of an RNA encoded by residues 18-36 of SEQ ID NO: 109 (i.e., an RNA encoded by SEQ ID NO: 111). A CasMG10 protein binding segment can be made up, for example, of an RNA encoded by residues 17-36 of SEQ ID NO: 116 (i.e., an RNA encoded by SEQ ID NO: 118).

In some cases the protein-binding segment of a subject CasMG guide RNA includes two complementary stretches of nucleotides that hybridize to one another to form a double stranded RNA duplex (dsRNA duplex).

A CasMG guide RNA and a CasMG protein, e.g., a fusion CasMG polypeptide, form a complex (e.g., bind via non-covalent interactions). The CasMG guide RNA provides target specificity to the complex by including a targeting segment, which includes a guide sequence (a nucleotide sequence that is complementary to a sequence of a target nucleic acid). The CasMG protein of the complex provides the site-specific activity (e.g., cleavage activity provided by the CasMG protein or CasMG fusion polypeptide and/or an activity provided by the fusion partner in the case of a chimeric CasMG protein or CasMG fusion polypeptide). In other words, the CasMG protein is guided to a target nucleic acid sequence (e.g., a target sequence) by virtue of its association with the CasMG guide RNA.

The "guide sequence" also referred to as the "targeting sequence" of a CasMG guide RNA can be made so that the CasMG guide RNA can target a CasMG protein (e.g., a naturally-occurring CasMG protein, a fusion CasMG polypeptide (chimeric CasMG), and the like) to any desired sequence of any desired target nucleic acid, with the exception (e.g., as described herein) that the PAM sequence can be taken into account. Thus, for example, a CasMG guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments a subject CasMG guide RNA can also be said to include an "activator" and a "targeter" (e.g., an "activator-RNA" and a "targeter-RNA," respectively). When the "activator" and a "targeter" are two separate molecules the guide RNA is referred to herein as a "dual guide RNA", a "dgRNA," a "double-molecule guide RNA", or a "two-molecule guide RNA," (e.g., a "CasMG dual guide RNA"). In some embodiments, the activator and targeter are covalently linked to one another (e.g., via intervening nucleotides) and the guide RNA is referred to herein as a "single guide RNA", an "sgRNA," a "single-molecule guide RNA," or a "one-molecule guide RNA" (e.g., a "CasMG single guide RNA"). Thus, a subject CasMG single guide RNA comprises a targeter (e.g., targeter-RNA) and an activator (e.g., activator-RNA) that are linked to one another (e.g., by intervening nucleotides), and may hybridize to one another to form the double stranded RNA duplex (dsRNA duplex) of the protein-binding segment of the guide RNA, thus resulting in a stem-loop structure. Thus, the targeter and the activator each have a duplex-forming segment, where the duplex forming segment of the targeter and the duplex-forming segment of the activator have complementarity with one another and hybridize to one another.

In some embodiments, the linker of a CasMG single guide RNA is a stretch of nucleotides. In some cases, the targeter and activator of a CasMG single guide RNA are linked to one another by intervening nucleotides and the linker can have a length of from 3 to 20 nucleotides (nt) (e.g., from 3 to 15, 3 to 12, 3 to 10, 3 to 8, 3 to 6, 3 to 5, 3 to 4, 4 to 20, 4 to 15, 4 to 12, 4 to 10, 4 to 8, 4 to 6, or 4 to 5 nt). In some embodiments, the linker of a CasMG single guide RNA can have a length of from 3 to 100 nucleotides (nt) (e.g., from 3 to 80, 3 to 50, 3 to 30, 3 to 25, 3 to 20, 3 to 15, 3 to 12, 3 to 10, 3 to 8, 3 to 6, 3 to 5, 3 to 4, 4 to 100, 4 to 80, 4 to 50, 4 to 30, 4 to 25, 4 to 20, 4 to 15, 4 to 12, 4 to 10, 4 to 8, 4 to 6, or 4 to 5 nt). In some embodiments, the linker of a CasMG single guide RNA can have a length of from 3 to 10 nucleotides (nt) (e.g., from 3 to 9, 3 to 8, 3 to 7, 3 to 6, 3 to 5, 3 to 4, 4 to 10, 4 to 9, 4 to 8, 4 to 7, 4 to 6, or 4 to 5 nt).

The targeting segment of a subject CasMG guide RNA includes a guide sequence (i.e., a targeting sequence), which is a nucleotide sequence that is complementary to a sequence (a target site) in a target nucleic acid. In other words, the targeting segment of a CasMG guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CasMG guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some embodiments, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more, 23 or more, 24 or more, 25 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more, 23 or more, 24 or more, 25 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more, 23 or more, 24 or more, 25 or more) contiguous nucleotides. In some cases, the percent complementarity between the guide sequence and the target site of the target nucleic acid is 100% over 19 or more (e.g., 20 or more, 21 or more, 22 or more, 23 or more, 24 or more, 25 or more) contiguous nucleotides.

In some cases, the guide sequence has a length in a range of from 19-30 nucleotides (e.g., from 19-25, 19-22, 19-20, 20-30, 20-25, or 20-22 nt). In some cases, the guide sequence has a length in a range of from 19-25 nucleotides (e.g., from 19-22, 19-20, 20-25, 20-25, or 20-22 nt). In some cases, the guide sequence has a length of 19 or more nt (e.g., 20 or more, 21 or more, or 22 or more nt: 19 nt, 20 nt, 21 nt, 22 nt, 23 nt, 24 nt, 25 nt, etc.). In some cases the guide sequence has a length of 17 nt. In some cases the guide sequence has a length of 18 nt. In some cases the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

The protein-binding segment of a subject CasMG guide RNA interacts with a CasMG protein. The CasMG guide RNA guides the bound CasMG protein to a specific nucleotide sequence within target nucleic acid via the above mentioned guide sequence. In some embodiments, the protein-binding segment of a CasMG guide RNA comprises two stretches of nucleotides (the duplex-forming segment of the activator and the duplex-forming segment of the targeter) that are complementary to one another and hybridize to form a double stranded RNA duplex (dsRNA duplex). Thus, the protein-binding segment includes a dsRNA duplex.

The duplex region of a subject CasMG guide RNA (in dual guide or single guide RNA format) can include one or more (1, 2, 3, 4, 5, etc) mutations relative to a naturally-occurring duplex region. For example, in some cases a base pair can be maintained while the nucleotides contributing to the base pair from each segment (targeter and activator) can be different. In some cases, the duplex region of a subject CasMG guide RNA includes more paired bases, less paired bases, a smaller bulge, a larger bulge, fewer bulges, more bulges, or any convenient combination thereof, as compared to a naturally-occurring duplex region (of a naturally-occurring CasMG guide RNA).

In some cases, the activator (e.g., activator-RNA) of a subject CasMG guide RNA (in dual or single guide RNA format) includes at least two internal RNA duplexes (i.e., two internal hairpins in addition to the activator/targeter dsRNA). The internal RNA duplexes (hairpins) of the activator can be positioned 5' of the activator/targeter dsRNA duplex. In some cases, the activator includes one hairpin positioned 5' of the activator/targeter dsRNA duplex. In some cases, the activator includes two hairpins positioned 5' of the activator/targeter dsRNA duplex. In some cases, the activator includes three hairpins positioned 5' of the activator/targeter dsRNA duplex. In some cases, the activator includes two or more hairpins (e.g., 3 or more or 4 or more hairpins) positioned 5' of the activator/targeter dsRNA duplex. In some cases, the activator includes 2 to 5 hairpins (e.g., 2 to 4, or 2 to 3 hairpins) positioned 5' of the activator/targeter dsRNA duplex.

In some cases, the activator-RNA (e.g., in dual or single guide RNA format) comprises at least 2 nucleotides (nt) (e.g., at least 3 or at least 4 nt) 5' of the 5'-most hairpin stem. In some cases, the activator-RNA (e.g., in dual or single guide RNA format) comprises at least 4 nt 5' of the 5'-most hairpin stem.

In some cases, the activator-RNA (e.g., in dual or single guide format) includes 45 or more nucleotides (nt) (e.g., 46 or more, 47 or more, 48 or more, 49 or more, 50 or more, 51 or more, 52 or more, 53 or more, 54 or more, or 55 or more nt) 5' of the dsRNA duplex formed between the activator and the targeter (the activator/targeter dsRNA duplex). In some cases, the activator is truncated at the 5' end relative to a naturally-occurring CasMG activator. In some cases, the activator is extended at the 5' end relative to a naturally-occurring CasMG activator.

In some cases, the term "activator" or "activator RNA" is used herein to mean a tracrRNA-like molecule (tracrRNA; "trans-acting CRISPR RNA") of a CasMG dual guide RNA (and therefore of a CasMG single guide RNA when the "activator" and the "targeter" are linked together by, e.g., intervening nucleotides). Thus, for example, a CasMG guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a CasMG dual guide RNA. A tracrRNA of the CasMG1 locus is shown as SEQ ID NO: 14. A tracrRNA of the CasMG2 locus is shown as SEQ ID NO: 61. A tracrRNA of the CasMG3 locus is shown as SEQ ID NO: 68. A tracrRNA of the CasMG4 locus is shown as SEQ ID NO: 75. A tracrRNA of the CasMG5 locus is shown as SEQ ID NO: 82. A tracrRNA of the CasMG6 locus is shown as SEQ ID NO: 89. A tracrRNA of the CasMG7 locus is shown as SEQ ID NO: 96. A tracrRNA of the CasMG8 locus is shown as SEQ ID NO: 103. A tracrRNA of the CasMG9 locus is shown as SEQ ID NO: 110. A tracrRNA of the CasMG10 locus is shown as SEQ ID NO: 117. The term "activator" is used herein to encompass naturally-occurring tracrRNAs, but also to encompass tracrRNAs with modifications (e.g., truncations, extensions, sequence variations, base modifications, backbone modifications, linkage modifications, etc.) where the activator retains at least one function of a tracrRNA (e.g., contributes to the dsRNA duplex to which CasMG protein binds). In some cases the activator provides one or more stem loops that can interact with CasMG protein. An activator can be referred to as having a tracr sequence (tracrRNA sequence) and in some cases is a tracrRNA, but the term "activator" is not limited to naturally-occurring tracrRNAs.

In some cases (e.g., in some cases where the guide RNA is in single guide format), the activator-RNA is truncated (shorter) relative to the corresponding wild type tracrRNA, In some cases (e.g., in some cases where the guide RNA is in single guide format) the activator-RNA is not truncated (shorter) relative to the corresponding wild type tracrRNA, In some cases (e.g., in some cases where the guide RNA is in single guide format) the activator-RNA has a length that is greater than 50 nt (e.g., greater than 55 nt, greater than 60 nt, greater than 65 nt, greater than 70 nt, greater than 75 nt, greater than 80 nt). In some cases (e.g., in some cases where the guide RNA is in single guide format) the activator-RNA has a length that is greater than 80 nt. In some cases (e.g., in some cases where the guide RNA is in single guide format) the activator-RNA has a length in a range of from 51 to 90 nt (e.g., from 51-85, 51-84, 55-90, 55-85, 55-84, 60-90, 60-85, 60-84, 65-90, 65-85, 65-84, 70-90, 70-85, 70-84, 75-90, 75-85, 75-84, 80-90, 80-85, or 80-84 nt). In some cases (e.g., in some cases where the guide RNA is in single guide format) the activator-RNA has a length in a range of from 80-90 nt.

The term "targeter" or "targeter RNA" is used herein to refer to a crRNA-like molecule (crRNA; "CRISPR RNA" or CR) of a CasMG dual guide RNA (and therefore of a CasMG single guide RNA when the "activator" and the "targeter" are linked together, e.g., by intervening nucleotides). Thus, for example, a CasMG guide RNA (dgRNA or sgRNA) comprises a guide sequences and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally-occurring sequence. However, the duplex-forming segment of a targeter (described in more detail herein), which hybridizes with the duplex-forming segment of an activator, can include a naturally-occurring sequence (e.g., can include the sequence of a duplex-forming segment of a naturally-occurring crRNA, which can also be referred to as a crRNA repeat). Thus, the term targeter is used herein to distinguish from naturally occurring crRNAs, despite the fact that part of a targeter (e.g., the duplex-forming segment) often includes a naturally-occurring sequence from a crRNA, However, the term "targeter" encompasses naturally-occurring crRNAs.

As noted above, a targeter comprises both the guide sequence of the CasMG guide RNA and a stretch (a "duplex-forming segment") of nucleotides that forms one half of the dsRNA duplex of the protein-binding segment of the CasMG guide RNA, A corresponding tracrRNA-like molecule (activator) comprises a stretch of nucleotides (a duplex-forming segment) that forms the other half of the dsRNA duplex of the protein-binding segment of the CasMG guide RNA, In other words, a stretch of nucleotides of the targeter is complementary to and hybridizes with a stretch of nucleotides of the activator to form the dsRNA duplex of the protein-binding segment of a CasMG guide RNA, As such, each targeter can be said to have a corresponding activator (which has a region that hybridizes with the targeter). The targeter molecule additionally provides the guide sequence. Thus, a targeter and an activator (as a corresponding pair) hybridize to form a CasMG guide RNA, The particular sequence of a given naturally-occurring crRNA or tracrRNA molecule can be characteristic of the species in which the RNA molecules are found.

The present disclosure provides an engineered, non-naturally-occurring CasMG system, for example, an engineered, non-naturally occurring CasMG1, CasMG2, CasMG3, CasMG4, CasMG5, CasMG6, CasMG7, CasMG8, CasMG9, or CasMG10 system. In certain embodiments, a CasMG system of the present disclosure can comprise: a) a CasMG polypeptide of the present disclosure and a CasMG guide RNA; b) a CasMG polypeptide of the present disclosure, a CasMG guide RNA, and a donor template nucleic acid; c) a CasMG fusion polypeptide of the present disclosure and a CasMG guide RNA; d) a CasMG fusion polypeptide of the present disclosure, a CasMG guide RNA, and a donor template nucleic acid; e) an mRNA encoding a CasMG polypeptide of the present disclosure; and a CasMG guide RNA; f) an mRNA encoding a CasMG polypeptide of the present disclosure, a CasMG guide RNA, and a donor template nucleic acid; g) an mRNA encoding a CasMG fusion polypeptide of the present disclosure; and a CasMG guide RNA; h) an mRNA encoding a CasMG fusion polypeptide of the present disclosure, a CasMG guide RNA, and a donor template nucleic acid; i) a recombinant expression vector comprising a nucleotide sequence encoding a CasMG polypeptide of the present disclosure and a nucleotide sequence encoding a CasMG guide RNA; j) a recombinant expression vector comprising a nucleotide sequence encoding a CasMG polypeptide of the present disclosure, a nucleotide sequence encoding a CasMG guide RNA, and a nucleotide sequence encoding a donor template nucleic acid; k) a recombinant expression vector comprising a nucleotide sequence encoding a CasMG fusion polypeptide of the present disclosure and a nucleotide sequence encoding a CasMG guide RNA; l) a recombinant expression vector comprising a nucleotide sequence encoding a CasMG fusion polypeptide of the present disclosure, a nucleotide sequence encoding a CasMG guide RNA, and a nucleotide sequence encoding a donor template nucleic acid; m) a first recombinant expression vector comprising a nucleotide sequence encoding a CasMG polypeptide of the present disclosure, and a second recombinant expression vector comprising a nucleotide sequence encoding a CasMG guide RNA; n) a first recombinant expression vector comprising a nucleotide sequence encoding a CasMG polypeptide of the present disclosure, and a second recombinant expression vector comprising a nucleotide sequence encoding a CasMG guide RNA; and a donor template nucleic acid; o) a first recombinant expression vector comprising a nucleotide sequence encoding a CasMG fusion polypeptide of the present disclosure, and a second recombinant expression vector comprising a nucleotide sequence encoding a CasMG guide RNA; p) a first recombinant expression vector comprising a nucleotide sequence encoding a CasMG fusion polypeptide of the present disclosure, and a second recombinant expression vector comprising a nucleotide sequence encoding a CasMG guide RNA; and a donor template nucleic acid; q) a recombinant expression vector comprising a nucleotide sequence encoding a CasMG polypeptide of the present disclosure, a nucleotide sequence encoding a first CasMG guide RNA, and a nucleotide sequence encoding a second CasMG guide RNA; or r) a recombinant expression vector comprising a nucleotide sequence encoding a CasMG fusion polypeptide of the present disclosure, a nucleotide sequence encoding a first CasMG guide RNA, and a nucleotide sequence encoding a second CasMG guide RNA; or some variation of one of (a) through (r).

The present disclosure provides one or more nucleic acids comprising one or more of: a donor polynucleotide sequence, a nucleotide sequence encoding a CasMG polypeptide of this disclosure (e.g., a wild type CasMG protein, a nickase CasMG protein, a dCasMG protein, chimeric CasMG protein. CasMG fusion polypeptide, and the like), a CasMG guide RNA, and a nucleotide sequence encoding a CasMG guide RNA (which can include two separate nucleotide sequences in the case of dual guide RNA format or which can include a single nucleotide sequence in the case of single guide RNA format). The present disclosure provides a nucleic acid comprising a nucleotide sequence encoding a CasMG fusion polypeptide. The present disclosure provides a recombinant expression vector that comprises a nucleotide sequence encoding a CasMG polypeptide. The present disclosure provides a recombinant expression vector that comprises a nucleotide sequence encoding a CasMG fusion polypeptide. The present disclosure provides a recombinant expression vector that comprises: a) a nucleotide sequence encoding a CasMG polypeptide; and b) a nucleotide sequence encoding a CasMG guide RNA(s). The present disclosure provides a recombinant expression vector that comprises: a) a nucleotide sequence encoding a CasMG fusion polypeptide; and b) a nucleotide sequence encoding a CasMG guide RNA(s). In some cases, the nucleotide sequence encoding the CasMG1 protein and/or the nucleotide sequence encoding the CasMG guide RNA is operably linked to a promoter that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding a CasMG polypeptide of the present disclosure is codon optimized. This type of optimization can entail a mutation of a CasMG-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized CasMG-encoding nucleotide sequence could be used. As another non-limiting example, if the intended host cell were a mouse cell, then a mouse codon-optimized CasMG-encoding nucleotide sequence could be generated. As another non-limiting example, if the intended host cell were a plant cell, then a plant codon-optimized CasMG-encoding nucleotide sequence could be generated. As another non-limiting example, if the intended host cell were an insect cell, then an insect codon-optimized CasMG-encoding nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a CasMG guide RNA that hybridizes to a target sequence of the target locus of the targeted genome (e.g., a single or dual guide RNA) (e.g., operably linked to a promoter that is operable in a target cell such as a eukaryotic cell); and (iii) a nucleotide sequence encoding a CasMG protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a CasMG guide RNA that hybridizes to a target sequence of the target locus of the targeted genome (e.g., a single or dual guide RNA) (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a CasMG guide RNA that hybridizes to a target sequence of the target locus of the targeted genome (e.g., a single or dual guide RNA) (e.g., operably linked to a promoter that is operable in a target cell such as a eukaryotic cell); and (ii) a nucleotide sequence encoding a CasMG protein (e.g., operably linked to a promoter that is operable in a target cell such as a eukaryotic cell).

Suitable expression vectors include viral expression vectors (e.g., viral vectors based on vaccinia virus; poliovirus; adenovirus (see, e.g., Li et al., Invest Opthalmol Vis Sci 35:2543 2549, 1994; Borras et al. Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166: 154-165; and Flotte et al., PNAS (1993) 90; 10613-10617); SV40; herpes simplex virus; human immunodeficiency virus (see, e.g., Miyoshi et al., PNAS 94: 10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc, may be used in the expression vector.

In some embodiments, a nucleotide sequence encoding a CasMG guide RNA is operably linked to a control element, e.g., a transcriptional control element, such as a promoter. In some embodiments, a nucleotide sequence encoding a CasMG protein or a CasMG1 fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34 (+) cell, bone marrow (BM) CD34 (+) cell, etc.).

Nonlimiting examples of eukaryotic promoters (promoters functional in a eukaryotic cell) include EF1a, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the CasMG protein, thus resulting in a chimeric CasMG polypeptide or CasMG fusion polypeptide.

In some embodiments, a nucleotide sequence encoding a CasMG guide RNA and/or a CasMG fusion polypeptide is operably linked to an inducible promoter. In some embodiments, a nucleotide sequence encoding a CasMG guide RNA and/or a CasMG fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (e.g., transcriptional control element, enhancer, etc.) (e.g., tissue specific promoter, cell type specific promoter, etc.), and it may be a temporally restricted promoter (e.g., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6)

(Miyagishi et al., Nature Biotechnology 20, 497-500 (2002)), an enhanced U6 promoter (e.g., Xia et al., Nucleic Acids Res. 2003 Sep. 1; 31 (17)), a human HI promoter (HI), and the like.

In some cases, a nucleotide sequence encoding a CasMG guide RNA is operably linked to (under the control of) a promoter operable in a eukaryotic cell (e.g., a U6 promoter, an enhanced U6 promoter, an HI promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA (e.g., the activator portion and/or targeter portion, in dual guide or single guide format) in a eukaryotic cell it may sometimes be necessary to modify the sequence encoding the guide RNA to eliminate runs of Ts. In some cases, a nucleotide sequence encoding a CasMG protein (e.g., a wild type CasMG protein, a nickase CasMG protein, a dCasMG protein, a chimeric CasMG protein. CasMG fusion polypeptide, and the like) is operably linked to a promoter operable in a eukaryotic cell (e.g., a CMV promoter, an EF1a promoter, an estrogen receptor-regulated promoter, and the like).

Examples of inducible promoters include, but are not limited to T7 RNA polymerase promoter, T3 RNA polymerase promoter. Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline: estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (e.g., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell). In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a CasMG protein and/or a CasMG guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a CasMG protein can be provided as RNA, The RNA can be provided by direct chemical synthesis or may be transcribed in vitro from a DNA (e.g., encoding the CasMG protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g., Angel and Yanik (2010) PLOS ONE 5 (7): el 1756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) PNAS 105(50): 19821-19826.

Vectors may be provided directly to a target host cell. In other words, the cells are contacted with vectors comprising the subject nucleic acids (e.g., recombinant expression vectors having the donor template sequence and encoding the CasMG guide RNA; recombinant expression vectors encoding the CasMG protein: etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", e.g., unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat: amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CasMG guide RNA and/or a CasMG polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV—actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CasMG guide RNA and/or a CasMG protein to a cell may include nucleic acid sequences that encode for selectable markers in the target cells, so as to identify cells that have taken up the CasMG guide RNA and/or CasMG protein.

A nucleic acid comprising a nucleotide sequence encoding a CasMG polypeptide, or a CasMG fusion polypeptide, is in some cases an RNA, Thus, a CasMG fusion protein can be introduced into cells as RNA, Methods of introducing RNA into cells are known in the art and may include, for example, direct injection, transfection, or any other method used for the introduction of DNA, A CasMG protein may instead be provided to cells as a polypeptide. Such a polypeptide may optionally be fused to a polypeptide domain that increases solubility of the product. The domain may be linked to the polypeptide through a defined protease cleavage site, e.g., a TEV sequence, which is cleaved by TEV protease. The linker may also include one or more flexible sequences, e.g., from 1 to 10 glycine residues. In some embodiments, the cleavage of the fusion protein is performed in a buffer that maintains solubility of the product, e.g., in the presence of from 0.5 to 2 M urea, in the presence of polypeptides and/or polynucleotides that increase solubility, and the like. Domains of interest include endosomolytic domains, e.g, influenza HA domain; and other polypeptides that aid in production, e.g., IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a CasMG polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence of SEQ ID NO: 58. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24): 13003-8; published U.S. Patent Applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CasMG polypeptide of the present disclosure may be produced in vitro or by eukaryotic cells or by prokaryotic cells, and it may be further processed by unfolding, e.g., heat denaturation, dithiothreitol reduction, etc, and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g., those made by modifying the glycosylation patterns of a polypeptide during its synthesis and processing or in further processing steps; e.g., by exposing the polypeptide to enzymes which affect glycosylation, such as mammalian glycosylating or deglycosylating enzymes. Also embraced are sequences that have phosphorylated amino acid residues, e.g., phosphotyrosine, phosphoserine, or phosphothreonine.

Also suitable for inclusion in embodiments of the present disclosure are nucleic acids (e.g., encoding a CasMG guide RNA, encoding a CasMG fusion protein, etc.) and proteins (e.g., a CasMG fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally-occurring L-amino acids, e.g., D-amino acids or non-naturally-occurring synthetic amino acids. D-amino acids may be substituted for some or all of the amino acid residues.

A CasMG polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally-occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CasMG polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CasMG polypeptide, or a CasMG fusion polypeptide, of the present disclosure is at least 80% pure, at least 85% pure, at least 90% pure, at least 95% pure, at least 98% pure, or at least 99% pure (e.g., free of contaminants, non-CasMG proteins or other macromolecules, etc.).

To induce cleavage or any desired modification to a target nucleic acid (e.g., genomic DNA), or any desired modification to a polypeptide associated with target nucleic acid, the CasMG guide RNA and/or the CasMG polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20) hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g., one time, twice, three times, or more than three times, and the cells allowed to incubate with the agent(s) for some amount of time following each contacting event e.g., 16-24 hours, after which time the media is replaced with fresh media and the cells are cultured further.

In cases in which two or more different targeting complexes are provided to the cell (e.g., two different CasMG guide RNAs that are complementary to different sequences within the same or different target nucleic acid), the complexes may be provided simultaneously (e.g., as two polypeptides and/or nucleic acids), or delivered simultaneously. Alternatively, they may be provided consecutively, e.g., the targeting complex being provided first, followed by the second targeting complex, etc, or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA, Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case: polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CasMG guide RNA that does not change when the guide sequence is changed to hybridize to a desired target sequence (e.g., sequences that contribute to the CasMG binding aspect of the guide RNA, e.g, the sequences that contribute to the dsRNA duplex(es) of the CasMG guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CasMG guide RNA, except that the portion encoding the guide sequence portion of the guide RNA is an insertion sequence (an insertion site). An insertion site is any nucleotide sequence used for the insertion of a the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g., Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40) nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

In some embodiments, a subject nucleic acid (e.g., a CasMG guide RNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides. 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-0-Methyl modified nucleotide (also referred to as 2'-0-Methyl RNA) is a naturally-occurring modification of RNA found in tRNA and other small RNAs that arises as a post-transcriptional modification. Oligonucleotides can be directly synthesized that contain 2'-0-Methyl RNA, This modification increases Tm of RNA; RNA duplexes but results in only small changes in RNA; DNA stability. It is stabile with respect to attack by single-stranded ribonucleases and is typically 5 to 10-fold less susceptible to DNases than DNA, It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA, These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-0-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-0-Methyl nucleotide and/or a 2' Fluoro modified nucleotide and/or a LNA base and/or a phosphorothioate linkage).

Examples of suitable nucleic acids (e.g., a CasMG guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages. 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage e.g., a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —$CH_2$—NH-0-$CH_2$—, —$CH_2$—N($CH_3$)-0-$CH_2$— (known as a methylene (methylimino) or MMI backbone), —$CH_2$-0-N($CH_3$)—$CH_2$—, —CH$_2$—N(CH$_3$)—N(CH$_3$)—CH$_2$— and -0-N(CH$_3$)—CH$_2$—CH$_2$— (wherein the native phosphodiester internucleotide linkage is represented as —O—P(=0)(OH)-0-CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside): siloxane backbones: sulfide, sulfoxide and sulfone backbones; formacetyl and thioformacetyl backbones; methylene formacetyl and thioformacetyl backbones: riboacetyl backbones: alkene containing backbones: sulfamate backbones: methyleneimino and methylenehydrazino backbones; sulfonate and sulfonamide backbones: amide backbones; and others having mixed N. O. S and CH$_2$ component parts.

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A, Braasch and David R. Corey. Biochemistry, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., Am. Chem. Soc, 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH$_2$—), group bridging the 2' oxygen atom and the 4' carbon atom wherein n is 1 or 2 (Singh et al., Chem. Commun., 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638, the disclosure of which is incorporated herein by reference in its entirety).

The synthesis and preparation of the LNA monomers adenine, cytosine, guanine, 5-methyl-cytosine, thymine and uracil, along with their oligomerization, and nucleic acid recognition properties have been described (e.g., Koshkin et al., Tetrahedron, 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to do alkyl or C$_2$ to do alkenyl and alkynyl. Particularly suitable are O((CH$_2$)$_n$O)$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON((CH$_2$)$_n$CH$_3$)$_2$, where n and m are from 1 to about 10. Other suitable polynucleotides comprise a sugar substituent group selected from: d to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—CH$_2$ CH$_2$OCH$_3$, also known as 2'-O-(2-methoxyethyl) or 2'-MOE) (Martin et al., Helv. Chim. Acta, 1995, 78, 486-504, the disclosure of which is incorporated herein by reference in its entirety) e.g., an alkoxyalkoxy group. A further suitable modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Other suitable sugar substituent groups include methoxy (—O—CH$_3$), aminopropoxy (—O CH$_2$ CH$_2$ CH$_2$NH$_2$), allyl (—CH$_2$—CH=CH$_2$), —O-allyl (—O—CH$_2$—CH=CH$_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mime tics such as cyclobutyl moieties in place of the pentofuranosyl sugar.

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al, FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., /. Pharmacol. Exp. Ther., 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Examples of PTDs include but are not limited to a minimal undecapeptide protein transduction domain (corresponding to residues 47-57 of HIV-1 TAT comprising SEQ ID NO:33); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7): 1732-1737); a truncated human calcitonin peptide (Trehin et al. (2004) Pharm. Research 21: 1248-1256); polylysine (Wender et al. (2000) Proc. Natl. Acad. Sci. USA 97: 13003-13008); SEQ ID NO:34; Transportan (SEQ ID NO:35); SEQ ID NO:36; and SEQ ID NO:37. Useful PTDs include but are not limited to, SEQ ID NO:38 or 39; an arginine homopolymer of from 3 arginine residues to 50 arginine residues; useful PTD domain amino acid sequences include, but are not limited to, any of the following: SEQ ID NO:40-43, and 44. In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

A CasMG guide RNA (or a nucleic acid comprising a nucleotide sequence encoding same) and/or a CasMG polypeptide of the present disclosure (or a nucleic acid comprising a nucleotide sequence encoding same) and/or a CasMG fusion polypeptide of the present disclosure (or a nucleic acid that includes a nucleotide sequence encoding a CasMG fusion polypeptide of the present disclosure) and/or a donor polynucleotide (donor template) can be introduced into a host cell by any of a variety of well-known methods.

Any of a variety of compounds and methods can be used to deliver to a target cell a CasMG system of the present disclosure (e.g., where a CasMG system comprises: a) a CasMG polypeptide of the present disclosure and a CasMG guide RNA; b) a CasMG polypeptide of the present disclosure, a CasMG guide RNA, and a donor template nucleic acid; c) a CasMG fusion polypeptide of the present disclosure and a CasMG guide RNA; d) a CasMG fusion polypeptide of the present disclosure, a CasMG guide RNA, and a donor template nucleic acid; e) an mRNA encoding a CasMG polypeptide of the present disclosure; and a CasMG guide RNA; f) an mRNA encoding a CasMG polypeptide of the present disclosure, a CasMG guide RNA, and a donor template nucleic acid; g) an mRNA encoding a CasMG fusion polypeptide of the present disclosure; and a CasMG guide RNA; h) an mRNA encoding a CasMG fusion polypeptide of the present disclosure, a CasMG guide RNA, and a donor template nucleic acid; i) a recombinant expression vector comprising a nucleotide sequence encoding a CasMG polypeptide of the present disclosure and a nucleotide sequence encoding a CasMG guide RNA; j) a recombinant expression vector comprising a nucleotide sequence encoding a CasMG polypeptide of the present disclosure, a nucleotide sequence encoding a CasMG guide RNA, and a nucleotide sequence encoding a donor template nucleic acid; k) a recombinant expression vector comprising a nucleotide sequence encoding a CasMG fusion polypeptide of the present disclosure and a nucleotide sequence encoding a CasMG guide RNA; l) a recombinant expression vector comprising a nucleotide sequence encoding a CasMG fusion polypeptide of the present disclosure, a nucleotide sequence encoding a CasMG guide RNA, and a nucleotide sequence encoding a donor template nucleic acid; m) a first recombinant expression vector comprising a nucleotide sequence encoding a CasMG polypeptide of the present disclosure, and a second recombinant expression vector comprising a nucleotide sequence encoding a CasMG guide RNA; n) a first recombinant expression vector comprising a nucleotide sequence encoding a CasMG polypeptide of the present disclosure, and a second recombinant expression vector comprising a nucleotide sequence encoding a CasMG guide RNA; and a donor template nucleic acid; o) a first recombinant expression vector comprising a nucleotide sequence encoding a CasMG fusion polypeptide of the present disclosure, and a second recombinant expression vector comprising a nucleotide sequence encoding a CasMG guide RNA; p) a first recombinant expression vector comprising a nucleotide sequence encoding a CasMG fusion polypeptide of the present disclosure, and a second recombinant expression vector comprising a nucleotide sequence encoding a CasMG guide RNA; and a donor template nucleic acid; q) a recombinant expression vector comprising a nucleotide sequence encoding a CasMG polypeptide of the present disclosure, a nucleotide sequence encoding a first CasMG guide RNA, and a nucleotide sequence encoding a second CasMG guide RNA; or r) a recombinant expression vector comprising a nucleotide sequence encoding a CasMG fusion polypeptide of the present disclosure, a nucleotide sequence encoding a first CasMG guide RNA, and a nucleotide sequence encoding a second CasMG guide RNA; or some variation of one of (a) through (r). As a non-limiting example, a CasMG system of the present disclosure can be combined with a lipid. As another non-limiting example, a CasMG system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

In some cases, a CasMG polypeptide of the present disclosure is provided as a nucleic acid (e.g., an mRNA, a DNA, a plasmid, an expression vector, a viral vector, etc.) that encodes the CasMG polypeptide. In some cases, the CasMG polypeptide of the present disclosure is provided directly as a protein (e.g., without an associated guide RNA or with an associate guide RNA, i.e., as a ribonucleoprotein complex). A CasMG polypeptide of the present disclosure can be introduced into a cell (provided to the cell) by any convenient method; such methods are known to those of ordinary skill in the art. As an illustrative example, a CasMG polypeptide of the present disclosure can be injected directly into a cell (e.g., with or without a CasMG guide RNA or nucleic acid encoding a CasMG guide RNA, and with or without a donor polynucleotide). As another example, a preformed complex of a CasMG polypeptide of the present disclosure and a CasMG guide RNA (an RNP) can be introduced into a cell (e.g, eukaryotic cell) (e.g., via injection, via nucleofection; via a protein transduction domain (PTD) conjugated to one or more components, e.g., conjugated to the CasMG protein, conjugated to a guide RNA, conjugated to a CasMG polypeptide of the present disclosure and a guide RNA; etc.). In some cases, a CasMG fusion polypeptide (e.g., dCasMG fused to a fusion partner, nickase CasMG fused to a fusion partner, etc.) of the present disclosure is provided as a nucleic acid (e.g., an mRNA, a DNA, a plasmid, an expression vector, a viral vector, etc.) that encodes the CasMG fusion polypeptide. In some cases, the CasMG fusion polypeptide of the present disclosure is provided directly as a protein (e.g., without an associated guide RNA or with an associate guide RNA, i.e., as a ribonucleoprotein complex). A CasMG fusion polypeptide of the present disclosure can be introduced into a cell (provided to the cell) by any convenient method; such methods are known to those of ordinary skill in the art. As an illustrative example, a CasMG fusion polypeptide of the present disclosure can be injected directly into a cell (e.g., with or without nucleic acid encoding a CasMG guide RNA and with or without a donor polynucleotide). As another example, a preformed complex of a CasMG fusion polypeptide of the present disclosure and a CasMG guide RNA (an RNP) can be introduced into a cell (e.g., via injection, via nucleofection; via a protein transduction domain (PTD) conjugated to one or more components, e.g., conjugated to the CasMG fusion protein, conjugated to a guide RNA, conjugated to a CasMG fusion polypeptide of the present disclosure and a guide RNA; etc.).

In some cases, a nucleic acid (e.g., a CasMG guide RNA; a nucleic acid comprising a nucleotide sequence encoding a CasMG polypeptide of the present disclosure; etc.) is delivered to a cell (e.g., a target host cell) and/or a polypeptide (e.g., a CasMG polypeptide; a CasMG fusion polypeptide) in a particle, or associated with a particle. In some cases, a CasMG system of the present disclosure is delivered to a cell in a particle, or associated with a particle. The terms "particle" and nanoparticle" can be used interchangeable, as appropriate. A recombinant expression vector comprising a nucleotide sequence encoding a CasMG polypeptide of the present disclosure and/or a CasMG guide RNA, an mRNA comprising a nucleotide sequence encoding a CasMG polypeptide of the present disclosure, and guide RNA may be delivered simultaneously using particles or lipid envelopes; for instance, a CasMG polypeptide and a CasMG guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CasMG polypeptide and a CasMG guide RNA are mixed together, e.g., at a 1: 1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CasMG polypeptide of the present disclosure (or an mRNA comprising a nucleotide sequence encoding a CasMG polypeptide of the present disclosure; or a recombinant expression vector comprising a nucleotide sequence encoding a CasMG polypeptide of the present disclosure) and/or CasMG guide RNA (or a nucleic acid such as one or more expression vectors encoding the CasMG guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self-assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a CasMG polypeptide of the present disclosure, a CasMG fusion polypeptide of the present disclosure, an RNP of the present disclosure, a nucleic acid of the present disclosure, or a CasMG system of the present disclosure.

In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell.

In some cases, lipid nanoparticles (LNPs) are used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19: 1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinKDMA), 1,2-dilinoleyl-4-(2-dimethylaminoethyl)-[1,3]-dioxolane (DLinKC2-DM A), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a CasMG guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL:PEGS-DMG or PEG-C-DOMG at 40: 10:40: 10 molar ratios). In some cases, 0.2% SP-DiOC18 is incorporated.

Spherical Nucleic Acid (SNA™) constructs and other nanoparticles (particularly gold nanoparticles) can be used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell.. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134: 1376-1391, Young et al., Nano Lett. 2012 12:3867-71, Zheng et al., Proc. Natl. Acad. Sci. USA. 2012 109: 11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al, Sci. Transl. Med. 5, 209ra152 (2013) and Mirkin, et al., Small, 10: 186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CasMG polypeptide of the present disclosure, a CasMG fusion polypeptide of the present disclosure, an RNP of the present disclosure, a nucleic acid of the present disclosure, or a CasMG system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CasMG polypeptide of the present disclosure, a CasMG fusion polypeptide of the present disclosure, an RNP of the present disclosure, a nucleic acid of the present disclosure, or a CasMG system of the present disclosure, to a target cell have a diameter of from 25 nm to 200 nm. In some cases, nanoparticles suitable for use in delivering a CasMG polypeptide of the present disclosure, a CasMG fusion polypeptide of the present disclosure, an RNP of the present disclosure, a nucleic acid of the present disclosure, or a CasMG system of the present disclosure, to a target cell have a diameter of 100 nm or less In some cases, nanoparticles suitable for use in delivering a CasMG polypeptide of the present disclosure, a CasMG fusion polypeptide of the present disclosure, an RNP of the present disclosure, a nucleic acid of the present disclosure, or a CasMG system of the present disclosure, to a target cell have a diameter of from 35 nm to 60 nm.

Nanoparticles suitable for use in delivering a CasMG polypeptide of the present disclosure, a CasMG fusion polypeptide of the present disclosure, an RNP of the present disclosure, a nucleic acid of the present disclosure, or a CasMG system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CasMG polypeptide of the present disclosure, a CasMG fusion polypeptide of the present disclosure, an RNP of the present disclosure, a nucleic acid of the present disclosure, or a CasMG system of the present disclosure, to a target cell. A prototype nanoparticle of semi-solid nature is the liposome.

In some cases, an exosome is used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell. Exosomes are endogenous nano-vesicles that transport RNAs and proteins, and which can deliver RNA to the brain and other target organs.

In some cases, a liposome is used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoley-loxy-N,N-dimethyl-3-aminopropane (DLinDMA), 1,2-distearoyl-sn-glycero-3-phosphocholine (DSPC) and cholesterol, in a 2:40: 10:48 molar percent ratio. The SNALP liposomes may be prepared by formulating D-Lin-DMA and PEG-C-DMA with distearoylphosphatidylcholine (DSPC), Cholesterol and siRNA using a 25: 1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000)carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethyleneglycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+-0.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a CasMG system of the present disclosure or component(s) thereof or nucleic acids encoding the same to form lipid nanoparticles (LNPs). Suitable lipids include, but are not limited to, DLin-KC2-DMA4, Cl 2-200 and colipids disteroylphosphatidyl choline, cholesterol, and PEG-DMG may be formulated with a CasMG system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A CasMG system of the present disclosure, or a component thereof, may be delivered encapsulated in PLGA microspheres such as that further described in US published applications 20130252281 and 20130245107 and 20130244279.

Supercharged proteins can be used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell. Supercharged proteins are a class of engineered or naturally-occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can facilitate the functional delivery of these macromolecules into mammalian cells both in vitro and in vivo.

Cell Penetrating Peptides (CPPs) can be used to deliver a CasMG polypeptide of the present disclosure, a CasMG fusion polypeptide of the present disclosure, an RNP of the present disclosure, a nucleic acid of the present disclosure, or a CasMG system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

The present disclosure provides a modified cell comprising a CasMG polypeptide of the present disclosure and/or a nucleic acid comprising a nucleotide sequence encoding a CasMG polypeptide of the present disclosure. The present disclosure provides a modified cell comprising a CasMG polypeptide of the present disclosure, where the modified cell is a cell that does not normally comprise a CasMG polypeptide of the present disclosure. The present disclosure provides a modified cell (e.g., a genetically modified cell) comprising nucleic acid comprising a nucleotide sequence encoding a CasMG polypeptide of the present disclosure. The present disclosure provides a genetically modified cell that is genetically modified with an mRNA comprising a nucleotide sequence encoding a CasMG polypeptide of the present disclosure. The present disclosure provides a genetically modified cell that is genetically modified with a recombinant expression vector comprising a nucleotide sequence encoding a CasMG polypeptide of the present disclosure. The present disclosure provides a genetically modified cell that is genetically modified with a recombinant expression vector comprising: a) a nucleotide sequence encoding a CasMG polypeptide of the present disclosure; and b) a nucleotide sequence encoding a CasMG guide RNA of the present disclosure. The present disclosure provides a genetically modified cell that is genetically modified with a recombinant expression vector comprising: a) a nucleotide sequence encoding a CasMG polypeptide of the present disclosure; b) a nucleotide sequence encoding a CasMG guide RNA of the present disclosure; and c) a nucleotide sequence encoding a donor template.

A cell that serves as a recipient for a CasMG polypeptide of the present disclosure and/or a nucleic acid comprising a nucleotide sequence encoding a CasMG polypeptide of the present disclosure and/or a CasMG guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a CasMG polypeptide of the present disclosure and/or a nucleic acid comprising a nucleotide sequence encoding a CasMG polypeptide of the present disclosure and/or a CasMG guide RNA of the present disclosure is referred to as a "host cell" or a "target cell." A host cell or a target cell can be a recipient of a CasMG system of the present disclosure. A host cell or a target cell can be a recipient of a CasMG RNP of the present disclosure. A host cell or a target cell can be a recipient of a single component of a CasMG system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *Brassica* sp. including oilseed rape, sorghum, sugarbeet, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g., kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbial cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g., an embryonic stem (ES) cell, an induced pluripotent stem (iPS) cell; a germ cell (e.g., an oocyte, a sperm, an oogonia, a spermatogonia, etc.); a somatic cell, e.g., a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell. Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34$^+$ and CD3. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). NSCs are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, Chinese artichoke (crosnes), Chinese cabbage, Chinese celery, Chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicomia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a suborder, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

The present disclosure provides a kit comprising a CasMG system of the present disclosure, or a component of a CasMG system of the present disclosure. A kit of the present disclosure can comprise: a) a CasMG polypeptide of the present disclosure and a CasMG guide RNA; b) a CasMG polypeptide of the present disclosure, a CasMG guide RNA, and a donor template nucleic acid; c) a CasMG fusion polypeptide of the present disclosure and a CasMG guide RNA; d) a CasMG fusion polypeptide of the present disclosure, a CasMG guide RNA, and a donor template nucleic acid; e) an mRNA encoding a CasMG polypeptide of the present disclosure; and a CasMG guide RNA; f) an mRNA encoding a CasMG polypeptide of the present disclosure, a CasMG guide RNA, and a donor template nucleic acid; g) an mRNA encoding a CasMG fusion polypeptide of the present disclosure; and a CasMG guide RNA; h) an mRNA encoding a CasMG fusion polypeptide of the present disclosure, a CasMG guide RNA, and a donor template nucleic acid; i) a recombinant expression vector comprising a nucleotide sequence encoding a CasMG polypeptide of the present disclosure and a nucleotide sequence encoding a CasMG guide RNA; j) a recombinant expression vector comprising a nucleotide sequence encoding a CasMG polypeptide of the present disclosure, a nucleotide sequence encoding a CasMG guide RNA, and a nucleotide sequence encoding a donor template nucleic acid; k) a recombinant expression vector comprising a nucleotide sequence encoding a CasMG fusion polypeptide of the present disclosure and a nucleotide sequence encoding a CasMG guide RNA; l) a recombinant expression vector comprising a nucleotide sequence encoding a CasMG fusion polypeptide of the present disclosure, a nucleotide sequence encoding a CasMG guide RNA, and a nucleotide sequence encoding a donor template nucleic acid; m) a first recombinant expression vector comprising a nucleotide sequence encoding a CasMG polypeptide of the present disclosure, and a second recombinant expression vector comprising a nucleotide sequence encoding a CasMG guide RNA; n) a first recombinant expression vector comprising a nucleotide sequence encoding a CasMG polypeptide of the present disclosure, and a second recombinant expression vector comprising a nucleotide sequence encoding a CasMG guide RNA; and a donor template nucleic acid; o) a first recombinant expression vector comprising a nucleotide sequence encoding a CasMG fusion polypeptide of the present disclosure, and a second recombinant expression vector comprising a nucleotide sequence encoding a CasMG guide RNA; p) a first recombinant expression vector comprising a nucleotide sequence encoding a CasMG fusion polypeptide of the present disclosure, and a second recombinant expression vector comprising a nucleotide sequence encoding a CasMG guide RNA; and a donor template nucleic acid; q) a recombinant expression vector comprising a nucleotide sequence encoding a CasMG polypeptide of the present disclosure, a nucleotide sequence encoding a first CasMG guide RNA, and a nucleotide sequence encoding a second CasMG guide RNA; or r) a recombinant expression vector comprising a nucleotide sequence encoding a CasMG fusion polypeptide of the present disclosure, a nucleotide sequence encoding a first CasMG guide RNA, and a nucleotide sequence encoding a second CasMG guide RNA; or some variation of one of (a) through (r).

A kit of the present disclosure can comprise: a) a component, as described above, of a CasMG system of the present disclosure, or can comprise a CasMG system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CasMG guide RNA; and the like. A kit of the present disclosure can comprise: a) a component, as described above, of a CasMG system of the present disclosure, or can comprise a CasMG system of the present disclosure; and b) a therapeutic agent. A kit of the present disclosure can comprise a recombinant expression vector comprising: a) an insertion site for inserting a nucleic acid comprising a nucleotide sequence encoding a portion of a CasMG guide RNA that hybridizes to a target nucleotide sequence in a target nucleic acid; and b) a nucleotide sequence encoding the CasMG-binding portion of a CasMG guide RNA. A kit of the present disclosure can comprise a recombinant expression vector comprising: a) an insertion site for inserting a nucleic acid comprising a nucleotide sequence encoding a portion of a CasMG guide RNA that hybridizes to a target nucleotide sequence in a target nucleic acid; b) a nucleotide sequence encoding the CasMG-binding portion of a CasMG guide RNA; and c) a nucleotide sequence encoding a CasMG polypeptide of the present disclosure.

A CasMG polypeptide of the present disclosure, or a CasMG fusion polypeptide of the present disclosure, finds use in a variety of methods (e.g., in combination with a CasMG guide RNA and in some cases further in combination with a donor template). For example, a CasMG polypeptide of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a CasMG polypeptide of the present disclosure; and b) one or more (e.g., two) CasMG guide RNAs. In some cases, a method of the present disclosure for modifying a target nucleic acid comprises contacting the target nucleic acid with: a) a CasMG polypeptide of the present disclosure; b) a CasMG guide RNA; and c) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a CasMG polypeptide includes binding of the CasMG polypeptide to a particular region in a target nucleic acid (by virtue of being targeted there by an associated CasMG guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc, modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5): 1173-83; Wang et al., Cell. 2013 May 9; 153(4): 910-8; Auer et al, Genome Res. 2013 Oct. 31; Chen et al., Nucleic Acids Res. 2013 Nov. 1; 41(20):e19; Cheng et al., Cell Res. 2013 October; 23(10): 1163-71; Cho et al., Genetics. 2013 November; 195(3): 1177-80; DiCarlo et al., Nucleic Acids Res. 2013 April; 41(7):4336-43; Dickinson et al., Nat Methods. 2013 October; 10(10): 1028-34; Ebina et al., Sci Rep. 2013; 3:2510; Fujii et al, Nucleic Acids Res. 2013 Nov. 1; 41(20):el87; Hu et al., Cell Res. 2013 November; 23(11): 1322-5; Jiang et al., Nucleic Acids Res. 2013 Nov. 1; 41(20):el88; Larson et al, Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6): 1380-9; Upadhyay et al., G3 (Bethesda). 2013 Dec. 9; 3(12):2233-8; Walsh et al., Proc Natl Acad Sci U.S.A. 2013 Sep. 24; 110(39): 15514-5; Xie et al., Mol Plant. 2013 Oct. 9; Yang et al., Cell. 2013 Sep. 12; 154(6): 1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated herein by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a CasMG polypeptide or with a CasMG fusion polypeptide, etc., encompass all methods for contacting the target nucleic acid. For example, a CasMG polypeptide can be provided to a cell as protein, RNA (encoding the CasMG polypeptide), or DNA (encoding the CasMG polypeptide); while a CasMG guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for CasMG polypeptide; in the form of a protein for a CasMG fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a CasMG polypeptide or a CasMG fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises contacting a target nucleic acid with a CasMG polypeptide of the present disclosure, or with a CasMG fusion polypeptide of the present disclosure. In some cases, abmethod of the present disclosure for modifying a target nucleic acid comprises contacting a target nucleic acid with a CasMG polypeptide and a CasMG guide RNA. In some cases, abmethod of the present disclosure for modifying a target nucleic acid comprises contacting a target nucleic acid with a CasMG polypeptidel, a first CasMG guide RNA, and a second CasMG guide RNA In some cases, a method of the present disclosure for modifying a target nucleic acid comprises contacting a target nucleic acid with a CasMG polypeptide of the present disclosure and a CasMG guide RNA and a DNA donor template.

A CasMG polypeptide of the present disclosure, or a CasMG fusion polypeptide of the present disclosure, when bound to a CasMG guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CasMG guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g., fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g., a stem cell, e.g., an embryonic stem (ES) cell, an induced pluripotent stem (iPS) cell, a germ cell (e.g., an oocyte, a sperm, an oogonia, a spermatogonia, etc.), an adult stem cell, a somatic cell, e.g., a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e., splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to genetically modify a target cell, and the like). Because the guide RNA provides specificity by hybridizing to target nucleic acid, a mitotic and/or post-mitotic cell of interest in the disclosed methods may include a cell from any organism (e.g., a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CasMG1 protein (and/or nucleic acid encoding the protein such as DNA and/or RNA), and/or CasMG1 guide RNA (and/or a DNA encoding the guide RNA), and/or donor template, and/or RNP can be introduced into an individual (e.g., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Non-limiting examples of cells can be found in the section "Modified host cells".

Guided by a CasMG dual or single guide RNA, a CasMG protein in some cases generates site-specific double strand breaks (DSBs) or single strand breaks (SSBs) (e.g., when the CasMG protein is a nickase variant) within double-stranded DNA (dsDNA) target nucleic acids, which are repaired either by non-homologous end joining (NHEJ) or homology-directed repair(HDR).

In some cases, contacting a target DNA (with a CasMG protein and a CasMG guide RNA) occurs under conditions that are permissive for nonhomologous end joining or homology-directed repair. Thus, in some cases, a subject method includes contacting the target DNA with a donor polynucleotide or DNA donor template (e.g., by introducing the donor polynucleotide or DNA donor template into a cell), wherein the donor polynucleotide or DNA donor template, a portion of the donor polynucleotide or DNA donor template, a copy of the donor polynucleotide or DNA donor template, or a portion of a copy of the donor polynucleotide or DNA donor template integrates into the target DNA. In some cases, the method does not comprise contacting a cell with a donor polynucleotide or DNA donor template, and the target DNA is modified such that nucleotides within the target DNA are deleted.

In some cases, CasMG guide RNA (or DNA encoding same) and a CasMG protein (or a nucleic acid encoding same, such as an RNA or a DNA, e.g, one or more expression vectors) are coadministered (e.g., contacted with a target nucleic acid, administered to cells, etc.) with a donor polynucleotide sequence or DNA donor template that includes at least a segment with homology to the target DNA sequence, the subject methods may be used to add, e.g., insert or replace, nucleic acid material to a target DNA sequence (e.g., to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CasMG guide RNA and CasMG protein is useful in any in vitro or in vivo application in which it is desirable to modify DNA in a site-specific, i.e., "targeted", way, for example gene knockout, gene knock-in, gene editing, gene tagging, etc., as used in, for example, conferring a trait, gene therapy, e.g., to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into the genome where a target sequence is cleaved, a donor polynucleotide or DNA donor template (a nucleic acid comprising a donor sequence) can also be provided to the cell. By a "donor sequence" or "donor polynucleotide" or "donor template" or "DNA donor template" it is meant a nucleic acid sequence to be inserted at the site cleaved by the CasMG protein (e.g., after dsDNA cleavage, after nicking a target DNA, after dual nicking a target DNA, and the like). The donor polynucleotide or DNA donor template can contain sufficient homology to a genomic sequence at the target site, e.g., 70%, 80%, 85%, 90%, 95%, or 100% homology with the nucleotide sequences flanking the target site, e.g., within about 50 bases or less of the target site, e.g., within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides or DNA donor template can be of any length, e.g., 10 nucleotides or more, 50 nucleotides or more, 100 nucleotides or more, 250 nucleotides or more, 500 nucleotides or more, 1000 nucleotides or more, 5000 nucleotides or more, etc.

The donor sequence or DNA donor template is typically not identical to the genomic sequence that it replaces. Rather, the donor sequence or DNA donor template may contain at least one or more single base changes, insertions, deletions, inversions or rearrangements with respect to the genomic sequence, so long as sufficient homology is present to support homology-directed repair (e.g., for gene correction, e.g., to convert a disease-causing base pair to a non-disease-causing base pair). In some embodiments, the donor sequence or DNA donor template comprises a nonhomologous sequence flanked by two regions of homology, such that homology-directed repair between the target DNA region and the two flanking sequences results in insertion of the non-homologous sequence at the target region. Donor sequences or DNA donor template may also comprise a vector backbone containing sequences that are not homologous to the DNA region of interest and that are not intended for insertion into the DNA region of interest. Generally, the homologous region(s) of a donor sequence or DNA donor template will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence or DNA donor template may comprise certain sequence differences as compared to the genomic sequence, e.g., restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (e.g., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence or DNA donor template is provided to the cell as single-stranded DNA. In some cases, the donor sequence or DNA donor template is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphor amidates, and O-methyl ribose or deoxyribose residues. As an alternative to protecting the termini of a linear donor sequence, additional lengths of sequence may be included outside of the regions of homology that can be degraded without impacting recombination. A donor sequence or DNA donor template can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV, geminiviruses), as described elsewhere herein for nucleic acids encoding a CasMG guide RNA and/or a CasMG fusion polypeptide and/or donor polynucleotide.

In some embodiments the disclosed RNA-guided nucleases can be used in systems and methods for detecting one or more specific target DNA molecules in a sample. Examples of target DNA molecule detection schemes that were implemented with distinct RNA guided nucleases are described in in US20190241954, which is hereby incorporated by reference in its entirety. In certain embodiments, the methods and reagents (e.g., reporter molecules) described in US20190241954 and incorporated herein by reference can be adapted for use with the CasMG polypeptides, CasMG fusion polypeptides, and CasMG guide RNA molecules disclosed herein.

Guide RNAs for a CasMG polypeptide or fusion polypeptide are designed to recognize a target DNA molecule having target sequences in samples potentially or suspected of having the target DNA of interest. The DNA having the target sequence can be single stranded or double stranded. If the sample contains the target DNA molecule, binding of the target DNA molecule by the CasMG guide RNA/CasMG polypeptide or fusion polypeptide complex will trigger the CasMG polypeptide or fusion polypeptide's collateral nuclease activity (i.e., cleavage of a single stranded DNA (ssDNA) that does not contain the target DNA sequences). Consequently, a DNA-based reporter molecule produces an output following cleavage by the CasMG polypeptide or fusion polypeptide collateral nuclease activity that can be assayed. Presence or absence of the output, therefore, indicates presence or absence of a target DNA molecule having the target DNA sequence in the sample.

In some cases, a subject method includes a step of measuring (e.g., measuring a detectable signal produced by CasMG-mediated ssDNA cleavage). Because a CasMG cleaves non-targeted ssDNA once activated, which occurs when a guide RNA hybridizes with a target DNA in the presence of a CasMG, a detectable signal can be any signal that is produced when ssDNA is cleaved. In certain embodiments, the reporter molecule is a ssDNA molecule that further comprises a detectable label. In certain embodiments, the detectable label is covalently linked to the ssDNA. For example, in some cases the step of measuring can include one or more of: gold nanoparticle based detection (e.g., see Xu et al., Angew Chem Int Ed Engl. 2007; 46(19):3468-70; and Xia et al., Proc Natl Acad Sci USA. 2010 June, 15; 107(24):10837-41), fluorescence polarization, colloid phase transition/dispersion (e.g., Baksh et al., Nature. 2004 Jan. 8; 427(6970):139-41), electrochemical detection, semiconductor-based sensing (e.g., Rothberg et al., Nature. 2011 Jul. 20; 475(7356):348-52; e.g., one could use a phosphatase to generate a pH change after ssDNA cleavage reactions, by opening 2'-3' cyclic phosphates, and by releasing inorganic phosphate into solution), and detection of a labeled detector ssDNA (DNA reporter molecule). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The measuring can in some cases be quantitative, e.g., in the sense that the amount of signal detected can be used to determine the amount of a target DNA molecule present in the sample. The measuring can in some cases be qualitative, e.g., in the sense that the presence or absence of detectable signal can indicate the presence or absence of a target DNA molecule (e.g., virus, cDNA from a viral RNA, SNP, etc.). In some cases, a detectable signal will not be present (e.g., above a given threshold level) unless the target DNA(s) (e.g., virus, cDNA from a viral RNA, SNP, etc.) is present above a particular threshold concentration. In some cases, the threshold of detection can be titrated by modifying the amount of CasMG, guide RNA, sample volume, and/or detector ssDNA (if one is used). As such, for example, as would be understood by one of ordinary skill in the art, a number of controls can be used if desired in order to set up one or more reactions, each set up to detect a different threshold level of target DNA, and thus such a series of reactions could be used to determine the amount of a target DNA molecule present in a sample (e.g., one could use such a series of reactions to determine that a target DNA molecule is present in the sample "at a concentration of at least X"). The compositions and methods of this disclosure can be used to detect any DNA target, including DNA targets obtained from RNA targets. For example, any virus that integrates nucleic acid material into the genome can be detected because a subject sample can include cellular genomic DNA, and the guide RNA can be designed to detect integrated nucleotide sequence.

In some cases, a method of the present disclosure can be used to determine the amount of a target DNA molecule in a sample (e.g., a sample comprising the target DNA molecules and a plurality of non-target DNAs). Determining the amount of a target DNA molecule in a sample can comprise comparing the amount of detectable signal generated from a test sample to the amount of detectable signal generated from a reference sample. Determining the amount of a target DNA molecule in a sample can comprise: measuring the detectable signal to generate a test measurement; measuring a detectable signal produced by a reference sample to generate a reference measurement; and comparing the test measurement to the reference measurement to determine an amount of a target DNA molecule present in the sample.

For example, in some cases, a method of the present disclosure for determining the amount of a target DNA molecule in a sample comprises: a) contacting the sample (e.g., a sample comprising the target DNA and a plurality of non-target DNAs) with: (i) a guide RNA that hybridizes with the target DNA, (ii) a CasMG that cleaves target DNAs present in the sample that hybridize to the guide RNA, and (iii) a reporter molecule (e.g., a detector ssDNA); b) measuring a detectable signal produced by CasMG-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

As another example, in some cases, a method of the present disclosure for determining the amount of a target DNA molecule in a sample comprises: a) contacting the sample (e.g., a sample comprising the target DNA molecule and a plurality of non-target DNAs) with: i) a precursor CasMG guide RNA array comprising two or more guide RNAs each of which has a different guide sequence; ii) a CasMG that cleaves the precursor guide RNA array into individual guide RNAs, and also cleaves RNAs of the sample; and (iii) a DNA reporter molecule (e.g., a detector ssDNA); b) measuring a detectable signal produced by CasMG-mediated ssDNA cleavage (e.g., cleavage of the detector ssDNA), generating a test measurement; c) measuring a detectable signal produced by each of two or more reference samples to generate two or more reference measurements; and d) comparing the test measurement to the reference measurements to determine an amount of target DNA present in the sample.

In some cases, a subject method includes contacting a sample (e.g., a sample comprising a target DNA molecule and a plurality of non-target ssDNAs) with: i) a CasMG polypeptide; ii) a CasMG guide RNA (or precursor guide RNA array); and iii) a DNA-based reporter (detector DNA) that is single stranded and does not hybridize with the guide sequence of the guide RNA. For example, in some cases, a subject method includes contacting a sample with a labeled single stranded reporter DNA molecule (detector ssDNA) that includes a fluorescence-emitting dye pair; the CasMG cleaves the labeled detector ssDNA after it is activated (by binding to the guide RNA in the context of the guide RNA hybridizing to a target DNA); and the detectable signal that is measured is produced by the fluorescence-emitting dye pair. For example, in some cases, a subject method includes contacting a sample with a labeled detector ssDNA comprising a fluorescence resonance energy transfer (FRET) pair or a quencher/fluor pair, or both. In some cases, a subject method includes contacting a sample with a DNA reporter molecule comprising a detectably labeled ssDNA comprising a FRET pair. In some cases, a subject method includes contacting a sample with a DNA reporter molecule comprising a detectably labeled ssDNA comprising a fluor/quencher pair.

In certain embodiments, fluorescence-emitting dye pairs used in a DNA reporter molecule comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair. The term "fluorescence-emitting dye pair" is used interchangeably with the phrase "a FRET pair and/or a quencher/fluor pair."

In some cases (e.g., when the detector ssDNA includes a FRET pair) the DNA reporter molecule comprising a detectably labeled ssDNA produces an amount of detectable signal prior to being cleaved, and the amount of detectable signal that is measured is reduced when the detectably labeled ssDNA is cleaved. In some cases, the labeled detector ssDNA produces a first detectable signal prior to being cleaved (e.g., from a FRET pair) and a second detectable signal when the detectably labeled ssDNA is cleaved (e.g., from a quencher/fluor pair). As such, in some cases, the detectably labeled ssDNA comprises a FRET pair and a quencher/fluor pair.

In some cases, the detectably labeled detector ssDNA comprises a FRET pair. FRET is a process by which radiationless transfer of energy occurs from an excited state fluorophore to a second chromophore in close proximity The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Forster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector ssDNA includes two signal partners (a signal pair), when one signal partner is a FRET donor moiety and the other signal partner is a FRET acceptor moiety. A subject labeled detector ssDNA that includes such a FRET pair (a FRET donor moiety and a FRET acceptor moiety) will thus exhibit a detectable signal (a FRET signal) when the signal partners are in close proximity (e.g., while on the same DNA molecule), but the signal will be reduced (or absent) when the partners are separated (e.g., after cleavage of the detectably labelled ssDNA molecule by a CasMG polypeptide or fusion polypeptide/guide RNA complex associated with a DNA target molecule).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to ECFP-EYFP, mTurquoise2-sEYFP, mTurquoise2-mVenus, Clover-mRuby2, mClover3-mRuby3, mNeonGreen-mRuby3, eqFP650-iRFP, mAmetrine-tdTomato, LSSmOrange-mKate2, EGFP-sREACh, EGFP-ShadowG, EGFP-activated PA-GFP, EGFP-Phanta, mTagBFP-sfGFP, mVenus-mKOκ, and CyOFP1-mCardinal. See also: Bajar et al. Sensors (Basel). 2016 Sep. 14; 16(9); and Abraham et al. PLoS One. 2015 Aug. 3; 10(8):e0134436.

In some cases, a detectable signal that can be assayed is produced when the DNA reporter molecule comprising the labeled detector ssDNA is cleaved (e.g., in some cases, the labeled detector ssDNA comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the DNA reporter molecule comprising the labeled detector ssDNA is cleaved. For example, in some cases, the signal exhibited by one signal partner (a signal moiety) is quenched by the other signal partner (a quencher signal moiety), e.g., when both are present on the same ssDNA molecule prior to cleavage by a CasMG. Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector ssDNA by a CasMG polypeptide or fusion polypeptide/guide RNA complex associated with a DNA target molecule, but the signal will be quenched when the partners are in close proximity (e.g., prior to cleavage of the detector ssDNA by a CasMG polypeptide or fusion polypeptide/guide RNA complex associated with a DNA target molecule).

In some cases, the signal moiety used in the DNA reporter molecule is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases the quencher moiety used in the DNA reporter molecule absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, which are each hereby incorporated by reference in their entirety.

Examples of fluorescent labels that can be used in the DNA reporter molecule include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label that can be used in the DNA reporter molecule is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label that can be used in the DNA reporter molecule is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes that can be used in the DNA reporter molecule include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes that can be used in the DNA reporter molecule include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties that can be used in the DNA reporter molecule include, but are not limited to: a dark quencher, a Black Hole Quencher® (BHQ®) (e.g., BHQ-0, BHQ-1, BHQ-2, BHQ-3), a Qx1 quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety that can be used in the DNA reporter molecule is selected from: a dark quencher, a Black Hole Quencher® (BHQ®) (e.g., BHQ-0, BHQ-1, BHQ-2, BHQ-3), a Qx1 quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher that can be used in the DNA reporter molecule include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties that can be used in the DNA reporter molecule, are set forth in., Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585, and 20030003486; and international patent applications: WO200142505 and WO200186001, all of which are hereby incorporated by reference in their entireties.

In some cases, cleavage of the DNA reporter molecule comprising a labeled detector ssDNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector ssDNA can be detected by a color-shift. Such a shift can be expressed as a loss of an amount of signal of one color (wavelength), a gain in the amount of another color, a change in the ration of one color to another, and the like.

As described above, in some cases, a nucleic acid (e.g., a recombinant expression vector) of the present disclosure (e.g., a nucleic acid comprising a nucleotide sequence encoding a CasMG polypeptide of the present disclosure; a nucleic acid comprising a nucleotide sequence encoding a CasMG fusion polypeptide of the present disclosure; etc.), is used as a transgene to generate a transgenic non-human organism(e.g., a plant) that produces a CasMG polypeptide, or a CasMG fusion polypeptide, of the present disclosure. The present disclosure provides a transgenic-non-human organism comprising a nucleotide sequence encoding a CasMG polypeptide, or a CasMG fusion polypeptide, of the present disclosure.

The present disclosure provides a transgenic non-human animal, which animal comprises a transgene comprising a nucleic acid comprising a nucleotide sequence encoding a CasMG polypeptide or a CasMG fusion polypeptide. In some embodiments, the genome of the transgenic non-human animal comprises a nucleotide sequence encoding a CasMG polypeptide or a CasMG fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a CasMG polypeptide or a CasMG fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

As described above, in some cases, a nucleic acid (e.g., a recombinant expression vector) of the present disclosure (e.g., a nucleic acid comprising a nucleotide sequence encoding a CasMG polypeptide of the present disclosure; a nucleic acid comprising a nucleotide sequence encoding a CasMG fusion polypeptide of the present disclosure; etc.), is used as a transgene to generate a transgenic plant that produces a CasMG polypeptide, or a CasMG fusion polypeptide, of the present disclosure. The present disclosure provides a transgenic plant comprising a nucleotide sequence encoding a CasMG polypeptide, or a CasMG fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses including geminiviruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (e.g., in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif). A nucleic acid of the present disclosure (e.g., a nucleic acid (e.g., a recombinant expression vector) comprising a nucleotide sequence encoding a CasMG polypeptide, or a CasMG fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g., infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a CasMG polypeptide, or a CasMG fusion polypeptide, of the present disclosure.

Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a CasMG polypeptide, or a CasMG fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

TABLE 1

Biological sequences and mutations referred to in the specification and claims

| Name | SEQ ID NO or Mutation |
|---|---|
| CasMG1 | 1 |
| CasMG1 Direct Repeat (Residues 16-36 underlined) | 2 |
| CTP 1 | 3 |
| CTP 2 | 4 |
| CTP 3 | 5 |
| CTP 4 | 6 |
| CTP 5 | 7 |
| CTP 6 | 8 |
| CTP 7 | 9 |
| CTP 8 | 10 |

TABLE 1-continued

Biological sequences and mutations referred to in the specification and claims

| Name | SEQ ID NO or Mutation |
|---|---|
| CTP 9 | 11 |
| CTP 10 | 12 |
| CTP 11 | 13 |
| tracrRNA of CasMG1 locus | 14 |
| Residues 16 to 36 of SEQ ID NO: 2 | 15 |
| EEP 1 | 16 |
| EEP 2 | 17 |
| NLS 3 | 18 |
| NLS 4 | 19 |
| NLS 5 | 20 |
| NLS 6 | 21 |
| NLS 7 | 22 |
| NLS 8 | 23 |
| NLS 9 | 24 |
| NLS 10 | 25 |
| NLS 11 | 26 |
| NLS 12 | 27 |
| NLS 13 | 28 |
| NLS 14 | 29 |
| NLS 15 | 30 |
| NLS 16 | 31 |
| NLS 17 | 32 |
| PTD 1 | 33 |
| PTD 2 | 34 |
| PTD 3 | 35 |
| PTD 4 | 36 |
| PTD 5 | 37 |
| PTD 6 | 38 |
| PTD 7 | 39 |
| PTD 8 | 40 |
| PTD 9 | 41 |
| PTD 10 | 42 |
| PTD 11 | 43 |
| PTD 12 | 44 |
| Linker 1 | 45 |
| Linker 2 | 46 |
| Linker 3 | 47 |
| Linker 4 | 48 |
| Linker 5 | 49 |
| Linker 6 | 50 |
| Linker 7 | 51 |
| Linker 8 | 52 |
| Linker 9 | 53 |
| CasMG1 RuvCI | 54 |
| CasMG2 RuvCII | 55 |
| CasMG3 RuvCIII | 56 |
| NLS1 | 57 |
| penetratin | 58 |
| dCasMG1 mutations (comprise or correspond to position in SEQ ID NO: 1) | N799A, E893A, and/or D1129A |
| Enhanced CasMG1 mutations (comprise or correspond to position in SEQ ID NO: 1) | Y277P, A487K, T880A, A904F/Q, Q934E, I956K, I964V, N1004D, T1012F/Y, Y1116F, and/or C1140G |
| CasMG2 | 59 |
| CasMG2 Direct Repeat (DR; residues 18-36 underlined) | 60 |
| tracrRNA of the CasMG2 locus | 61 |
| Residues 18-36 of SEQ ID NO: 60 | 62 |
| CasMG2 RuvCI | 63 |
| CasMG2 RuvCII | 64 |
| CasMG2 RuvCIII | 65 |
| dCasMG2 mutations (comprise or correspond to position in SEQ ID NO: 59) | D877A, E970A, and/or D1219A |
| Enhanced CasMG2 mutations (comprise or correspond to position in SEQ ID NO: 59) | R545K, S957A, Q981F, T1041V, N1082D, F1092Y, and/or Y1205F |
| CasMG3 | 66 |
| CasMG3 Direct Repeat (DR; residues 18-36 underlined) | 67 |
| tracrRNA sequence of the CasMG3 locus | 68 |
| residues 18-36 of SEQ ID NO: 67 | 69 |
| CasMG3 RuvCI | 70 |
| CasMG3 RuvCII | 71 |
| CasMG3 RuvCIII | 72 |
| dCASMG3 mutations (comprise or correspond to position in SEQ ID NO: 66) | D848A, E933A, and/or D1184A |
| Stable CasMG3 mutations (comprise or | Y296F, T920A, F944Q, C1047N/D, |

TABLE 1-continued

Biological sequences and mutations referred to in the specification and claims

| Name | SEQ ID NO or Mutation |
|---|---|
| correspond to position in SEQ ID NO: 66) | F1057Y, and/or K1213L |
| Stable CR CasMG3 Mutations (comprise or correspond to position in SEQ ID NO: 66) | T799I |
| CasMG4 | 73 |
| CasMG4 Direct repeat (DR; residues 18-36 underlined) | 74 |
| tracrRNA sequence of the CasMG4 locus | 75 |
| Residues 18-36 of SEQ ID NO: 74 | 76 |
| CasMG4 RuvCI | 77 |
| CasMG4 RuvCII | 78 |
| CasMG4 RuvCIII | 79 |
| dCasMG4 mutations (comprise or correspond to position in SEQ ID NO: 73) | D832A, E925A, and/or D1175A |
| Enhanced CasMG4 mutations (comprise or correspond to position in SEQ ID NO: 73) | D505N, Q513K, C912A, D919N, I936F/Q, A966E, N1037D, F1047Y, Y1159F, A1186G, and/or P1204L |
| Enhanced CR CasMG4 Mutations (comprise or correspond to position in SEQ ID NO: 73) | L783I |
| CasMG5 | 80 |
| CasMG5 Direct repeat (residues 18-36 underlined) | 81 |
| tracrRNA sequence of the CasMG5 locus | 82 |
| Residues 18-36 of SEQ ID NO: 81 | 83 |
| CasMG5 RuvCI | 84 |
| CasMG5 RuvCII | 85 |
| CasMG5 RuvCIII | 86 |
| dCasMG5 mutations (comprise or correspond to position in SEQ ID NO: 80) | D833A, E926A, and/or D1172A |
| Enhanced CasMG5 mutations (comprise or correspond to position in SEQ ID NO: 80) | D291P, D505N, Q513K, V913A, L937F/Q, I958L, D967E, N989K, I997V, D1038N, I1048F/Y, Y1158F, and/or F1198L |
| Enhanced CR CasMG5 Mutation (comprise or correspond to position in SEQ ID NO: 80) | L782I |
| CasMG6 | 87 |
| CasMG6 Direct repeat (residues 18-36 underlined) | 88 |
| tracrRNA sequence of the CasMG6 locus | 89 |
| Residues 18-36 of SEQ ID NO: 88 | 90 |
| CasMG6 RuvCI | 91 |
| CasMG6 RuvCII | 92 |
| CasMG6 RuvCIII | 93 |
| dCasMG6 mutations (comprise or correspond to position in SEQ ID NO: 87) | D836A, E934A, D1185A |
| Enhanced CasMG6 mutations (comprise or correspond to position in SEQ ID NO: 87) | D508N, Q516K, C921A, D928N, V945F/Q, R994K, N1043D, I1053F/Y, Y1167F, and/or A1196G |
| Enhanced CR CasMG6 Mutations (comprise or correspond to position in SEQ ID NO: 87) | L787I |
| CasMG7 | 94 |
| CasMG7 Direct repeat (residues 18-36 underlined) | 95 |
| tracrRNA sequence of the CasMG7 locus | 96 |
| Residues 18-36 of SEQ ID NO: 95 | 97 |
| CasMG7 RuvCI | 98 |
| CasMG7 RuvCII | 99 |
| CasMG7 RuvCIII | 100 |
| dCasMG7 mutations (comprise or correspond to position in SEQ ID NO: 94) | D865A, E950A, D1198A |
| Enhanced CasMG7 mutations (comprise or correspond to position in SEQ ID NO: 94) | L464I, D513N, Q521K, D944N, F961Q, L1012K, D1061N, I1071F/Y, and/or A1209G |
| Enhanced CR CasMG7 Mutation (comprise or correspond to position in SEQ ID NO: 94) | L816I |
| CasMG8 | 101 |
| CasMG8 Direct Repeat (residues 18-36 underlined) | 102 |
| tracrRNA of the CasMG8 locus | 103 |
| Residues 18-36 of SEQ ID NO: 102 | 104 |
| CasMG8 RuvCI | 105 |
| CasMG8 RuvCII | 106 |
| CasMG8 RuvCIII | 107 |
| dCasMG8 mutations (comprise or correspond to position in SEQ ID NO: 101) | D827A, E916A, D1165A |
| Enhanced CasMG8 mutations (comprise or | L294F, F927Q, F948L, D957E, |

TABLE 1-continued

Biological sequences and mutations referred to in the specification and claims

| Name | SEQ ID NO or Mutation |
|---|---|
| correspond to position in SEQ ID NO: 101) | D1032N, F1042Y, and/or K1194L |
| CasMG9 | 108 |
| CasMG9 Direct repeat (residues 18-36 underlined) | 109 |
| tracrRNA sequence of the CasMG9 locus | 110 |
| Residues 18-36 of SEQ ID NO: 109 | 111 |
| CasMG9 RuvCI | 112 |
| CasMG9 RuvCII | 113 |
| CasMG9 RuvCIII | 114 |
| dCasMG9 mutations (comprise or correspond to position in SEQ ID NO: 108) | D828A, E917A, and/or D1167A |
| Enhanced CasMG9 mutations (comprise or correspond to position in SEQ ID NO: 108) | L295F, F928Q, D1034N, F1044Y, and/or A1196L |
| CasMG10 | 115 |
| CasMG10 Direct repeat (residues 17-36 underlined) | 116 |
| tracrRNA of the CasMG10 locus | 117 |
| Residues 17-36 of SEQ ID NO: 116 | 118 |
| CasMG10 RuvCI | 119 |
| CasMG10 RuvCII | 120 |
| CasMG10 RuvCIII | 121 |
| dCasMG10 mutations (comprise or correspond to position in SEQ ID NO: 115) | I837A, E920A, and/or S1145A |
| Enhanced CasMG10 mutations (comprise or correspond to position in SEQ ID NO: 115) | I277F, V411I, S461N, V907A, K931F/Q, F952L, R980K, D1030N, F1038Y, and/or L1156G |
| Enhanced CR CasMG10 Mutations (comprise or correspond to position in SEQ ID NO: 115) | L789I |

EXAMPLES

The following examples are not intended to limit the scope of what the inventors regard as their invention.

Example 1—Nuclease Effector Sequence

Sequence data from samples of microbial communities is analyzed to identify new Class 2 CRISPR-Cas systems. Candidate sequences are proposed based on proximity to CRISPR arrays and the presence of conserved sequence domains.

A nuclease sequence now termed CasMG1 is shown in SEQ ID NO: 1. CasMG1 contains a RuvC split domain in the C-terminal region (RuvC-I (SEQ ID NO: 54), RuvC-II (SEQ ID NO: 55), and RuvC-III (SEQ ID NO: 56)).

A nuclease sequence now termed CasMG2 is shown in SEQ ID NO: 59. CasMG2 contains a RuvC split domain in the C-terminal region (RuvC-I (SEQ ID NO: 63), RuvC-II (SEQ ID NO: 64), and RuvC-III (SEQ ID NO: 65)).

A nuclease sequence now termed CasMG3 is shown in SEQ ID NO: 66. CasMG3 contains a RuvC split domain in the C-terminal region (RuvC-I (SEQ ID NO: 70), RuvC-II (SEQ ID NO: 71), and RuvC-III (SEQ ID NO: 72)).

A nuclease sequence now termed CasMG4 is shown in SEQ ID NO: 73. CasMG4 contains a RuvC split domain in the C-terminal region (RuvC-I (SEQ ID NO: 77), RuvC-II (SEQ ID NO: 78), and RuvC-III (SEQ ID NO: 79)).

A nuclease sequence now termed CasMG5 is shown in SEQ ID NO: 80. CasMG5 contains a RuvC split domain in the C-terminal region (RuvC-I (SEQ ID NO: 84), RuvC-II (SEQ ID NO: 85), and RuvC-III (SEQ ID NO: 86)).

A nuclease sequence now termed CasMG6 is shown in SEQ ID NO: 87. CasMG6 contains a RuvC split domain in the C-terminal region (RuvC-I (SEQ ID NO: 91), RuvC-II (SEQ ID NO: 92), and RuvC-III (SEQ ID NO: 93)).

A nuclease sequence now termed CasMG7 is shown in SEQ ID NO: 94. CasMG7 contains a RuvC split domain in the C-terminal region (RuvC-I (SEQ ID NO: 98), RuvC-II (SEQ ID NO: 99), and RuvC-III (SEQ ID NO: 100)).

A nuclease sequence now termed CasMG8 is shown in SEQ ID NO: 101. CasMG8 contains a RuvC split domain in the C-terminal region (RuvC-I (SEQ ID NO: 105), RuvC-II (SEQ ID NO: 106), and RuvC-III (SEQ ID NO: 107)).

A nuclease sequence now termed CasMG9 is shown in SEQ ID NO: 108. CasMG9 contains a RuvC split domain in the C-terminal region (RuvC-I (SEQ ID NO: 112), RuvC-II (SEQ ID NO: 113), and RuvC-III (SEQ ID NO: 114)).

A nuclease sequence now termed CasMG10 is shown in SEQ ID NO: 115. CasMG10 contains a RuvC split domain in the C-terminal region (RuvC-I (SEQ ID NO: 119), RuvC-II (SEQ ID NO: 120), and RuvC-TTT (SEQ ID NO: 121)).

Example 2—crRNA

A CRISPR array adjacent to the nucleases of Example 1 points functional RNA components. Direct repeat (DR) sequences flanking many spacer sequences about 22 residues long of the CRISPR array are shown in SEQ ID NO: 2 (CasMG1), SEQ ID NO: 60 (CasMG2), SEQ ID NO: 67 (CasMG3), SEQ ID NO: 74 (CasMG4), SEQ ID NO: 81 (CasMG5), SEQ ID NO: 88 (CasMG6), SEQ ID NO: 95 (CasMG7), SEQ ID NO: 102 (CasMG8), SEQ ID NO: 109 (CasMG9), and SEQ ID NO: 116 (CasMG10).

Example 3—Single Guide Sequence

CasMG1: A vector is made having an Arabidopis U6 (Pol III) promoter driving expression of an RNA made up of the RNA encoded by SEQ ID NO: 15 sequence fused to a 22 residue guide RNA directed to the Phytoene desaturase (PDS) gene of soybean.

CasMG2: A vector is made having an Arabidopis U6 (Pol III) promoter driving expression of an RNA made up of the RNA encoded by SEQ ID NO: 62 sequence fused to a 22 residue guide RNA directed to the Phytoene desaturase (PDS) gene of soybean.

CasMG3: A vector is made having an Arabidopis U6 (Pol III) promoter driving expression of an RNA made up of the RNA encoded by SEQ ID NO: 69 sequence fused to a 22 residue guide RNA directed to the Phytoene desaturase (PDS) gene of soybean.

CasMG4: A vector is made having an Arabidopis U6 (Pol III) promoter driving expression of an RNA made up of the RNA encoded by SEQ ID NO: 76 sequence fused to a 22 residue guide RNA directed to the Phytoene desaturase (PDS) gene of soybean.

CasMG5: A vector is made having an Arabidopis U6 (Pol III) promoter driving expression of an RNA made up of the RNA encoded by SEQ ID NO: 83 sequence fused to a 22 residue guide RNA directed to the Phytoene desaturase (PDS) gene of soybean.

CasMG6: A vector is made having an Arabidopis U6 (Pol III) promoter driving expression of an RNA made up of the RNA encoded by SEQ ID NO: 90 sequence fused to a 22 residue guide RNA directed to the Phytoene desaturase (PDS) gene of soybean.

CasMG7: A vector is made having an Arabidopis U6 (Pol III) promoter driving expression of an RNA made up of the RNA encoded by SEQ ID NO: 97 sequence fused to a 22 residue guide RNA directed to the Phytoene desaturase (PDS) gene of soybean.

CasMG8: A vector is made having an Arabidopis U6 (Pol III) promoter driving expression of an RNA made up of the RNA encoded by SEQ ID NO: 104 sequence fused to a 22 residue guide RNA directed to the Phytoene desaturase (PDS) gene of soybean.

CasMG9: A vector is made having an Arabidopis U6 (Pol III) promoter driving expression of an RNA made up of the RNA encoded by SEQ ID NO: 111 sequence fused to a 22 residue guide RNA directed to the Phytoene desaturase (PDS) gene of soybean.

CasMG10: A vector is made having an Arabidopis U6 (Pol III) promoter driving expression of an RNA made up of the RNA encoded by SEQ ID NO: 118 sequence fused to a 22 residue guide RNA directed to the Phytoene desaturase (PDS) gene of soybean.

Example 4—CasMG

An effector nuclease vector is made by making a vector having a 35S promoter operably linked to drive expression of a soybean codon-optimized mRNA encoding an amino acid sequence of CasMG1, CasMG2, CasMG3, CasMG4, CasMG5, CasMG6, CasMG7, CasMG8, CasMG9, or CasMG10, flanked at both the N and C termini by nuclear localization sequences.

Example 5—Genome Editing

The vectors of examples 3 and 4 are co-transformed into a soybean plant. Transformed plants are regenerated, and the albino phenotype of PDS mutants is observed. The PDS genomic sequence of plants material with albino phenotype is sequenced. Mutations in the PDS gene are found.

Although the foregoing invention has been described in some detail by way of illustration and example for purposes of clarity of understanding, it will be obvious that certain changes and modifications may be practiced within the scope of the appended claims.

What is claimed is:

1. A composition comprising:
    a) a CasMG2 fusion polypeptide comprising a CasMG2 polypeptide fused to a heterologous polypeptide or a nucleic acid molecule encoding the CasMG2 fusion polypeptide, wherein the CasMG2 polypeptide has 90% or more identity to the amino acid sequence set forth in SEQ ID NO: 59, and wherein the CasMG2 fusion polypeptide comprises the RuvC-I domain of SEQ ID NO: 63, the RuvC-II domain of SEQ ID NO: 64, and the RuvC-III domain of SEQ ID NO 65; and
    b) a CasMG2 guide RNA, or one or more DNA molecules encoding the CasMG2 guide RNA, wherein the CasMG2 guide RNA comprises a guide sequence with complementarity to a eukaryotic nucleic acid;
    wherein the CasMG2 polypeptide or a nucleic acid molecule encoding said polypeptide is respectively combined with the CasMG2 guide RNA or with one or more DNA molecules encoding the guide RNA.

2. The composition of claim 1, wherein the CasMG2 polypeptide comprises an amino acid sequence having 95%, 97%, 98%, 99%, 99.5%, 99.8%, 99.9%, or more identity to the amino acid sequence set forth in SEQ ID NO: 59.

3. The composition of claim 1, wherein the CasMG2 guide RNA is a single guide RNA.

4. The composition of claim 1, wherein the CasMG2 guide RNA comprises an RNA encoded by SEQ ID NO: 62.

5. The composition of claim 1, wherein the CasMG2 polypeptide is a nickase that can cleave only one strand of a double-stranded target nucleic acid molecule.

6. The composition of claim 1, wherein the CasMG2 polypeptide is:
    a catalytically inactive CasMG2 Polypeptide.

7. The composition of claim 1, wherein:
    the CasMG2 polypeptide comprises one or more mutations selected from R545K, S957A, Q981F, T1041V, N1082D, F1092Y, and/or Y1205F of SEQ ID NO: 59.

8. The composition of claim 1, further comprising a DNA donor template.

9. A CasMG fusion polypeptide comprising a CasMG polypeptide fused to a heterologous polypeptide, wherein the CasMG polypeptide is a CasMG2 polypeptide, wherein the CasMG2 polypeptide has 90% or more identity to the amino acid sequence set forth in SEQ ID NO: 59, and wherein the CasMG2 fusion polypeptide comprises the RuvC-I domain of SEQ ID NO: 63, the RuvC-II domain of SEQ ID NO: 64, and the RuvC-III domain of SEQ ID NO 65.

10. The CasMG fusion polypeptide of claim 9, wherein the CasMG polypeptide comprises:
    a CasMG2 amino acid sequence having 95% or more identity to the amino acid sequence set forth in SEQ ID NO: 59.

11. The CasMG fusion polypeptide of claim 9, wherein the heterologous polypeptide is operably linked to the N-terminus and/or the C-terminus of the CasMG polypeptide.

12. The CasMG fusion polypeptide of claim 9, wherein the heterologous polypeptide comprises a nuclear localization signal.

13. The CasMG fusion polypeptide of claim 9, wherein the heterologous polypeptide exhibits an enzymatic activity that modifies target DNA or a target polypeptide associated with a target nucleic acid.

14. The CasMG fusion polypeptide of claim 9, wherein the heterologous polypeptide protein increases or decreases transcription of a gene when the CasMG fusion polypeptide is bound to the gene and a guide RNA.

15. A nucleic acid molecule encoding the CasMG fusion polypeptide of claim 9.

16. A eukaryotic cell comprising:
    a) a CasMG fusion polypeptide of claim 9 or a nucleic acid molecule encoding the CasMG fusion polypeptide, wherein the CasMG fusion polypeptide is a CasMG2 fusion polypeptide, and/or
    b) a CasMG guide RNA of or a nucleic acid molecule encoding the CasMG guide RNA, wherein the CasMG guide RNA is a CasMG2 guide RNA;
    wherein the eukaryotic cell is a plant cell, an algal cell, a fungal cell, an invertebrate cell, an ungulate cell, an avian cell, a fish cell, an amphibian cell, a reptile cell, a parasite cell, a rodent cell, a canine cell, a feline cell, a non-human primate cell, or an artificial cell.

17. A method of modifying a target nucleic acid, the method comprising contacting the target nucleic acid with:
    a) a CasMG fusion polypeptide, wherein the CasMG fusion polypeptide is a CasMG2 fusion polypeptide, wherein the CasMG2 polypeptide has 90% or more identity to the amino acid sequence set forth in SEQ ID NO: 59, and wherein the CasMG2 fusion polypeptide comprises the RuvC-I domain of SEQ ID NO: 63, the RuvC-II domain of SEQ ID NO: 64, and the RuvC-III domain of SEQ ID NO 65; and
    b) a CasMG guide RNA comprising a guide sequence that hybridizes to a target sequence of the target nucleic acid, wherein the CasMG guide RNA is a CasMG2 guide RNA, wherein said contacting results in modification of the target nucleic acid by the CasMG polypeptide.

18. The method of claim 17, wherein the CasMG fusion polypeptide comprises:
    a CasMG2 amino acid sequence having 95% or more identity to the amino acid sequence set forth in SEQ ID NO: 59.

19. The method of claim 17, wherein said contacting comprises: introducing into a cell: (a) the CasMG fusion polypeptide, or a nucleic acid molecule encoding the CasMG fusion polypeptide, and (b) the CasMG guide RNA, or a nucleic acid molecule encoding the CasMG guide RNA.

20. The method of claim 17, wherein:
    the CasMG2 guide RNA comprises SEQ ID NO: 62.

* * * * *

SEQUENCE LISTING

```
<160> NUMBER OF SEQ ID NOS: 121

<210> SEQ ID NO 1
<211> LENGTH: 1170
<212> TYPE: PRT
<213> ORGANISM: Unknown
<220> FEATURE:
<223> OTHER INFORMATION: bacterial

<400> SEQUENCE: 1

Met Glu Arg Phe Thr Lys Lys Tyr Glu Leu Thr Lys Asn Leu Cys Phe
1               5                   10                  15

Glu Leu Val Pro Val Gly Lys Thr Arg Glu Asn Ile Glu Lys Ser Gly
            20                  25                  30

Tyr Ile Ser His Asp Asp Lys Arg Asn Ala Asp Ala Glu Arg Val Lys
        35                  40                  45

Pro Ile Phe Asp Lys Val His Lys Asn Ile Ile Thr Glu Gly Leu Gly
    50                  55                  60

Asn Val Asp Lys Lys Gln Leu Ser Arg Leu Ile Glu Ser Tyr Met Glu
65                  70                  75                  80

Cys Val Asn Ala Gly Lys Glu Tyr Asp Tyr Ser Ile Met Leu Glu Tyr
                85                  90                  95

Ile Ser Ser Val Leu Thr Glu Ser Glu Ala Tyr Lys Lys Ile Arg Thr
            100                 105                 110

Asn Ala Asp Ile Leu Asn Val Ala Leu Glu Ile Ala Gln Asn Asp Glu
        115                 120                 125
```

```
Glu His Glu Leu Leu Glu Ser Phe Lys Gly Phe Met Met Tyr Phe Ser
    130                 135                 140

Asn Tyr His Thr Ala Arg Glu Lys Leu Tyr Ala Ala Asp Gly Lys Phe
145                 150                 155                 160

Gly Ser Val Ala Ala Arg Leu Ile Lys Asp Asn Leu Pro Ile Phe Val
                165                 170                 175

Tyr Asn Tyr His Ile Met Lys Gln Phe Ser Gly Ser Met Val Ala Leu
                180                 185                 190

Met Asp Glu Leu Lys Leu Ser Glu Asn Leu Asp Val Tyr Phe Ser Pro
            195                 200                 205

Glu His Tyr Pro Cys Thr Asn Glu Glu Ile Thr Leu Tyr Asn Thr Ile
    210                 215                 220

Ile Ser Gly Ile Val Lys Glu Asp Gly Asn His Ile Lys Gly Ile Asn
225                 230                 235                 240

Gln Leu Ile Asn Glu Thr Asn Gln Ser Glu Asn Gly Glu Lys Lys Leu
                245                 250                 255

Ser Leu Met Lys Pro Leu Lys Lys Met Ile Leu Phe Glu Arg Ile Ala
                260                 265                 270

Met Ser Phe Ala Tyr Glu Ser Phe Leu Asn Asp Asp Val Leu Lys
    275                 280                 285

Ala Leu Gln Ser Phe Glu Lys Asp Phe Lys Ala Glu Met Glu Ser Phe
290                 295                 300

Tyr His Ile Glu Ser Leu Lys Gly Ile Tyr Ile Lys Ser Ser Tyr Ile
305                 310                 315                 320

Thr Glu Leu Ser Gln Phe Cys Tyr His Asp Trp Ser Tyr Val Asp Arg
                325                 330                 335

Ala Arg Arg Ala Leu Tyr Asp His Glu Phe Tyr Ile Asn Asn Thr Lys
                340                 345                 350

Met Thr Lys Lys Gln Glu Lys Glu Arg Asp Ser Leu Leu Lys Gln Ser
                355                 360                 365

Tyr Val Glu Leu Ser Glu Ile Ala Arg Ala Cys Val Phe Val Ser Gln
370                 375                 380

Glu Pro Ala Leu Ile Asn Ala Tyr Tyr Glu Gln Ile Pro Ser Leu Tyr
385                 390                 395                 400

Ala Lys Tyr Lys Gly Tyr Cys Glu Lys Phe Lys Leu Leu Lys Thr
                405                 410                 415

Lys Arg Lys Lys Ser Leu Lys Asn Asp Asn Glu Leu Ile Gly Val Ile
                420                 425                 430

Lys Asn Met Leu Asp Thr Leu Lys Leu Ile Glu Asn Arg Leu Lys Ser
                435                 440                 445

Leu Tyr Tyr Glu Cys Ser Glu Lys Gln Thr Ala Phe Tyr Asp Gly Ala
    450                 455                 460

Ser Ala Ile Leu Glu Glu Leu Glu Met Leu Asn Lys Leu Tyr Asn Met
465                 470                 475                 480

Thr Arg Asn Tyr Ile Thr Ala Lys Pro Tyr Ser Lys Asp Lys Ile Gln
                485                 490                 495

Leu Thr Phe Gly Thr Ser Ser Phe Met Gln Gly Trp Asp Arg Asp Lys
                500                 505                 510

Lys Asp Ile Asn Met Ala Asn Ile Leu Leu Lys Asp Gly Lys Tyr Tyr
                515                 520                 525

Leu Ala Val Ala Asp Met Ser Phe Arg Lys Val Leu Val Ala Gly His
530                 535                 540
```

```
Cys Ser Thr Asp Asp Tyr Tyr Glu Ser Ile Glu Tyr Lys Gln Phe Thr
545                 550                 555                 560

Lys Val Asn Met Asn Leu Pro Arg Ile Val Lys Ser Lys Ala Ala Arg
            565                 570                 575

Glu Glu Phe Glu Leu Thr Glu Asn Ile Ser Arg Ile Leu Asn Thr Gly
                580                 585                 590

Ser Tyr Lys Val Gly Pro Thr Phe Ser Lys Asp Asp Leu Asn Ala Leu
        595                 600                 605

Ile Glu Phe Tyr Lys Gly Val Leu Ser Lys Arg Tyr Ser Glu Phe Glu
610                 615                 620

His Asn Tyr Lys Asp Ser Ser Glu Tyr Gln Asn Ile Lys Glu Phe Phe
625                 630                 635                 640

Asp Asp Val Thr Arg Cys Cys Tyr Asn Leu Gly Arg Ser Arg Ile Asp
                645                 650                 655

Ala Ser Tyr Ile Asn Glu Met Val Asp Lys Gly Asn Leu His Leu Phe
                660                 665                 670

Glu Ile Thr Ser Arg Glu Leu Arg Lys Gln Arg Asn Glu Lys Met Asn
            675                 680                 685

Lys Asn Ala Leu Leu Phe Lys Ala Ile Phe Glu Asp Ser Ala Asn Ile
690                 695                 700

Lys Leu Leu Ala Gly Ala Lys Met Tyr Tyr Arg Lys Val Lys Ile Arg
705                 710                 715                 720

Glu Glu Asp Arg Ile Ile His Lys Ala Asn Glu Lys Ile Lys Asn Lys
                725                 730                 735

Asn Pro Leu Ser Lys Asn Gln Glu Val Leu Phe Pro Tyr Asp Ile Ile
                740                 745                 750

Lys Asn Lys Arg Phe Thr Val Glu Gln Phe Ser Leu His Val Cys Cys
                755                 760                 765

Ala Ile Asn Pro Val Leu Asp Asp Lys Leu Met Asn Asp Glu Val Asn
770                 775                 780

Gln Phe Ile Arg Glu His Glu Asp Ile His Val Leu Gly Ile Asn Arg
785                 790                 795                 800

Gly Glu Asn Asn Leu Ile Tyr Ala Val Ile Asp Ala Ala Gly His
                805                 810                 815

Ile Val Glu Gln Arg Asn Leu Asn Val Ile Thr Tyr Lys Asn Gln Asn
                820                 825                 830

Gly Lys Glu Cys Met Cys Asp Tyr Gly Glu Leu Leu Arg Arg Arg Glu
        835                 840                 845

Met Glu Asn Asp Ala Lys Gln Lys Asn Trp Gln Thr Val Gly Asn Ile
        850                 855                 860

Lys Thr Leu Lys Glu Gly Tyr Leu Ser Gln Ala Leu His Glu Ile Thr
865                 870                 875                 880

Gln Leu Met Phe Lys Tyr Asn Ala Val Val Ala Ile Glu Asp Leu Ser
                885                 890                 895

Gln Ser Phe Ile Arg Asp Arg Ala Lys Ile Asp Arg Asn Ile Tyr Gln
                900                 905                 910

Lys Phe Glu Glu Met Leu Tyr Lys Arg Leu Asn Tyr Leu Val Thr Glu
            915                 920                 925

Asn Thr Leu Thr Gly Gln Ala Gly Ser Val Asn Asn Gly Tyr Gln Leu
            930                 935                 940

Val Asn Lys Phe Glu Ser Met Glu Lys Ile Gly Ile Gln Asn Gly Phe
945                 950                 955                 960
```

-continued

```
Ile Phe Lys Ile Ser Pro Tyr Met Thr Ser Asn Ile Asp Pro Thr Thr
            965                 970                 975

Gly Phe Val Ala Pro Phe Lys Cys Asn Thr Lys Gln Glu Met Met
        980                 985                 990

Ala Phe Phe Ala Ser Phe Thr Asp Ile Cys Tyr Asn Gly Ser Glu Phe
        995                1000                1005

Glu Phe Gln Thr Asn Ala Ser Cys Phe Ala Ser Asn Tyr Lys Gly
    1010                1015                1020

Lys Thr Asp Trp Thr Ile Val Thr His Gly Lys Arg Val Asp Tyr
    1025                1030                1035

Gly Ala Asp Lys Thr Val Thr Trp Val Asp Val Thr Glu Asp Met
    1040                1045                1050

Val Asn Leu Cys Asn Gln Tyr Gly Ile Asn Thr Glu Ser Asn Leu
    1055                1060                1065

Arg Lys Gln Ile Leu Glu Ala Asn Asn Leu Ala Phe Tyr Lys Glu
    1070                1075                1080

Leu Tyr Arg Leu Phe Asn Leu Thr Val Lys Met His Asn Lys Val
    1085                1090                1095

Gly Asp Asp Cys Ile Ile Ile Ser Pro Val Lys Asn Ser Asn Gly
    1100                1105                1110

Glu Phe Tyr Met Ser Gly Ser Asp Asp Thr Leu Pro Leu Asn Ala
    1115                1120                1125

Asp Ala Asn Gly Ala Tyr His Ile Ala Lys Lys Cys Met Ile Tyr
    1130                1135                1140

Leu Asn Arg Ile Arg Glu Ala Glu Asp Met Arg Pro Lys Leu Gly
    1145                1150                1155

Ile Lys Asn Glu Glu Trp Leu Ser Tyr Ile Gln Gln
    1160                1165                1170

<210> SEQ ID NO 2
<211> LENGTH: 36
<212> TYPE: DNA
<213> ORGANISM: Unknown
<220> FEATURE:
<223> OTHER INFORMATION: bacterial

<400> SEQUENCE: 2
gtctataagt aagtaaaatg cctactgtgt gtaggt                                 36

<210> SEQ ID NO 3
<211> LENGTH: 84
<212> TYPE: PRT
<213> ORGANISM: Artificial
<220> FEATURE:
<223> OTHER INFORMATION: synthetic

<400> SEQUENCE: 3

Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80
```

Asp Ser Arg Ala

<210> SEQ ID NO 4
<211> LENGTH: 57
<212> TYPE: PRT
<213> ORGANISM: Artificial
<220> FEATURE:
<223> OTHER INFORMATION: synthetic

<400> SEQUENCE: 4

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
        50                  55

<210> SEQ ID NO 5
<211> LENGTH: 85
<212> TYPE: PRT
<213> ORGANISM: Artificial
<220> FEATURE:
<223> OTHER INFORMATION: synthetic

<400> SEQUENCE: 5

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 6
<211> LENGTH: 76
<212> TYPE: PRT
<213> ORGANISM: Artificial
<220> FEATURE:
<223> OTHER INFORMATION: synthetic

<400> SEQUENCE: 6

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 7

```
<211> LENGTH: 76
<212> TYPE: PRT
<213> ORGANISM: Artificial
<220> FEATURE:
<223> OTHER INFORMATION: synthetic

<400> SEQUENCE: 7

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 8
<211> LENGTH: 72
<212> TYPE: PRT
<213> ORGANISM: Artificial
<220> FEATURE:
<223> OTHER INFORMATION: synthetic

<400> SEQUENCE: 8

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Leu Phe Cys Ser Phe Arg Ile
    50                  55                  60

Ser Ala Ser Val Ala Thr Ala Cys
65                  70

<210> SEQ ID NO 9
<211> LENGTH: 69
<212> TYPE: PRT
<213> ORGANISM: Artificial
<220> FEATURE:
<223> OTHER INFORMATION: synthetic

<400> SEQUENCE: 9

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val
65

<210> SEQ ID NO 10
<211> LENGTH: 77
<212> TYPE: PRT
<213> ORGANISM: Artificial
<220> FEATURE:
```

<223> OTHER INFORMATION: synthetic

<400> SEQUENCE: 10

Met Ala Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Val Cys
65                  70                  75

<210> SEQ ID NO 11
<211> LENGTH: 57
<212> TYPE: PRT
<213> ORGANISM: Artificial
<220> FEATURE:
<223> OTHER INFORMATION: synthetic

<400> SEQUENCE: 11

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 12
<211> LENGTH: 65
<212> TYPE: PRT
<213> ORGANISM: Artificial
<220> FEATURE:
<223> OTHER INFORMATION: synthetic

<400> SEQUENCE: 12

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Thr Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65

<210> SEQ ID NO 13
<211> LENGTH: 72
<212> TYPE: PRT
<213> ORGANISM: Artificial
<220> FEATURE:
<223> OTHER INFORMATION: synthetic

<400> SEQUENCE: 13

Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser
65                  70

<210> SEQ ID NO 14
<211> LENGTH: 60
<212> TYPE: RNA
<213> ORGANISM: Artificial
<220> FEATURE:
<223> OTHER INFORMATION: synthetic

<400> SEQUENCE: 14
auaaaaauua aguggacauu uuacuuguga ugugauauua ucguaacaua guuuaaaaaa    60

<210> SEQ ID NO 15
<211> LENGTH: 21
<212> TYPE: DNA
<213> ORGANISM: Unknown
<220> FEATURE:
<223> OTHER INFORMATION: bacterial

<400> SEQUENCE: 15
aaatgcctac tgtgtgtagg t                                              21

<210> SEQ ID NO 16
<211> LENGTH: 20
<212> TYPE: PRT
<213> ORGANISM: Unknown
<220> FEATURE:
<223> OTHER INFORMATION: synthetic
<220> FEATURE:
<221> NAME/KEY: VARIANT
<222> LOCATION: (4)..(4)
<223> OTHER INFORMATION: Xaa is independently selected from lysine,
      histidine, and arginine
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: VARIANT
<222> LOCATION: (11)..(11)
<223> OTHER INFORMATION: Xaa is independently selected from lysine,
      histidine, and arginine
<220> FEATURE:
<221> NAME/KEY: VARIANT
<222> LOCATION: (15)..(15)
<223> OTHER INFORMATION: Xaa is independently selected from lysine,
      histidine, and arginine
<220> FEATURE:
<221> NAME/KEY: VARIANT
<222> LOCATION: (19)..(19)
<223> OTHER INFORMATION: Xaa is independently selected from lysine,
      histidine, and arginine

<400> SEQUENCE: 16

Gly Leu Phe Xaa Ala Leu Leu Xaa Leu Leu Xaa Ser Leu Trp Xaa Leu
1               5                   10                  15

Leu Leu Xaa Ala
            20

<210> SEQ ID NO 17
<211> LENGTH: 20

```
<212> TYPE: PRT
<213> ORGANISM: Artificial
<220> FEATURE:
<223> OTHER INFORMATION: synthetic

<400> SEQUENCE: 17

Gly Leu Phe His Ala Leu Leu His Leu Leu His Ser Leu Trp His Leu
1               5                   10                  15

Leu Leu His Ala
            20

<210> SEQ ID NO 18
<211> LENGTH: 16
<212> TYPE: PRT
<213> ORGANISM: Artificial
<220> FEATURE:
<223> OTHER INFORMATION: synthetic

<400> SEQUENCE: 18

Lys Arg Pro Ala Ala Thr Lys Lys Ala Gly Gln Ala Lys Lys Lys Lys
1               5                   10                  15

<210> SEQ ID NO 19
<211> LENGTH: 9
<212> TYPE: PRT
<213> ORGANISM: Artificial
<220> FEATURE:
<223> OTHER INFORMATION: synthetic

<400> SEQUENCE: 19

Pro Ala Ala Lys Arg Val Lys Leu Asp
1               5

<210> SEQ ID NO 20
<211> LENGTH: 11
<212> TYPE: PRT
<213> ORGANISM: Artificial
<220> FEATURE:
<223> OTHER INFORMATION: synthetic

<400> SEQUENCE: 20

Arg Gln Arg Arg Asn Glu Leu Lys Arg Ser Pro
1               5                   10

<210> SEQ ID NO 21
<211> LENGTH: 38
<212> TYPE: PRT
<213> ORGANISM: Artificial
<220> FEATURE:
<223> OTHER INFORMATION: synthetic

<400> SEQUENCE: 21

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
                20                  25                  30

Arg Asn Gln Gly Gly Tyr
            35

<210> SEQ ID NO 22
<211> LENGTH: 42
<212> TYPE: PRT
<213> ORGANISM: Artificial
<220> FEATURE:
<223> OTHER INFORMATION: synthetic
```

```
<400> SEQUENCE: 22

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 23
<211> LENGTH: 8
<212> TYPE: PRT
<213> ORGANISM: Artificial
<220> FEATURE:
<223> OTHER INFORMATION: synthetic

<400> SEQUENCE: 23

Val Ser Arg Lys Arg Pro Arg Pro
1               5

<210> SEQ ID NO 24
<211> LENGTH: 8
<212> TYPE: PRT
<213> ORGANISM: Artificial
<220> FEATURE:
<223> OTHER INFORMATION: synthetic

<400> SEQUENCE: 24

Pro Pro Lys Lys Ala Arg Glu Asp
1               5

<210> SEQ ID NO 25
<211> LENGTH: 8
<212> TYPE: PRT
<213> ORGANISM: Artificial
<220> FEATURE:
<223> OTHER INFORMATION: synthetic

<400> SEQUENCE: 25

Pro Gln Pro Lys Lys Lys Pro Leu
1               5

<210> SEQ ID NO 26
<211> LENGTH: 12
<212> TYPE: PRT
<213> ORGANISM: Artificial
<220> FEATURE:
<223> OTHER INFORMATION: synthetic

<400> SEQUENCE: 26

Ser Ala Leu Ile Lys Lys Lys Lys Lys Met Ala Pro
1               5                   10

<210> SEQ ID NO 27
<211> LENGTH: 5
<212> TYPE: PRT
<213> ORGANISM: Artificial
<220> FEATURE:
<223> OTHER INFORMATION: synthetic

<400> SEQUENCE: 27

Asp Arg Leu Arg Arg
1               5

<210> SEQ ID NO 28
<211> LENGTH: 7
```

```
<212> TYPE: PRT
<213> ORGANISM: Artificial
<220> FEATURE:
<223> OTHER INFORMATION: synthetic

<400> SEQUENCE: 28

Pro Lys Gln Lys Lys Arg Lys
1               5

<210> SEQ ID NO 29
<211> LENGTH: 10
<212> TYPE: PRT
<213> ORGANISM: Artificial
<220> FEATURE:
<223> OTHER INFORMATION: synthetic

<400> SEQUENCE: 29

Arg Lys Leu Lys Lys Lys Ile Lys Lys Leu
1               5                   10

<210> SEQ ID NO 30
<211> LENGTH: 10
<212> TYPE: PRT
<213> ORGANISM: Artificial
<220> FEATURE:
<223> OTHER INFORMATION: synthetic

<400> SEQUENCE: 30

Arg Glu Lys Lys Lys Phe Leu Lys Arg Arg
1               5                   10

<210> SEQ ID NO 31
<211> LENGTH: 20
<212> TYPE: PRT
<213> ORGANISM: Artificial
<220> FEATURE:
<223> OTHER INFORMATION: synthetic

<400> SEQUENCE: 31

Lys Arg Lys Gly Asp Glu Val Asp Gly Val Asp Glu Val Ala Lys Lys
1               5                   10                  15

Lys Ser Lys Lys
            20

<210> SEQ ID NO 32
<211> LENGTH: 17
<212> TYPE: PRT
<213> ORGANISM: Artificial
<220> FEATURE:
<223> OTHER INFORMATION: synthetic

<400> SEQUENCE: 32

Arg Lys Cys Leu Gln Ala Gly Met Asn Leu Glu Ala Arg Lys Thr Lys
1               5                   10                  15

Lys

<210> SEQ ID NO 33
<211> LENGTH: 11
<212> TYPE: PRT
<213> ORGANISM: Artificial
<220> FEATURE:
<223> OTHER INFORMATION: synthetic

<400> SEQUENCE: 33

Tyr Gly Arg Lys Lys Arg Arg Gln Arg Arg
1               5                   10
```

<210> SEQ ID NO 34
<211> LENGTH: 12
<212> TYPE: PRT
<213> ORGANISM: Artificial
<220> FEATURE:
<223> OTHER INFORMATION: synthetic

<400> SEQUENCE: 34

Arg Arg Gln Arg Arg Thr Ser Lys Leu Met Lys Arg
1               5                   10

<210> SEQ ID NO 35
<211> LENGTH: 27
<212> TYPE: PRT
<213> ORGANISM: Artificial
<220> FEATURE:
<223> OTHER INFORMATION: synthetic

<400> SEQUENCE: 35

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 36
<211> LENGTH: 33
<212> TYPE: PRT
<213> ORGANISM: Artificial
<220> FEATURE:
<223> OTHER INFORMATION: synthetic

<400> SEQUENCE: 36

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 37
<211> LENGTH: 16
<212> TYPE: PRT
<213> ORGANISM: Artificial
<220> FEATURE:
<223> OTHER INFORMATION: synthetic

<400> SEQUENCE: 37

Arg Gln Ile Lys Ile Trp Phe Gln Asn Arg Arg Met Lys Trp Lys Lys
1               5                   10                  15

<210> SEQ ID NO 38
<211> LENGTH: 11
<212> TYPE: PRT
<213> ORGANISM: Artificial
<220> FEATURE:
<223> OTHER INFORMATION: synthetic

<400> SEQUENCE: 38

Tyr Gly Arg Lys Lys Arg Arg Gln Arg Arg Arg
1               5                   10

<210> SEQ ID NO 39
<211> LENGTH: 9
<212> TYPE: PRT
<213> ORGANISM: Artificial

```
<220> FEATURE:
<223> OTHER INFORMATION: synthetic

<400> SEQUENCE: 39

Arg Lys Lys Arg Arg Gln Arg Arg
1               5

<210> SEQ ID NO 40
<211> LENGTH: 11
<212> TYPE: PRT
<213> ORGANISM: Artificial
<220> FEATURE:
<223> OTHER INFORMATION: synthetic

<400> SEQUENCE: 40

Tyr Gly Arg Lys Lys Arg Arg Gln Arg Arg
1               5                   10

<210> SEQ ID NO 41
<211> LENGTH: 8
<212> TYPE: PRT
<213> ORGANISM: Artificial
<220> FEATURE:
<223> OTHER INFORMATION: synthetic

<400> SEQUENCE: 41

Arg Lys Lys Arg Arg Gln Arg Arg
1               5

<210> SEQ ID NO 42
<211> LENGTH: 11
<212> TYPE: PRT
<213> ORGANISM: Artificial
<220> FEATURE:
<223> OTHER INFORMATION: synthetic

<400> SEQUENCE: 42

Tyr Ala Arg Ala Ala Arg Gln Ala Arg Ala
1               5                   10

<210> SEQ ID NO 43
<211> LENGTH: 11
<212> TYPE: PRT
<213> ORGANISM: Artificial
<220> FEATURE:
<223> OTHER INFORMATION: synthetic

<400> SEQUENCE: 43

Thr His Arg Leu Pro Arg Arg Arg Arg Arg
1               5                   10

<210> SEQ ID NO 44
<211> LENGTH: 11
<212> TYPE: PRT
<213> ORGANISM: Artificial
<220> FEATURE:
<223> OTHER INFORMATION: synthetic

<400> SEQUENCE: 44

Gly Gly Arg Arg Ala Arg Arg Arg Arg Arg
1               5                   10

<210> SEQ ID NO 45
<211> LENGTH: 5
<212> TYPE: PRT
<213> ORGANISM: Artificial
<220> FEATURE:
```

```
<223> OTHER INFORMATION: synthetic

<400> SEQUENCE: 45

Gly Ser Gly Gly Ser
1               5

<210> SEQ ID NO 46
<211> LENGTH: 6
<212> TYPE: PRT
<213> ORGANISM: Artificial
<220> FEATURE:
<223> OTHER INFORMATION: synthetic

<400> SEQUENCE: 46

Gly Gly Ser Gly Gly Ser
1               5

<210> SEQ ID NO 47
<211> LENGTH: 4
<212> TYPE: PRT
<213> ORGANISM: Artificial
<220> FEATURE:
<223> OTHER INFORMATION: synthetic

<400> SEQUENCE: 47

Gly Gly Gly Ser
1

<210> SEQ ID NO 48
<211> LENGTH: 4
<212> TYPE: PRT
<213> ORGANISM: Artificial
<220> FEATURE:
<223> OTHER INFORMATION: synthetic

<400> SEQUENCE: 48

Gly Gly Ser Gly
1

<210> SEQ ID NO 49
<211> LENGTH: 5
<212> TYPE: PRT
<213> ORGANISM: Artificial
<220> FEATURE:
<223> OTHER INFORMATION: synthetic

<400> SEQUENCE: 49

Gly Gly Ser Gly Gly
1               5

<210> SEQ ID NO 50
<211> LENGTH: 5
<212> TYPE: PRT
<213> ORGANISM: Artificial
<220> FEATURE:
<223> OTHER INFORMATION: synthetic

<400> SEQUENCE: 50

Gly Ser Gly Ser Gly
1               5

<210> SEQ ID NO 51
<211> LENGTH: 5
<212> TYPE: PRT
<213> ORGANISM: Artificial
<220> FEATURE:
<223> OTHER INFORMATION: synthetic
```

```
<400> SEQUENCE: 51

Gly Ser Gly Gly Gly
1               5

<210> SEQ ID NO 52
<211> LENGTH: 5
<212> TYPE: PRT
<213> ORGANISM: Artificial
<220> FEATURE:
<223> OTHER INFORMATION: synthetic

<400> SEQUENCE: 52

Gly Gly Gly Ser Gly
1               5

<210> SEQ ID NO 53
<211> LENGTH: 5
<212> TYPE: PRT
<213> ORGANISM: Artificial
<220> FEATURE:
<223> OTHER INFORMATION: synthetic

<400> SEQUENCE: 53

Gly Ser Ser Ser Gly
1               5

<210> SEQ ID NO 54
<211> LENGTH: 7
<212> TYPE: PRT
<213> ORGANISM: Unknown
<220> FEATURE:
<223> OTHER INFORMATION: bacterial

<400> SEQUENCE: 54

Leu Gly Ile Asn Arg Gly Glu
1               5

<210> SEQ ID NO 55
<211> LENGTH: 7
<212> TYPE: PRT
<213> ORGANISM: Unknown
<220> FEATURE:
<223> OTHER INFORMATION: bacterial

<400> SEQUENCE: 55

Val Ala Ile Glu Asp Leu Ser
1               5

<210> SEQ ID NO 56
<211> LENGTH: 10
<212> TYPE: PRT
<213> ORGANISM: Unknown
<220> FEATURE:
<223> OTHER INFORMATION: bacterial

<400> SEQUENCE: 56

Pro Leu Asn Ala Asp Ala Asn Gly Ala Tyr
1               5                   10

<210> SEQ ID NO 57
<211> LENGTH: 7
<212> TYPE: PRT
<213> ORGANISM: Artificial
<220> FEATURE:
<223> OTHER INFORMATION: synthetic
```

<400> SEQUENCE: 57

Pro Lys Lys Arg Lys Val
1               5

<210> SEQ ID NO 58
<211> LENGTH: 16
<212> TYPE: PRT
<213> ORGANISM: Artificial
<220> FEATURE:
<223> OTHER INFORMATION: synthetic

<400> SEQUENCE: 58

Arg Gln Ile Lys Ile Trp Phe Gln Asn Arg Arg Met Lys Trp Lys Lys
1               5                   10                  15

<210> SEQ ID NO 59
<211> LENGTH: 1267
<212> TYPE: PRT
<213> ORGANISM: Unknown
<220> FEATURE:
<223> OTHER INFORMATION: bacterial

<400> SEQUENCE: 59

Met Ser Gln Leu Lys Arg Phe Thr Arg Leu Tyr Pro Leu Pro Lys Thr
1               5                   10                  15

Leu Arg Phe Glu Leu Lys Pro Ile Gly Lys Thr Leu Asp Phe Ile Lys
                20                  25                  30

Ser Ser Gly Leu Leu Glu Gln Asp Lys His Arg Ala Asp Ser Tyr Ile
        35                  40                  45

Arg Val Lys Lys Ile Ile Asp Glu Tyr His Lys Ala Phe Ile Glu Arg
    50                  55                  60

Val Leu Asp Lys Phe Glu Phe Gln Lys Asn Glu Gly Lys Lys Asn Ser
65                  70                  75                  80

Leu Glu Glu Phe Tyr Thr Cys Tyr Met Cys Lys Ser Lys Glu Asp Ala
                85                  90                  95

Gln Lys Asn Leu Phe Val Lys Ile Gln Asp Arg Leu Arg Lys Gln Leu
            100                 105                 110

Ala Asp Ser Phe Ala Lys Asp Lys Phe Lys Arg Ile Asp Lys Lys
        115                 120                 125

Glu Leu Ile Lys Glu Asp Leu Val Asn Phe Val Thr Ala Pro Glu Asp
    130                 135                 140

Arg Gln Leu Ile Asp Glu Phe Lys Asn Phe Thr Thr Tyr Phe Thr Gly
145                 150                 155                 160

Phe His Glu Asn Arg Lys Asn Met Tyr Ser Ala Glu Ala Gln Ser Thr
                165                 170                 175

Ala Ile Ala Tyr Arg Leu Ile His Glu Asn Leu Pro Lys Phe Ile Asp
            180                 185                 190

Asn Ile Leu Val Phe Asp Lys Val Ala Ile Ser Pro Val Ala Gly Cys
        195                 200                 205

Phe Thr Glu Leu Tyr Thr Asn Leu Glu Gln Tyr Leu Asn Val Asn Asp
    210                 215                 220

Leu Ser Glu Ile Phe Gln Leu Asp Tyr Tyr Asn Val Val Leu Thr Gln
225                 230                 235                 240

Lys Gln Ile Glu Ile Tyr Asn Lys Ile Ile Gly Gly Met Val Leu Asp
                245                 250                 255

Asp Gly Thr Lys Ile Lys Gly Leu Asn Glu Tyr Ile Asn Leu Tyr Asn
            260                 265                 270

-continued

```
Gln Gln Gln Lys Asp Lys Ser Ala Arg Leu Pro Lys Phe Lys Phe Leu
            275                 280                 285
Tyr Lys Gln Ile Leu Ser Asp Arg Asn Ile Ile Ser Trp Leu Pro Lys
290                 295                 300
Tyr Phe Gln Ser Asp Asn Glu Val Leu Glu Thr Ile Glu Gln Thr Tyr
305                 310                 315                 320
Gln Glu Leu Asp Lys Gln Val Phe Asn Arg Lys Asn Gly Gly Glu His
                325                 330                 335
Ser Leu Lys Glu Leu Leu Leu Thr Leu Ser Asp Tyr Asp Leu Asp Lys
            340                 345                 350
Ile Tyr Ile Arg Asn Asp Leu Gln Met Gly Asp Ile Ser Gln Lys Val
            355                 360                 365
Phe Gly His Trp Asn Val Ile Ser Lys Ala Leu Leu Glu Thr Leu Lys
370                 375                 380
Gln Glu Ile Pro Lys Lys Ser Lys Lys Glu Thr Glu Glu Ser Tyr Glu
385                 390                 395                 400
Asp Arg Leu Asn Lys Val Leu Lys Ser Gln Gly Ser Ile Ser Ile Ala
                405                 410                 415
Gln Ile Asn Lys Asn Val Gln Thr Trp Asn Ser Glu Asn Lys Asn Ser
            420                 425                 430
Ile Gln Ala Tyr Phe Ala Arg Leu Gly Thr Ile Glu Thr Asp Thr Ile
            435                 440                 445
Gln Lys Glu Asn Ile Phe Glu Gln Ile Ala Asn Ala Tyr Thr Glu Ala
        450                 455                 460
Lys Glu Leu Leu Asn Thr Pro Tyr Pro Ser Glu Lys Asn Leu Ala Gln
465                 470                 475                 480
Asp Lys Ile Asn Val Glu Lys Ile Lys Lys Leu Leu Asp Ser Ile Lys
                485                 490                 495
Ser Leu Gln Tyr Tyr Val Lys Pro Leu Leu Gly Asp Gly Ala Glu Pro
            500                 505                 510
Glu Lys Asp Glu Asn Phe Tyr Gly Glu Phe Ile Ala Leu Trp Glu Asp
        515                 520                 525
Leu Asn Lys Ile Thr Ser Leu Tyr Asn Met Val Arg Asn His Met Thr
530                 535                 540
Arg Lys Pro Tyr Ser Ile Glu Lys Ile Lys Leu Asn Phe Asp Asn Ser
545                 550                 555                 560
Thr Leu Met Asp Gly Trp Asp Leu Asn Lys Gln Ala Asn Thr Thr
                565                 570                 575
Val Ile Leu Arg Lys Asp Gly Leu Tyr Tyr Leu Ala Ile Met Asn Lys
            580                 585                 590
Lys Phe Asn Arg Val Phe Asp Val Lys Asn Met Pro Thr Asp Gly Glu
        595                 600                 605
Cys Tyr Glu Lys Met Glu Tyr Lys Gln Ile Ala Asp Ala Gly Lys Asp
    610                 615                 620
Ile Gln Asn Ile Ile Asn Cys Gly Gly Lys Tyr Lys Arg Phe Thr Lys
625                 630                 635                 640
Asn Leu Asp Arg Leu Lys Lys Glu Asn Ile Pro Tyr Ile Tyr Arg Ile
                645                 650                 655
Lys Glu Ser Gly Ser Tyr Leu Gln Asp Ser Lys Ser Glu Gly Asn
            660                 665                 670
Lys Phe Ser Lys Glu Asp Leu Asn Thr Phe Ile Glu Tyr Tyr Lys Asp
        675                 680                 685
```

-continued

Ala Ala Ile His Tyr Trp Asp Trp Cys Glu Phe Ser Phe Lys Lys Ser
690                 695                 700

Glu Asp Tyr Ala Asn Trp Lys Glu Phe Ile Asn His Val Lys Met Gln
705                 710                 715                 720

Gly Tyr Lys Ile Thr Phe Arg Asn Val Ser Ala Asp Tyr Ile His Ser
            725                 730                 735

Leu Val Glu Glu Gly Lys Ile Tyr Leu Phe Gln Ile Tyr Asn Lys Asp
                740                 745                 750

Phe Ser Pro His Ser Lys Gly Thr Pro Asn Leu His Thr Leu Tyr Trp
        755                 760                 765

Lys Met Leu Phe Asp Glu Arg Asn Leu Ala Asp Val Val Tyr Lys Leu
770                 775                 780

Asn Gly Gln Ala Glu Val Phe Phe Arg Lys Ser Ser Ile Ile His Glu
785                 790                 795                 800

Gln Pro Thr His Pro Ala Asn Leu Pro Ile Glu Asn Lys Asn Pro Leu
            805                 810                 815

Asn Lys Arg Ser Leu Ser Val Phe Ala Tyr Asp Ile Ile Lys Asp Lys
                820                 825                 830

Arg Tyr Thr Val Asp Lys Phe Gln Phe His Val Pro Ile Thr Met Asn
        835                 840                 845

Phe Lys Ser Thr Gly Lys Asp Asn Ile Asn Gln Ala Val Asn Lys Tyr
850                 855                 860

Ile Gln Lys Cys Asp Asp Leu His Ile Ile Gly Ile Asp Arg Gly Glu
865                 870                 875                 880

Arg His Leu Leu Tyr Leu Val Val Ile Asp Met Lys Gly Lys Ile Lys
            885                 890                 895

Glu Gln Tyr Ser Leu Asn Glu Ile Val Asn Thr Tyr Lys Gly Asn Glu
                900                 905                 910

Tyr His Thr Asp Tyr His Gly Leu Leu Ser Lys Arg Glu Asp Glu Arg
        915                 920                 925

Met Lys Ala Arg Gln Ser Trp Gln Thr Ile Asp Asn Ile Lys Tyr Leu
930                 935                 940

Lys Glu Gly Tyr Leu Ser Gln Val Val His Lys Ile Ser Glu Leu Ile
945                 950                 955                 960

Val Lys Tyr Asn Ala Ile Val Val Leu Glu Asp Leu Asn Glu Asp Phe
            965                 970                 975

Met Arg Gly Arg Gln Lys Val Glu Ala Ser Val Tyr Lys Lys Phe Glu
                980                 985                 990

Lys Met Leu Ile Asp Lys Leu Asn Tyr Leu Ala Asp Lys Asn Lys Lys
        995                 1000                1005

Phe Glu Glu Glu Gly Gly Ile Leu Asn Ala Tyr Gln Leu Thr Asn
    1010                1015                1020

Lys Phe Thr Ser Phe Lys Lys Met Asp Lys Gln Ser Gly Phe Leu
    1025                1030                1035

Phe Tyr Thr Gln Ala Trp Asn Thr Ser Lys Ile Asp Pro Val Thr
    1040                1045                1050

Gly Phe Val Asn Leu Phe Asp Thr Arg Tyr Glu Thr Leu Glu Lys
    1055                1060                1065

Ala Lys Ala Phe Phe Cys Lys Phe Asp Ser Ile Arg Tyr Asn Gly
    1070                1075                1080

Asp Lys Asp Trp Phe Glu Phe Ser Phe Asp Tyr Asn Asn Phe Thr
    1085                1090                1095

```
Thr Lys Ala Glu Gly Thr His Thr Gln Trp Thr Leu Cys Thr Cys
    1100                1105                1110

Gly Lys Arg Ile Glu Thr Phe Arg Asp Glu Lys Gln Asn Ser Arg
    1115                1120                1125

Trp Thr Ser Asn Glu Val Asp Leu Thr Asp Lys Phe Lys Val Phe
    1130                1135                1140

Phe Ala Asn Tyr Arg Ile Gly Ile Asn Gly Asn Leu Lys Glu Ser
    1145                1150                1155

Ile Val Lys Gln Gly Ala Ala Asp Phe Phe Arg Gly Leu Leu Tyr
    1160                1165                1170

Leu Leu Lys Leu Thr Leu Gln Met Arg Asn Ser Glu Ile Gly Ser
    1175                1180                1185

Glu Lys Asp Tyr Leu Gln Ser Pro Val Ala Asp Ala Asp Gly Lys
    1190                1195                1200

Phe Tyr Asn Ser Asp Leu Cys Asp Ala Thr Leu Pro Glu Asn Ala
    1205                1210                1215

Asp Ala Asn Gly Ala Tyr Asn Ile Ala Arg Lys Gly Leu Trp Met
    1220                1225                1230

Val Arg Lys Ile Lys Ala Ser Asp Asp Leu Asp Asn Leu Lys Leu
    1235                1240                1245

Ala Ile Gly Lys Lys Asp Trp Leu Gln Phe Ala Gln Asn Lys Pro
    1250                1255                1260

Tyr Leu Thr Asp
    1265
```

<210> SEQ ID NO 60
<211> LENGTH: 36
<212> TYPE: DNA
<213> ORGANISM: Unknown
<220> FEATURE:
<223> OTHER INFORMATION: bacterial

<400> SEQUENCE: 60
gtctataaga ctttaataat ttctactatt gtagat                                    36

<210> SEQ ID NO 61
<211> LENGTH: 82
<212> TYPE: RNA
<213> ORGANISM: Unknown
<220> FEATURE:
<223> OTHER INFORMATION: bacterial

<400> SEQUENCE: 61
auauguguaa uuaaaacuua augcguugau auauaauuuu uuuuacuuga uuggaugaug          60
aaccgggaua auuuauaauc aa                                                   82

<210> SEQ ID NO 62
<211> LENGTH: 19
<212> TYPE: DNA
<213> ORGANISM: Unknown
<220> FEATURE:
<223> OTHER INFORMATION: bacterial

<400> SEQUENCE: 62
aatttctact attgtagat                                                       19

<210> SEQ ID NO 63
<211> LENGTH: 7
<212> TYPE: PRT
<213> ORGANISM: Unknown

-continued

```
<220> FEATURE:
<223> OTHER INFORMATION: bacterial

<400> SEQUENCE: 63

Ile Gly Ile Asp Arg Gly Glu
1               5

<210> SEQ ID NO 64
<211> LENGTH: 7
<212> TYPE: PRT
<213> ORGANISM: Unknown
<220> FEATURE:
<223> OTHER INFORMATION: bacterial

<400> SEQUENCE: 64

Val Val Leu Glu Asp Leu Asn
1               5

<210> SEQ ID NO 65
<211> LENGTH: 10
<212> TYPE: PRT
<213> ORGANISM: Unknown
<220> FEATURE:
<223> OTHER INFORMATION: bacterial

<400> SEQUENCE: 65

Pro Glu Asn Ala Asp Ala Asn Gly Ala Tyr
1               5                   10

<210> SEQ ID NO 66
<211> LENGTH: 1229
<212> TYPE: PRT
<213> ORGANISM: Unknown
<220> FEATURE:
<223> OTHER INFORMATION: bacterial

<400> SEQUENCE: 66

Met Lys Asn Ile Phe His Asn Phe Thr His Cys Tyr Pro Val Ser Lys
1               5                   10                  15

Thr Leu Arg Phe Ser Leu Ile Pro Gln Gly Lys Thr Asp Glu Asn Ile
            20                  25                  30

Lys Lys Tyr Gly Phe Leu Asp Lys Asp Glu Val Lys Ala Lys Leu Tyr
        35                  40                  45

Pro Lys Val Lys Thr Ile Phe Asp Glu Tyr His Lys Ala Tyr Ile Glu
    50                  55                  60

Asp Met Leu Ser Thr Leu Val Cys Asp Phe Ser Glu Leu Phe Glu Val
65                  70                  75                  80

Phe Glu Lys Tyr Val Lys Asn Lys Gly Gln Thr Glu Lys Leu Tyr Glu
                85                  90                  95

Asp Thr Ala Asn Lys Tyr Gln Lys Ile Ser Asn His Leu Lys Asn
            100                 105                 110

Lys Glu Lys Ile Ser Glu Ile Val Pro Gln Lys Ile Ile Lys Asn Ala
        115                 120                 125

Val His Glu Ile Pro Arg Ile Pro Leu Ser Arg Glu Gln Ile Asp Ser
    130                 135                 140

Ile Ala Val Phe Asp Asn Phe Ala Thr Tyr Phe Glu Gly Tyr Arg Thr
145                 150                 155                 160

Val Arg Glu Asn Ile Tyr Ser Ala Asp Ile Ser Gly Ser Val Ala Tyr
                165                 170                 175

Arg Ile Val Arg Glu Asn Phe Pro Lys Phe Tyr Trp Asn Cys Gln Lys
            180                 185                 190
```

```
Tyr Arg Ala Leu Pro Asp Glu Leu Lys Arg Asp Phe Glu Val Glu Leu
            195                 200                 205

Ala Pro Leu Leu Cys Ser Val Pro Leu Asp Val Met Phe Ser Pro Glu
    210                 215                 220

Tyr Phe Gly His Thr Ile Thr Gln Gln Gly Ile Asp Ile Tyr Asn Thr
225                 230                 235                 240

Val Leu Gly Gly Ile Thr Glu Asn Glu Met Ser Lys Thr Lys Gly Leu
                245                 250                 255

Asn Glu Leu Cys Asn Leu Ala Phe Gln Gln Thr Gln Leu Asn Glu Arg
            260                 265                 270

Ile Lys Phe Ile Pro Leu Tyr Lys Gln Ile Leu Ser Asp Arg Glu Ser
            275                 280                 285

Ala Ser Phe Ile Pro Thr Pro Tyr Glu Asn Asp Ala Glu Val Lys Lys
            290                 295                 300

Asp Ile Ile Thr Leu Cys Asp Phe Ile Thr Glu Thr Asp Thr Val Ser
305                 310                 315                 320

Val Cys Ser Val Phe Gln Ser Glu Asn Val Cys Ala Glu Lys Ile Tyr
                325                 330                 335

Ile Asp Ser Lys Gln Leu Ser Val Leu Ser Gln Leu Leu Phe Val Gly
            340                 345                 350

Asp Trp Gly Tyr Ile Asn Lys Ala Ile Thr Ser Tyr Ala Ile Ser Ile
            355                 360                 365

Phe Gly Glu Lys Ala Asp Lys Lys Ile Glu Gln Tyr Thr Lys Lys Lys
    370                 375                 380

Ile Tyr Thr Leu Glu Glu Ile Ser Val Ser Leu Ala Asn Val Gly Tyr
385                 390                 395                 400

Lys Glu Ser Ile Leu Glu Lys Val Arg Gln Lys Phe Glu Ser Ser Tyr
                405                 410                 415

Thr Ser Phe Val Ala Leu Tyr Lys Ser Glu Gln Ser Ile Leu Ser Glu
            420                 425                 430

Glu Glu Gln Arg Ile Thr Thr Tyr Asp Gly Ile Lys Ala Leu Leu Asp
            435                 440                 445

Ser Ile Gln Glu Ile Glu Lys Thr Leu Lys Ile Phe His Ala Pro Asp
    450                 455                 460

Asp Ile Glu Lys Asp Gly Thr Phe Tyr Ser Val Phe Asp Glu Tyr
465                 470                 475                 480

Ala Arg Phe Arg Ser Asn Ile Thr Val Tyr Asn Lys Val Arg Asn Tyr
                485                 490                 495

Ala Thr Lys Lys Pro Tyr Ser Glu Glu Lys Phe Lys Leu Asn Phe Glu
            500                 505                 510

Ser Pro Thr Leu Ala Asp Gly Trp Asp Gln Asn Lys Gly Tyr Ala Asn
            515                 520                 525

Asn Thr Met Met Phe Asp Asn Asn Lys Tyr Tyr Ile Gly Ile Leu
    530                 535                 540

Asn Pro Lys Cys Lys Pro Lys Phe Thr Glu Glu Gln Phe Asp Ser Gly
545                 550                 555                 560

Asn Cys Tyr Lys Lys Met Val Tyr Lys Leu Leu Pro Gly Pro Asn Lys
                565                 570                 575

Met Leu Pro Lys Val Phe Leu Thr Ser Glu Thr Gly Lys Ser Thr Tyr
            580                 585                 590

Ser Pro Ser Glu Tyr Ile Leu Asp Gly Tyr Asn Ser Glu Lys His Lys
            595                 600                 605
```

```
Lys Gly Asp Asn Phe Asp Leu Gln Tyr Cys His Asp Leu Ile Asp Tyr
    610             615                 620

Phe Lys Asn Cys Ile Ser Arg His Pro Asp Trp Ser Lys Phe Asn Phe
625             630                 635                 640

Val Phe Ser Asp Thr Asn Thr Tyr Glu Asp Ile Ser Gly Phe Tyr Lys
            645                 650                 655

Glu Ile Asp His Gln Asn Tyr Lys Ile Thr Phe Ser Phe Val Ser Lys
            660                 665                 670

Asp Glu Leu His Ser Ala Val Asp Glu Gly Lys Leu Phe Leu Phe Glu
            675                 680                 685

Ile Tyr Asn Lys Asp Phe Ser Asp Ser Ser Thr Gly Arg Pro Asn Leu
690                 695                 700

His Thr Leu Tyr Phe Arg Glu Leu Phe Ser Asp Glu Asn Ile Lys Asp
705                 710                 715                 720

Pro Val Ile Lys Leu Asn Gly Gly Ala Glu Leu Phe Tyr Arg Pro Ala
            725                 730                 735

Ser Ile Pro Asn Pro Phe Val His Lys Lys Gly Ser Ile Leu Ile Asn
            740                 745                 750

Lys Arg Asp Thr Asp Gly Asn Val Val Asp Asn Ala Leu Tyr Leu Ser
            755                 760                 765

Ala Thr Lys Asp Ala Glu Gln Gly Met Ser Ile Glu Ala Leu Thr Ala
            770                 775                 780

Lys Tyr Pro Ser Leu Val Phe Arg Tyr Ala Pro His Asp Ile Thr Lys
785                 790                 795                 800

Asp Lys Arg Tyr Thr Lys Pro Ser Tyr Lys Phe His Val Pro Ile Thr
            805                 810                 815

Leu Asn Asn Thr Ser Asp Val Lys Tyr Pro Lys Phe Asn Thr Ala Val
            820                 825                 830

Leu Asn Ala Ile Glu Asn Asn Pro Asp Val Asn Ile Ile Gly Ile Asp
            835                 840                 845

Arg Gly Glu Arg Asn Leu Ile Tyr Val Ser Val Ile Asp Gln Ser Gly
            850                 855                 860

Lys Ile Leu Glu Gln Arg Ser Leu Asn Val Ile Gly Gly Ile Asp Tyr
865                 870                 875                 880

His Gln Lys Leu Ala Asn Ile Glu Lys Glu Arg Asp Asn Ala Arg Lys
            885                 890                 895

Asn Trp His Ala Ile Glu Asn Ile Lys Glu Thr Lys Glu Gly Tyr Leu
            900                 905                 910

Ser Leu Ala Val His Glu Ile Thr Ser Leu Met Leu Lys Tyr Asn Ala
            915                 920                 925

Ile Val Val Leu Glu Asp Leu Asn Phe Gly Phe Lys Arg Gly Arg Phe
            930                 935                 940

His Ile Glu Lys Gln Val Tyr Gln Lys Phe Glu Lys Met Leu Ile Asp
945                 950                 955                 960

Lys Leu Asn Tyr Leu Ala Asp Lys Ala Lys Thr Arg Glu Glu Gly Gly
            965                 970                 975

Ile Ser Asn Ala Tyr Gln Leu Thr Gly Lys Phe Glu Ser Phe Gln Lys
            980                 985                 990

Leu Gly Lys Gln Ser Gly Phe Leu Phe Tyr Val Pro Ala Arg Tyr Thr
995                 1000                1005

Ser Lys Ile Asp Pro Ala Ser Gly Phe Val Asn Leu Phe Thr Ser
    1010            1015                1020
```

Glu Gln Leu Lys Tyr Thr Ser Thr Pro Lys Ala Ile Asn Phe Val
    1025                1030                1035

Ser Asn Phe Ser Ser Ile Thr Tyr Cys Lys Glu His Asp Cys Phe
    1040                1045                1050

Ala Phe Glu Phe Val Tyr Ser Asp Phe Lys Leu Lys Ser Thr Asp
    1055                1060                1065

Phe Arg Asp Lys Trp Thr Val Tyr Thr Ala Gly Asn Gly Arg Val
    1070                1075                1080

Asn Val Lys Lys Glu Asn Gly Tyr Phe Cys Tyr Glu Arg Ile Glu
    1085                1090                1095

Val Thr Lys Glu Met Ser Ala Leu Phe Asp Lys Tyr Gly Ile Asp
    1100                1105                1110

Ile Thr Ala His Asp Ile Lys Pro Gln Ile Leu Lys Ile Asp Gln
    1115                1120                1125

Lys Glu Phe Trp Gln Lys Leu Leu Trp Leu Leu Arg Leu Thr Leu
    1130                1135                1140

Ser Leu Arg His Glu Asp Asp Arg Asp Asp Phe Ile Leu Ser Pro
    1145                1150                1155

Ile Cys Val Asn Gly Thr Phe Phe Asp Ser Arg Asn Phe Ser Asp
    1160                1165                1170

Val Ser Asn Ala Asp Met Pro Ile Asp Ala Asp Ala Asn Gly Ala
    1175                1180                1185

Tyr His Ile Ala Leu Gln Gly Leu Arg Met Leu Lys His Arg Ile
    1190                1195                1200

Ser Asp Gly Lys Ile Thr Ala Asp Glu Lys Asn Lys Gln Asn Tyr
    1205                1210                1215

Asn Trp Leu Lys Phe Val Gln Thr Arg Asn Asn
    1220                1225

<210> SEQ ID NO 67
<211> LENGTH: 36
<212> TYPE: DNA
<213> ORGANISM: Unknown
<220> FEATURE:
<223> OTHER INFORMATION: bacterial

<400> SEQUENCE: 67
gaataataat cccttataat ttctactatt gtagat                           36

<210> SEQ ID NO 68
<211> LENGTH: 67
<212> TYPE: RNA
<213> ORGANISM: Unknown
<220> FEATURE:
<223> OTHER INFORMATION: bacterial

<400> SEQUENCE: 68
augcuacaau gauuauuaua aagggagauua uuauuuuuaa aaaugcguuu uuuaugaauu    60
augcacc                                                              67

<210> SEQ ID NO 69
<211> LENGTH: 19
<212> TYPE: DNA
<213> ORGANISM: Unknown
<220> FEATURE:
<223> OTHER INFORMATION: bacterial -continued

```
<400> SEQUENCE: 69
aatttctact attgtagat                                                        19

<210> SEQ ID NO 70
<211> LENGTH: 7
<212> TYPE: PRT
<213> ORGANISM: Unknown
<220> FEATURE:
<223> OTHER INFORMATION: bacterial

<400> SEQUENCE: 70

Ile Gly Ile Asp Arg Gly Glu
1               5

<210> SEQ ID NO 71
<211> LENGTH: 7
<212> TYPE: PRT
<213> ORGANISM: Unknown
<220> FEATURE:
<223> OTHER INFORMATION: bacterial

<400> SEQUENCE: 71

Val Val Leu Glu Asp Leu Asn
1               5

<210> SEQ ID NO 72
<211> LENGTH: 10
<212> TYPE: PRT
<213> ORGANISM: Unknown
<220> FEATURE:
<223> OTHER INFORMATION: bacterial

<400> SEQUENCE: 72

Pro Ile Asp Ala Asp Ala Asn Gly Ala Tyr
1               5                   10

<210> SEQ ID NO 73
<211> LENGTH: 1219
<212> TYPE: PRT
<213> ORGANISM: Unknown
<220> FEATURE:
<223> OTHER INFORMATION: bacterial

<400> SEQUENCE: 73

Met Lys Lys Ile Asp Ser Phe Ile Asn Gln Tyr Asp Leu Ser Lys Thr
1               5                   10                  15

Leu Arg Phe Lys Leu Ile Pro Val Gly Glu Thr Glu Lys Asn Phe Ser
            20                  25                  30

Glu Glu Leu Leu Leu Ser Glu Asp Glu Arg Ala Lys Ala Tyr Val
        35                  40                  45

Cys Val Lys Lys Tyr Ile Asp Ala Tyr His Arg Asp Phe Ile Asp Lys
    50                  55                  60

Ala Leu Ser Gly Ile Lys Ser Leu Asp Ile Ser Lys Tyr Ala Glu Leu
65                  70                  75                  80

Tyr Tyr Lys Ser Glu Arg Asp Lys Asn Glu Ile Lys Lys Glu Ser Glu
                85                  90                  95

Asn Leu Arg Lys Gln Ile Ala Lys Ala Phe Thr Ser Arg Lys Glu Tyr
            100                 105                 110

Ser Gly Leu Phe Lys Lys Asp Val Ile Glu Ser Tyr Leu Pro Ala Phe
        115                 120                 125
```

```
Leu Ala Asp Glu Glu Ala Lys Glu Asn Val Gly Lys Phe Lys Lys Phe
        130                 135                 140

Ser Gly Tyr Phe Asn Glu Phe His Glu Asn Arg Lys Asn Ile Tyr Thr
145                 150                 155                 160

Ala Glu Glu Lys Ser Thr Gly Ile Ala Tyr Arg Cys Val Asn Asp Asn
                165                 170                 175

Leu Pro Lys Phe Leu Asn Asn Ile Lys Val Phe Glu Lys Val Arg Ala
            180                 185                 190

Glu Leu Pro Ala Glu Asn Val Asp Ala Leu Lys Ala Asp Phe Glu Gly
        195                 200                 205

Leu Ile Gly Phe Asp Ile Ala Glu Leu Phe Thr Tyr Asp Lys Phe Val
210                 215                 220

Tyr Val Leu Thr Gly Asp Gly Ile Arg Ala Tyr Asn Asn Val Ile Gly
225                 230                 235                 240

Gly Tyr Thr Ala Asp Thr Asp Val Lys Ile Lys Gly Leu Lys Gly Leu
                245                 250                 255

Asn Gln Tyr Ile Asn Leu Tyr Asn Gln Asn Lys Pro Lys Glu Lys Arg
            260                 265                 270

Leu Pro Phe Phe Lys Thr Leu Phe Lys Gln Ile Leu Ser Val Ser Glu
        275                 280                 285

Thr Ile Ser Phe Ile Pro Glu Lys Phe Ile Ser Asp Asp Glu Thr Leu
290                 295                 300

Ser Ala Ile Ser Ser Phe Tyr Asn Ala Ala Val Thr Asp Val Leu Asp
305                 310                 315                 320

Arg Val Thr Ser Val Phe Gly Gly Ile Glu Leu Phe Asp Ala Asp Lys
                325                 330                 335

Ile Tyr Tyr Lys Ser Asp Ser Val Ser Ser Leu Ser Asn Glu Leu Phe
            340                 345                 350

Gly Glu Trp His Ile Leu Lys Asp Ala Trp Arg Ala Glu Tyr Asp Arg
        355                 360                 365

Glu Tyr Lys Gly Lys Asn Lys Lys Pro Glu Lys Tyr Gln Glu Glu
370                 375                 380

Lys Asn Lys Ala Glu Lys Ala Lys Arg Tyr Phe Ser Leu Ser Glu Leu
385                 390                 395                 400

Ile Ser Tyr Ser Gly Glu Ala Gly Val Ile Gly Ser Phe Arg Glu Lys
                405                 410                 415

Ala Leu Glu Leu Thr Tyr Ala Val Lys Glu Lys Tyr Ala Ser Ala Arg
            420                 425                 430

Glu Leu Ile Glu Asn Glu Tyr Pro Lys Thr Ala Val Lys Leu Ile Lys
        435                 440                 445

Asn Gly Glu Ala Ile Phe Leu Ile Lys Glu Leu Leu Asp Ser Val Lys
450                 455                 460

Glu Leu Glu Arg Phe Ile Lys Pro Phe Ile Cys Glu Asp Asn Ser Val
465                 470                 475                 480

Asn Lys Asp Glu Ser Phe Tyr Ala Glu Leu Glu Thr Leu Ile Pro Phe
                485                 490                 495

Val Lys Asp Phe Ser Ala Leu Tyr Asp Lys Val Arg Asn Tyr Val Thr
            500                 505                 510

Gln Lys Pro Tyr Ser Thr Asp Lys Ile Lys Leu Asn Phe Arg Asn Pro
        515                 520                 525

Gln Phe Met Asn Gly Trp Asp Arg Asn Lys Glu Ser Asp Cys Ser Ala
530                 535                 540
```

```
Val Ile Leu Arg Asn Lys Asp Ser Phe Tyr Leu Ala Val Met Asp Asn
545                 550                 555                 560

Ser Thr Arg Ser Val Phe Lys Asn Tyr Pro Val Asp Gly Asp Asn Gly
                565                 570                 575

Trp Ser Lys Leu Glu Tyr Lys Leu Leu Pro Gly Pro Asn Lys Met Leu
            580                 585                 590

Pro Lys Val Phe Phe Ala Ala Ser Asn Ile Glu Phe Phe Ala Pro Ser
        595                 600                 605

Ala Glu Ile Met Glu Ile Tyr Glu Asn Gly Thr Phe Lys Lys Gly Asp
    610                 615                 620

Thr Phe Ser Ala Lys Asp Cys His Lys Leu Ile Gln Phe Tyr Gln Asp
625                 630                 635                 640

Ser Ile Ala Lys His Pro Asp Trp Ser Ala Phe Gly Phe Glu Phe Lys
                645                 650                 655

Asn Ala Glu Glu Tyr Ala Asp Ile Ser Glu Phe Tyr Arg Asp Val Glu
            660                 665                 670

Thr Gln Gly Tyr Lys Leu Gln Thr Lys Pro Ile Ser Glu Lys Tyr Ile
        675                 680                 685

Phe Asp Lys Val Ala Ser Gly Glu Leu Tyr Leu Phe Lys Ile Tyr Cys
    690                 695                 700

Lys Asp Phe Ser Glu Tyr Ser Lys Gly Lys Pro Asn Leu His Thr Leu
705                 710                 715                 720

Tyr Phe Lys Met Leu Phe Asp Glu Arg Asn Leu Glu Asp Thr Val Tyr
                725                 730                 735

Gln Leu Asn Gly Gly Ala Lys Leu Phe Tyr Arg Pro Pro Ser Leu Lys
            740                 745                 750

Leu Glu Glu Thr Ala Ile His Thr Ala Asn Glu Pro Ile Lys Asn Lys
        755                 760                 765

Asn Pro Lys Asn Lys Asn Glu Thr Ser Thr Phe Lys His Asp Leu Ile
770                 775                 780

Lys Asp Arg Arg Phe Thr Lys Pro His Phe Glu Leu His Leu Pro Ile
785                 790                 795                 800

Lys Leu Asn Phe Lys Ser Gln Asn Asn Ser Lys Ile Asn Val Lys Val
                805                 810                 815

Cys Glu Ala Leu Arg Glu Cys Glu Asn Asn Tyr Val Ile Gly Ile Asp
            820                 825                 830

Arg Gly Glu Arg Asn Leu Val Tyr Ile Thr Val Ile Asp Gly Ser Gly
        835                 840                 845

Lys Ile Ile Glu Gln Phe Ser Leu Asn Glu Ile Glu Thr Lys Ser Asn
850                 855                 860

Asp Thr Val His Val Thr Asp Tyr Arg Gly Leu Leu Asp Glu Lys Glu
865                 870                 875                 880

Asp Lys Leu Asn Ala Glu Arg Lys Ser Trp Gln Thr Val Glu Thr Ile
                885                 890                 895

Lys Glu Leu Lys Glu Gly Tyr Val Ser Gln Val Val His Lys Ile Cys
            900                 905                 910

Glu Leu Val Glu Lys Tyr Asp Ala Val Ile Ala Met Glu Asp Leu Asn
        915                 920                 925

Gly Gly Phe Lys Asn Ser Arg Ile Lys Val Glu Lys Gln Val Tyr Gln
930                 935                 940

Lys Leu Glu Lys Met Leu Ile Asp Lys Leu Asn Tyr Phe Ala Asp Lys
945                 950                 955                 960
```

```
Gly Lys Asp Ile Tyr Ala Pro Gly Gly Leu Leu Arg Ala Tyr Gln Leu
                965                 970                 975

Thr Glu Lys Phe Glu Ser Phe Glu Lys Met Thr Lys Gln Asn Gly Phe
                980                 985                 990

Ile Phe Tyr Val Pro Ala Trp Leu Thr Ser Lys Ile Asp Pro Val Thr
                995                1000                1005

Gly Phe Ala Asp Leu Leu Lys Pro Arg Tyr Val Ser Ile Asp Glu
           1010                1015                1020

Ser Ile Lys Phe Val Lys Lys Phe Asp Ser Ile Arg Trp Asn Ser
           1025                1030                1035

Lys Glu Asn Met Tyr Glu Phe Ser Phe Ala Tyr Ser Asn Phe Thr
           1040                1045                1050

Arg Gly Ser Ile Asp Ser Lys Lys Lys Trp Thr Val Tyr Thr Asn
           1055                1060                1065

Gly Asp Arg Ile Glu Arg Val Lys Gln Asp Asn Gly Arg Phe Asp
           1070                1075                1080

Gly Lys Tyr Val Asn Leu Thr Asp Glu Phe Lys Lys Leu Phe Lys
           1085                1090                1095

Lys Trp Gly Ile Asn Asp Asp Glu Asn Asp Met Ile Ser Ser Ile
           1100                1105                1110

Ala Ser Gln Lys Ser Lys Glu Phe Phe Ser Arg Phe Met Tyr Leu
           1115                1120                1125

Leu Lys Leu Thr Val Gln Met Arg Asn Ser Ile Ser Asn Ser Asp
           1130                1135                1140

Glu Asp Tyr Ile Ile Ser Pro Val Lys Asp Lys Asn Gly Asn Phe
           1145                1150                1155

Tyr Asp Ser Arg Asn Tyr Asn Ser Glu Ser Pro Leu Pro Ala Asp
           1160                1165                1170

Ala Asp Ala Asn Gly Ala Tyr Asn Ile Ala Arg Lys Ala Leu Trp
           1175                1180                1185

Ala Ile Asn Lys Ile Lys Asn Ala Lys Ala Gly Ser Tyr Glu Tyr
           1190                1195                1200

Pro Met Ile Ser Asn Lys Glu Trp Leu Glu Phe Ala Gln Asn His
           1205                1210                1215

Glu

<210> SEQ ID NO 74
<211> LENGTH: 36
<212> TYPE: DNA
<213> ORGANISM: Unknown
<220> FEATURE:
<223> OTHER INFORMATION: bacterial

<400> SEQUENCE: 74
gaattactaa ttgatataat ttctactgtt gtagat                                 36

<210> SEQ ID NO 75
<211> LENGTH: 67
<212> TYPE: RNA
<213> ORGANISM: Unknown
<220> FEATURE:
<223> OTHER INFORMATION: bacterial

<400> SEQUENCE: 75
gucuuaauuu caaaaaaauc ugucaauuag uaauuguaac gcuaaaaaau agaguaauuc        60
cacaaaa                                                                 67
```

<210> SEQ ID NO 76
<211> LENGTH: 19
<212> TYPE: DNA
<213> ORGANISM: Unknown
<220> FEATURE:
<223> OTHER INFORMATION: bacterial

<400> SEQUENCE: 76
aatttctact gttgtagat                                                    19

<210> SEQ ID NO 77
<211> LENGTH: 7
<212> TYPE: PRT
<213> ORGANISM: Unknown
<220> FEATURE:
<223> OTHER INFORMATION: bacterial

<400> SEQUENCE: 77

Ile Gly Ile Asp Arg Gly Glu
1               5

<210> SEQ ID NO 78
<211> LENGTH: 7
<212> TYPE: PRT
<213> ORGANISM: Unknown
<220> FEATURE:
<223> OTHER INFORMATION: bacterial

<400> SEQUENCE: 78

Ile Ala Met Glu Asp Leu Asn
1               5

<210> SEQ ID NO 79
<211> LENGTH: 10
<212> TYPE: PRT
<213> ORGANISM: Unknown
<220> FEATURE:
<223> OTHER INFORMATION: bacterial

<400> SEQUENCE: 79

Pro Ala Asp Ala Asp Ala Asn Gly Ala Tyr
1               5                   10

<210> SEQ ID NO 80
<211> LENGTH: 1214
<212> TYPE: PRT
<213> ORGANISM: Unknown
<220> FEATURE:
<223> OTHER INFORMATION: bacterial

<400> SEQUENCE: 80

Met Glu Glu Gln Asn Lys Phe Thr Asn Leu Tyr Ser Lys Ser Leu Thr
1               5                   10                  15

Leu Arg Phe Glu Ala Ile Pro Val Gly Lys Thr Glu Glu Asn Phe Arg
            20                  25                  30

Lys Lys Ile Leu Gln Lys Asp Met Asn Arg Ala Glu Lys Tyr Lys Glu
        35                  40                  45

Ala Lys Leu Ile Ile Asp Asn Tyr His Arg Trp His Ile Glu Thr Val
    50                  55                  60

Leu Lys His Thr Ser Leu Asp Glu Ser Lys Leu Val Lys Phe Tyr Glu
65                  70                  75                  80

Ile Tyr Ser Asp Lys Asn Tyr Glu Asn Arg Glu Asp Cys Leu Ser Ser
                85                  90                  95

```
Leu Gln Asn Glu Phe Arg Gly Val Ile Ser Lys Glu Leu Lys Asn Lys
            100                 105                 110

Lys Gly Leu Phe Gly Glu Asp Leu Ile Lys Ser Leu Ile Pro Gln Trp
            115                 120                 125

Leu Glu Leu Asn Gly Asp Lys Asp Ala Leu Ala Ile Ile Ser Glu Phe
            130                 135                 140

Asp Lys Phe Thr Thr Tyr Phe Lys Gly Phe Asn Thr Asn Arg Glu Asn
145                 150                 155                 160

Ile Tyr Thr Asp Lys Glu Lys Asn Ser Ile Thr Tyr Arg Leu Ile
                    165                 170                 175

His Glu Asn Leu Leu Lys Phe Ile Asp Asn Ile Asn Leu Phe Lys Gln
            180                 185                 190

Ile Ala Gln Thr Asp Val Ala Lys Asn Phe Asp Thr Val Thr Arg Asp
            195                 200                 205

Phe Gly Leu Asn Thr Ser Leu Gln Asp Ile Phe Thr Ile Thr Tyr Phe
            210                 215                 220

Asn Lys Leu Leu Thr Gln Thr Gly Ile Asp Arg Phe Asn Leu Ile Ile
225                 230                 235                 240

Gly Gly Leu Ser Thr Glu Lys Arg Thr Lys Ser Lys Gly Leu Asn Glu
            245                 250                 255

Tyr Ile Asn Glu Tyr Asn Gln Thr His Pro Gly Ser Gln Leu Pro Ile
            260                 265                 270

Phe Arg Pro Leu Phe Lys Gln Ile Leu Ser Glu Lys Lys Ser Leu Ser
            275                 280                 285

Tyr Leu Asp Ile Glu Phe Ser Asn Ser Ser Asp Val Ile Ala Ser Ile
            290                 295                 300

Arg Gln Ala Tyr Asp Thr Ile Asn Asn Leu Val Leu Pro Lys Ile Ser
305                 310                 315                 320

Asn Val Leu Gly Leu Ile Thr Ile Glu Arg Leu Pro Phe Ile Phe Ile
            325                 330                 335

Gln Asn Asp Thr Asp Val Thr Arg Ile Ser Asn Glu Leu Leu Gly Ser
            340                 345                 350

Phe Asp Tyr Ile Lys Arg Tyr Phe Val Ser Lys Tyr Glu Gln Val Ile
            355                 360                 365

Pro Cys Ser Lys Lys Glu Ser Arg Glu Lys Tyr Leu Glu Lys Ile Asn
            370                 375                 380

Lys Ala Trp Glu Lys Asn Lys Phe Leu Thr Leu Glu Tyr Ile Asn Thr
385                 390                 395                 400

Val Leu Cys Gln Asp Asn Lys Glu Asp Ile Ile Ser Tyr Phe Thr Gly
            405                 410                 415

Ala Arg Leu Ile Ser Tyr Ile Glu Ser Ile Arg Val Ala Tyr Asp Lys
            420                 425                 430

Cys Arg Asn Ile Leu Glu Asp Glu Tyr Asn Gly Glu Leu Lys Ser Asp
            435                 440                 445

Lys Glu Ser Thr Ser Ile Ile Lys Glu Leu Leu Asp Arg Ile Lys Asp
            450                 455                 460

Leu Gln Leu Phe Leu Lys Pro Leu Ser Lys Gly Glu Phe Gln Pro Gln
465                 470                 475                 480

Lys Ala Asp Asn Phe Tyr Asn Glu Phe Ile Pro Leu Tyr Ser Ile Leu
            485                 490                 495

Asp Asn Asn Ile Ser Arg Leu Tyr Asp Arg Val Arg Asn Tyr Val Thr
            500                 505                 510
```

```
Gln Lys Pro Tyr Ser Thr Asp Lys Val Lys Leu Asn Phe Glu Asn Ser
            515                 520                 525

Thr Leu Met Asn Gly Trp Asp Leu Asn Lys Glu Cys Ala Asn Thr Thr
        530                 535                 540

Ile Ile Leu Arg Lys Asp Asp Ala Tyr Tyr Ile Gly Ile Met Asp Lys
545                 550                 555                 560

Lys His Asn Lys Cys Phe Cys Gly Ala Ser Ile Pro Ala Glu Gly Glu
            565                 570                 575

Cys Tyr Glu Lys Met Asp Tyr Lys Leu Leu Pro Glu Pro Asn Lys Met
        580                 585                 590

Leu Pro Lys Val Phe Phe Ser Lys Ser Arg Ile Gly Glu Phe Thr Pro
        595                 600                 605

Ser Ser Glu Leu Leu Arg Asn Tyr Glu Arg Gly Thr His Lys Lys Gly
        610                 615                 620

Glu Asn Phe Arg Ile Glu Asp Cys Arg Asn Leu Ile Asp Phe Phe Lys
625                 630                 635                 640

Asn Ser Ile Asp Lys His Asn Asp Trp Lys Gln Phe Asn Phe Asn Phe
            645                 650                 655

Ser Ser Thr Asn Arg Tyr Arg Asn Leu Ser Glu Phe Tyr Arg Glu Val
            660                 665                 670

Glu Gln Gln Gly Tyr Lys Leu Thr Phe Arg Asn Ile Ser Val Ser Tyr
        675                 680                 685

Ile Asp Asn Leu Ile Lys Glu Gly Lys Leu Tyr Leu Phe Arg Leu His
        690                 695                 700

Asn Lys Asp Phe Ser Ser Tyr Ser Lys Gly Leu Pro Asn Leu His Thr
705                 710                 715                 720

Leu Tyr Trp Lys Met Leu Phe Asp Glu Asp Asn Leu Gln Asn Ile Val
            725                 730                 735

Tyr Lys Leu Asn Gly Lys Ala Glu Leu Phe Phe Arg Pro Ala Ser Ile
            740                 745                 750

Glu Gly Lys Ile Thr His Pro Ala Asn Val Pro Ile Ser Cys Lys Ser
        755                 760                 765

Glu Glu Asn Lys Gly Glu Asn Arg Thr Phe Lys Tyr Asn Leu Ile Lys
        770                 775                 780

Asp Lys Arg Tyr Thr Val Asp Lys Phe Gln Phe His Val Pro Ile Thr
785                 790                 795                 800

Leu Asn Phe Lys Glu Lys Gly Val Lys Asn Pro Asn Asp Phe Asn Glu
            805                 810                 815

Tyr Ile Asn Lys Tyr Tyr Leu Pro Gln Thr Thr His Ile Ile Gly Ile
            820                 825                 830

Asp Arg Gly Glu Arg His Leu Leu Tyr Ile Ser Val Ile Asp Met Asn
        835                 840                 845

Gly Asn Ile Val Lys Gln Phe Thr Leu Asn Glu Ile Ile Asn Glu Tyr
        850                 855                 860

Lys Gly Lys Ser Tyr Ser Thr Asp Tyr His Lys Lys Leu Glu Ile Arg
865                 870                 875                 880

Glu Asn Glu Arg Ala Lys Ala Arg Glu Ser Trp Gln Ser Ile Glu Asn
            885                 890                 895

Ile Lys Glu Leu Lys Glu Gly Tyr Leu Ser Gln Val Val His Lys Ile
        900                 905                 910

Val Gln Leu Val Leu Glu Tyr Asn Ala Val Ile Val Met Glu Asn Leu
        915                 920                 925
```

```
Glu Lys Gly Phe Lys Asn Asn Arg Leu Lys Ile Glu Lys Ser Val Tyr
    930                 935                 940

Gln Lys Phe Glu Asp Ala Leu Ile Asn Lys Leu Ser Tyr Ile Val Asp
945                 950                 955                 960

Lys Thr Lys Gly Lys Thr Asp Val Cys Gly Leu Leu Asn Ala Leu Gln
            965                 970                 975

Leu Ala Tyr Ile Pro Lys Thr Lys Ser Asp Ile Arg Asn Gln Cys Gly
            980                 985                 990

Ile Ile Phe Tyr Ile Pro Ala Trp Cys Thr Ser Lys Ile Asp Pro Val
        995                 1000                1005

Thr Gly Phe Val Ser Lys Ile Asn Thr Gln Tyr Thr Asn Lys Asp
    1010                1015                1020

Asn Ala Arg Asp Leu Ile Ser Lys Phe Ala Asp Ile Gln Tyr Asp
    1025                1030                1035

Lys Glu Asn Arg Tyr Phe Glu Phe Tyr Ile Asp Asp Tyr Ala Lys
    1040                1045                1050

Met Gly Gly Ile Glu Gly Thr Arg Lys Asn Trp Ile Leu Thr Ser
    1055                1060                1065

Arg Gly Ser Arg Ile Glu Thr Val Gln Asn Pro Val Thr Lys Lys
    1070                1075                1080

Tyr Ser Asn Gln Val Glu Val Asn Leu Thr Asp Glu Phe Met Thr
    1085                1090                1095

Ile Leu Lys Asp Gly Ile Asp Gly Asn Leu Lys Asp Tyr Ile Leu
    1100                1105                1110

Arg Gln Asp Asp Ser Gln Phe Phe Arg Asp Leu Leu Arg Cys Ile
    1115                1120                1125

Lys Leu Met Leu Gln Met Arg Asn Ser Lys Thr Gly Thr Asn Ile
    1130                1135                1140

Asp Tyr Leu Ile Ser Pro Val Lys Gln Glu Asp Gly Ala Phe Tyr
    1145                1150                1155

Asn Ser Asn Asp Arg Asn Pro Leu Leu Pro Ile Asp Ala Asp Ala
    1160                1165                1170

Asn Gly Ala Phe Asn Ile Ala Arg Lys Gly Leu Leu Val Ile Asn
    1175                1180                1185

Asn Ile Asn Asp Gly Lys Lys Asp Ala Phe Lys Ile Asp Asn Lys
    1190                1195                1200

Thr Trp Leu Asn Tyr Val Gln Gln Asn Asn Val
    1205                1210

<210> SEQ ID NO 81
<211> LENGTH: 36
<212> TYPE: DNA
<213> ORGANISM: Unknown
<220> FEATURE:
<223> OTHER INFORMATION: bacterial

<400> SEQUENCE: 81
gtctaataaa gacaaataat ttctactatt gtagat                              36

<210> SEQ ID NO 82
<211> LENGTH: 78
<212> TYPE: RNA
<213> ORGANISM: Unknown
<220> FEATURE:
<223> OTHER INFORMATION: bacterial
```

-continued

<400> SEQUENCE: 82
guugcuucaa uuuugugcgu ugagggauggg guaaauaacu uguuacugua aauuuaauau    60
uauaugguug uauugaau    78

<210> SEQ ID NO 83
<211> LENGTH: 19
<212> TYPE: DNA
<213> ORGANISM: Unknown
<220> FEATURE:
<223> OTHER INFORMATION: bacterial

<400> SEQUENCE: 83
aatttctact attgtagat    19

<210> SEQ ID NO 84
<211> LENGTH: 7
<212> TYPE: PRT
<213> ORGANISM: Unknown
<220> FEATURE:
<223> OTHER INFORMATION: bacterial

<400> SEQUENCE: 84

Ile Gly Ile Asp Arg Gly Glu
1               5

<210> SEQ ID NO 85
<211> LENGTH: 7
<212> TYPE: PRT
<213> ORGANISM: Unknown
<220> FEATURE:
<223> OTHER INFORMATION: bacterial

<400> SEQUENCE: 85

Ile Val Met Glu Asn Leu Glu
1               5

<210> SEQ ID NO 86
<211> LENGTH: 10
<212> TYPE: PRT
<213> ORGANISM: Unknown
<220> FEATURE:
<223> OTHER INFORMATION: bacterial

<400> SEQUENCE: 86

Pro Ile Asp Ala Asp Ala Asn Gly Ala Phe
1               5                   10

<210> SEQ ID NO 87
<211> LENGTH: 1229
<212> TYPE: PRT
<213> ORGANISM: Unknown
<220> FEATURE:
<223> OTHER INFORMATION: bacterial

<400> SEQUENCE: 87

Met Glu Lys Ile Ala Gln Phe Thr Asn Arg Tyr Gln Leu Ser Lys Thr
1               5                   10                  15

Leu Gln Phe Lys Leu Leu Pro Val Gly Lys Thr Gln Glu Asn Phe Asp
                20                  25                  30

Ser Lys Gln Leu Leu Ala Gln Asp Glu Glu Arg Ala Lys Thr Tyr Pro
            35                  40                  45

Leu Val Lys Gly Tyr Met Asp Arg Tyr His Lys Ala Phe Ile Asp Ser
        50                  55                  60

-continued

```
Val Leu Ser Thr Leu Leu Asn Asp Val Asp Lys Tyr Ser Glu Leu
65                  70                  75                  80

Tyr Tyr Lys Ser Asn Lys Thr Asn Thr Asp Asn Lys Asn Phe Glu Lys
                85                  90                  95

Leu Glu Glu Lys Leu Arg Lys Gln Ile Ser Asp Ala Leu Lys Gly Asp
            100                 105                 110

Leu Arg Tyr Lys Lys Met Phe Lys Lys Met Ile Thr Glu Leu Leu
            115                 120                 125

Pro Gly Phe Leu Asn Asp Asn Glu Glu Lys Leu Ile Ile Glu Gln Phe
            130                 135                 140

Ser Ser Phe Thr Thr Tyr Phe Ser Gly Phe Tyr Lys Asn Arg Glu Asn
145                 150                 155                 160

Met Tyr Ser Ser Asp Ala Lys Ser Thr Ala Ile Ser Tyr Arg Cys Ile
                165                 170                 175

Asn Asp Asn Leu Pro Lys Phe Leu Asp Asn Val Lys Ser Phe Glu Lys
            180                 185                 190

Val Lys Ser Ala Leu Ser Asn Glu Ile Glu Gln Leu Asn Thr Asp Phe
        195                 200                 205

Glu Gly Leu Leu Ser Val Lys Ala Glu Asp Ile Phe Asn Ala Asp Tyr
    210                 215                 220

Phe Ser Phe Val Leu Ser Gln Ser Gly Ile Gly Arg Tyr Asn Glu Val
225                 230                 235                 240

Ile Gly Gly Tyr Thr Phe Ser Asp Gly Arg Lys Ile Lys Gly Val Asn
                245                 250                 255

Glu Tyr Ile Asn Leu Tyr Asn Gln Thr Ala Asp Arg Thr Ser Arg Leu
            260                 265                 270

Pro Leu Met Lys Pro Leu Phe Lys Gln Ile Leu Ser Asp Ala Glu Ser
            275                 280                 285

Leu Ser Phe Ile Pro Glu Lys Phe Asn Ser Asp Lys Glu Val Leu Ala
    290                 295                 300

Ser Ile Asn Glu Tyr Tyr Ser Ile His Lys Ser Asp Ile Asp Asn Leu
305                 310                 315                 320

Arg Asn Leu Phe Ser Glu Leu Asn Gln Phe Asp Leu Thr Gly Ile Tyr
                325                 330                 335

Val Ser Gly Gly Ala Ser Ile Thr Asp Ile Ser Asn Ala Val Phe Gly
            340                 345                 350

Ser Trp Ser Ser Ile Ser Asp Gly Trp Lys Lys Ala Tyr Glu Glu Arg
            355                 360                 365

Ile Pro Leu Asn Asn Thr Arg Asn Ala Glu Lys Tyr Tyr Glu Lys Gln
            370                 375                 380

Ala Thr Ala Tyr Lys Ala Val Lys Ser Phe Ser Val Glu Glu Leu Gln
385                 390                 395                 400

Gln Tyr Gly Thr Pro Asp Glu Lys His Lys Gly Asn Ile Ser Glu Tyr
                405                 410                 415

Phe Ser Glu Thr Ile Ser Ile Leu Ala Ser Gln Ile Glu Gln Gln Tyr
            420                 425                 430

Glu Ala Ala His Thr Leu Leu Ser Glu Tyr Thr Asp Glu Lys Arg
            435                 440                 445

Leu Tyr Lys Asn Glu Arg Ala Ile Glu Leu Ile Lys Gly Leu Phe Asp
            450                 455                 460

Ser Ile Lys Thr Leu Glu Arg Val Ile Lys Pro Leu Leu Gly Thr Gly
465                 470                 475                 480
```

```
Lys Glu Glu His Lys Asp Asn Ile Phe Tyr Ser Lys Phe Leu Thr Tyr
                485                 490                 495

Tyr Glu Gly Leu Ser Ala Val Asp Lys Leu Tyr Asp Lys Val Arg Asn
            500                 505                 510

Tyr Met Thr Gln Lys Pro Tyr Ser Lys Asp Lys Ile Lys Leu Asn Phe
        515                 520                 525

Glu Asn Pro Gln Phe Met Gly Gly Trp Asp Arg Asn Lys Glu Lys Asp
    530                 535                 540

Tyr Arg Ala Val Leu Leu Lys Lys Gly Asn Asn Phe Tyr Leu Ala Val
545                 550                 555                 560

Met Asn Arg Gly Ser Asn Ser Val Phe Val Glu Phe Pro Tyr Ser Glu
                565                 570                 575

Gly Glu Ser Phe Tyr Glu Lys Ile Glu Tyr Lys Leu Leu Pro Gly Pro
            580                 585                 590

Asn Lys Met Leu Pro Lys Val Phe Phe Ala Ala Ser Asn Ile Asp Phe
        595                 600                 605

Phe Ala Pro Ser Glu Lys Ile Ile Gln Ile Tyr Arg Asn Glu Thr Phe
    610                 615                 620

Lys Lys Gly Ala Lys Phe Asn Ile Asp Asp Cys His Ala Leu Ile Asp
625                 630                 635                 640

Phe Tyr Lys Glu Ser Ile Glu Lys His Thr Asp Trp Ser Lys Phe Glu
                645                 650                 655

Phe Asn Phe Lys Pro Thr Asn Glu Tyr Ser Asp Ile Gly Ala Phe Tyr
            660                 665                 670

Asn Asp Val Lys Glu Gln Gly Tyr Ser Ile Lys Ala Lys Pro Val Ser
        675                 680                 685

Glu Ala Tyr Ile Asn Glu Leu Asn Glu Thr Gly Gln Ile Tyr Leu Phe
    690                 695                 700

Gln Ile Tyr Thr Lys Asp Phe Ser Glu Tyr Ser Lys Gly Thr Pro Asn
705                 710                 715                 720

Leu His Thr Met Tyr Phe Lys Met Leu Phe Asp Glu Arg Asn Leu Ser
                725                 730                 735

Asn Val Val Tyr Gln Leu Asn Gly Gly Ala Glu Met Phe Phe Arg Lys
            740                 745                 750

Ala Ser Ile Ser Glu Asn Glu Ile Ile Lys His Pro Ala Asn Ile Ala
        755                 760                 765

Val Lys Asn Lys Asn Pro Asp Asn Pro Lys Lys Glu Ser Leu Phe Glu
    770                 775                 780

Tyr Asp Leu Ile Lys Asp Arg Arg Phe Thr Lys His Gln Phe Ser Leu
785                 790                 795                 800

His Leu Pro Ile Thr Leu Asn Phe Lys Ala Asp Gly Asn Asn Met Leu
                805                 810                 815

Asn Tyr Asp Val Arg Lys Ala Leu Lys Asn Ser Asp Glu Asn Tyr Ile
            820                 825                 830

Ile Gly Ile Asp Arg Gly Glu Arg Asn Leu Leu Tyr Ile Cys Val Ile
        835                 840                 845

Asn Ser Asn Gly Glu Ile Val Glu Gln Leu Ser Leu Asn Glu Ile Ile
    850                 855                 860

Asn Gly Tyr Arg Asn Glu Lys Asp Glu Val Lys Leu Lys Thr Asp
865                 870                 875                 880

Tyr His Ser Leu Leu Leu Thr Lys Glu Lys Gln Arg Asp Glu Ala Arg
                885                 890                 895
```

```
Lys Asp Trp Thr Thr Ile Glu Asn Ile Lys Glu Leu Lys Glu Gly Tyr
                900                 905                 910

Leu Ser Gln Val Ile His Lys Ile Cys Gln Leu Val Lys Tyr Asp
            915                 920                 925

Ala Ile Ile Ala Met Glu Asp Leu Asn Ser Gly Phe Lys Asn Ser Arg
930                 935                 940

Val Lys Val Glu Arg Gln Val Tyr Gln Lys Phe Glu Lys Met Leu Ile
945                 950                 955                 960

Thr Lys Leu Gln Tyr Leu Val Asp Lys Lys Leu Pro Val Asp Glu Ala
            965                 970                 975

Gly Gly Val Leu His Ala Tyr Gln Leu Thr Asn Lys Glu Ser Ile Asn
            980                 985                 990

Gly Arg Gln Asn Gly Ile Ile Phe Tyr Val Pro Ala Trp Leu Thr Ser
            995                 1000                1005

Lys Ile Asp Pro Thr Thr Gly Phe Val Asp Leu Ile His Pro His
        1010                1015                1020

Tyr Gln Ser Val Asp Ala Ser Lys Met Leu Ile Ser Asn Phe Asp
        1025                1030                1035

Asn Ile Ser Tyr Asn Ser Lys Asp Asn Met Phe Glu Phe Glu Ile
        1040                1045                1050

Asp Tyr Ser Lys Phe Pro Lys Thr Ser Ala Ser Tyr Lys Thr Lys
        1055                1060                1065

Trp Thr Ile Cys Thr Asn Gly Glu Arg Ile Arg Ser Phe Arg Asn
        1070                1075                1080

Lys Ala Lys Asn Ser Glu Trp Asp Thr Glu Ile Val Val Leu Thr
        1085                1090                1095

Asp Glu Phe Lys Lys Leu Phe Glu Arg Tyr Asn Ile Asn Ile Ser
        1100                1105                1110

Asn Asn Met Lys Asn Glu Ile Leu Glu Lys Thr Glu Lys Glu Phe
        1115                1120                1125

Phe Glu Ser Phe Ile Arg Leu Phe Ala Leu Thr Leu Gln Met Arg
        1130                1135                1140

Asn Ser Ile Pro Asn Asn Thr Glu Ile Asp Tyr Leu Ile Ser Pro
        1145                1150                1155

Val Arg Ser Asn Asp Gly Lys Phe Tyr Asp Ser Arg Glu Tyr Glu
        1160                1165                1170

Lys Leu Glu Asn Pro Ala Leu Pro Ser Asn Ala Asp Ala Asn Gly
        1175                1180                1185

Ala Tyr Asn Ile Ala Arg Lys Ala Leu Trp Ala Ile Asp Val Leu
        1190                1195                1200

Lys Ala Thr Asp Glu Asn Glu Leu Ser Lys Thr Asn Leu Tyr Ile
        1205                1210                1215

Ala Asn Lys Asp Trp Leu Lys Met Val Gln Glu
        1220                1225

<210> SEQ ID NO 88
<211> LENGTH: 36
<212> TYPE: DNA
<213> ORGANISM: Unknown
<220> FEATURE:
<223> OTHER INFORMATION: bacterial

<400> SEQUENCE: 88
gtttaataat cccttttaat ttctactatt gtagat                          36
```

```
<210> SEQ ID NO 89
<211> LENGTH: 77
<212> TYPE: RNA
<213> ORGANISM: Unknown
<220> FEATURE:
<223> OTHER INFORMATION: bacterial

<400> SEQUENCE: 89
gugucuuaau augcuauaau uuauuuaagg gguuauuaag cggaugcaaa aguguacuuu      60
aacaccaauu uuugaau                                                    77

<210> SEQ ID NO 90
<211> LENGTH: 19
<212> TYPE: DNA
<213> ORGANISM: Unknown
<220> FEATURE:
<223> OTHER INFORMATION: bacterial

<400> SEQUENCE: 90
aatttctact attgtagat                                                  19

<210> SEQ ID NO 91
<211> LENGTH: 7
<212> TYPE: PRT
<213> ORGANISM: Unknown
<220> FEATURE:
<223> OTHER INFORMATION: bacterial

<400> SEQUENCE: 91

Ile Gly Ile Asp Arg Gly Glu
1               5

<210> SEQ ID NO 92
<211> LENGTH: 7
<212> TYPE: PRT
<213> ORGANISM: Unknown
<220> FEATURE:
<223> OTHER INFORMATION: bacterial

<400> SEQUENCE: 92

Ile Ala Met Glu Asp Leu Asn
1               5

<210> SEQ ID NO 93
<211> LENGTH: 10
<212> TYPE: PRT
<213> ORGANISM: Unknown
<220> FEATURE:
<223> OTHER INFORMATION: bacterial

<400> SEQUENCE: 93

Pro Ser Asn Ala Asp Ala Asn Gly Ala Tyr
1               5                   10

<210> SEQ ID NO 94
<211> LENGTH: 1242
<212> TYPE: PRT
<213> ORGANISM: Unknown
<220> FEATURE:
<223> OTHER INFORMATION: bacterial

<400> SEQUENCE: 94

Met Lys Lys Ile Asp Arg Phe Thr Asn Lys Tyr Ser Leu Ser Lys Thr
1               5                   10                  15
```

-continued

```
Leu Arg Phe Ser Leu Ile Pro Val Gly Lys Thr Glu Glu Asn Phe Asn
            20                  25                  30

Thr Arg Leu Leu Leu Asn Glu Asp Gln Lys Arg Ser Asp Ala Tyr Pro
        35                  40                  45

Val Val Lys Glu Leu Met Asp Arg Cys His Lys Glu Phe Ile Glu Lys
 50                  55                  60

Val Leu Ser Asp Leu Trp Leu Asp Gly Val Asp Val Tyr Ser Glu Leu
 65                  70                  75                  80

Tyr Asn Lys Ser Glu Ala Tyr Asp Glu Lys Ala Met Gly Lys Ala Glu
                85                  90                  95

Ser Asp Leu Lys Lys Arg Ile Ser Asp Ala Phe Thr Lys His Pro Gln
            100                 105                 110

Tyr Glu Arg Leu Leu Gly Lys Gly Ile Leu Glu Leu Ala Arg Glu Gln
            115                 120                 125

Ala Thr Asn Glu Glu Glu Cys Arg Ala Leu Asp Met Phe Glu Gly Phe
    130                 135                 140

Tyr Thr Tyr Phe Lys Gly Phe Glu Asp Asn Arg Lys Asn Met Tyr Lys
145                 150                 155                 160

Ala Asn Ile Lys Asn Ser Ile Ala Ser Arg Cys Ile Asp Asp Asn Leu
                165                 170                 175

Pro Lys Phe Leu Asp Asn Ser Lys Ile Phe Asn Thr Val Tyr Pro Leu
            180                 185                 190

Leu Val Gly Asp Thr Leu Ser Glu Leu Glu Glu Asn Val Lys Ser Leu
            195                 200                 205

Tyr Gly Ile Ser Leu Val Glu Val Phe Ser Ile Glu Ser Phe Ser Arg
    210                 215                 220

Phe Leu Ser Gln Asp Gly Ile Ala Leu Tyr Asn Thr Val Leu Gly Gly
225                 230                 235                 240

Tyr Thr Cys Ser Asp Thr Ser Lys Ala Gln Gly Leu Asn Glu Leu Ile
                245                 250                 255

Asn Lys Tyr Asn Gln Asp Ala Ala Gln Asn Asp Asn Gly Lys Lys Leu
            260                 265                 270

Pro Phe Leu Lys Pro Leu Tyr Asn Gln Ile Leu Gly Asp Lys Gln Thr
            275                 280                 285

Val Ser Phe Ile Pro Glu Lys Phe Gln Ser Asp Asn Glu Val Ile Leu
    290                 295                 300

Lys Ile Lys Glu Phe Cys Asp Thr Val Cys Ala Glu Thr Ile Glu Glu
305                 310                 315                 320

Ala Arg Glu Leu Phe Gly Glu Leu Ser Ala Phe Asp Pro Glu Lys Ile
                325                 330                 335

Tyr Val Ala Asn Asn Asp Asn Leu Thr Arg Leu Ser Lys Met Val Phe
            340                 345                 350

Gly Ser Trp Ser Ala Val Ser Ser Trp Tyr Ser Asp Tyr Val Ala
            355                 360                 365

Lys His Pro Lys Lys Glu Asn Glu Thr Val Asp Asp Tyr Glu Glu Lys
            370                 375                 380

Lys Arg Lys Ser Tyr Lys Lys Val Lys Cys Phe Ser Ile Ala Gln Leu
385                 390                 395                 400

Gln Arg Met Cys Ala Ala Pro Ser Glu Asp Glu Tyr Asp Gly Gly Val
                405                 410                 415

Ala Asp His Val Ser Lys Ala Val Gly Gln Cys Ala Glu Gly Tyr Tyr
            420                 425                 430
```

```
Lys Ala Leu Arg Glu Ala Glu Asp Leu Leu Asn Cys Asp Tyr Glu Gln
            435                 440                 445

Ser Asn Glu Lys Lys Leu Cys His Asn Asp Gly Ala Ile Thr Leu Leu
    450                 455                 460

Lys Asp Leu Leu Asp Ser Val Lys Glu Leu Glu Arg Ile Leu Ala Ile
465                 470                 475                 480

Phe Ala Asp Tyr Pro Lys Glu Met Asn Lys Asp Leu Phe Tyr Gly
                485                 490                 495

Arg Phe Asp Pro Ile Ile Ser Asn Val Arg Ala Ile Asp Arg Leu Tyr
                500                 505                 510

Asp Lys Val Arg Asn Tyr Val Thr Gln Lys Pro Tyr Ser Thr Asp Lys
            515                 520                 525

Ile Lys Leu Asn Phe Glu Asn Pro Gln Phe Met Gly Gly Trp Ala Thr
            530                 535                 540

Lys Leu Glu Leu Glu Arg Ser Ala Gln Leu Leu Lys Glu Pro Gly Asp
545                 550                 555                 560

Val Tyr Tyr Leu Ala Ile Ile Asp Lys Asp Ala Arg Ala Ile Leu Lys
                565                 570                 575

Asp Gly Tyr Asp Glu Pro Thr Cys Glu Glu Asp Val Leu Leu Lys Val
            580                 585                 590

Arg Tyr Glu Gln Met Ala Ser Pro Ala Lys Asp Ile Pro Asn Leu Met
            595                 600                 605

Phe Ile Asn Gly Glu Ala Lys Lys Val Asn Gly Lys Arg Asp Pro Asp
            610                 615                 620

Gly Lys Asn Arg Arg Leu Glu Gln Ala Lys Asn Asp Asn Leu Pro Pro
625                 630                 635                 640

Arg Val Asn Ala Ile Arg Leu Lys Tyr Gly Gly Tyr Gly Ile Asp Val
                645                 650                 655

Lys Lys Ala Glu Arg Ser Glu Val Thr Asp Phe Ile Asp Tyr Tyr Lys
                660                 665                 670

Arg Ala Val Glu Asp Tyr Tyr Ser Asn Phe Thr Phe Ser Leu Lys Asp
            675                 680                 685

Ala Ser Glu Tyr Asn Ser Phe Ser Glu Phe Thr Ser Asp Val Asp Ser
            690                 695                 700

Gln Ala Tyr Gln Ile Asn Phe Thr Lys Val Ser Lys Ala His Ile Asn
705                 710                 715                 720

Ser Leu Val Glu Lys Gly Met Ile Tyr Leu Phe Gln Ile Tyr Ser Lys
                725                 730                 735

Asp Phe Ser Lys Asn Lys Lys Pro Gly Thr Asp Asn Leu His Thr
                740                 745                 750

Met Tyr Phe Lys Met Leu Phe Asp Glu Lys Asn Leu Ser Asp Val Val
            755                 760                 765

Tyr Lys Leu Asp Gly Gly Ala Glu Met Phe Tyr Arg Tyr Ala Ser Leu
            770                 775                 780

Lys Lys Ser Glu Thr Thr Ile His Tyr Ala Arg Met Pro Ile Lys Asn
785                 790                 795                 800

Lys Asn Pro Asn Ser Val Lys Pro Ala Ser Thr Phe Glu Tyr Asp Leu
                805                 810                 815

Ile Lys Asn Asn Arg Phe Thr Lys Arg Gln Phe Ser Leu His Ile Pro
            820                 825                 830

Ile Thr Leu Asn Phe Lys Ala Glu Gly Asn Pro Tyr Ile Asn Asn Glu
            835                 840                 845
```

-continued

```
Val Arg Glu Ala Ile Lys Glu Cys Asp Glu Asn Tyr Val Ile Gly Ile
    850                 855                 860

Asp Arg Gly Glu Arg Asn Leu Leu Tyr Ile Ser Val Ile Asn Ser Arg
865                 870                 875                 880

Gly Glu Ile Val Val Gln Lys Ser Leu Asn Ser Val Gly Ala Thr Asp
                885                 890                 895

Tyr His Ser Ile Leu Lys Asn Arg Glu Asn Ala Arg Asp Glu Ala Arg
            900                 905                 910

Lys Ser Trp Gly Thr Ile Glu Asn Ile Lys Glu Leu Lys Asp Gly Tyr
        915                 920                 925

Leu Ser Gln Ala Ile His Glu Ile Ala Met Leu Ala Leu Glu Tyr Asp
    930                 935                 940

Ala Val Ile Ala Leu Glu Glu Leu Asn Tyr Gly Phe Lys Arg Gly Arg
945                 950                 955                 960

Phe Lys Val Glu Arg Gln Val Tyr Gln Lys Phe Glu Asn Met Leu Ile
                965                 970                 975

Thr Lys Leu Asn Tyr Leu Val Asp Lys Arg Lys Arg Pro Asp Glu Gln
            980                 985                 990

Gly Gly Leu Leu Lys Ala Tyr Gln Leu Thr Asn Lys Val Asp Gly Ile
        995                 1000                1005

Asn Lys Ser Leu Gln Asn Gly Ile Val Phe Tyr Val Pro Ala Tyr
    1010                1015                1020

Leu Thr Ser Lys Ile Asp Pro Ala Thr Gly Phe Val Asp Leu Ile
    1025                1030                1035

Lys Pro Lys Tyr Thr Ser Leu Ala Glu Ala Lys Ser Phe Ile Glu
    1040                1045                1050

Leu Leu Asp Gly Ile Arg Tyr Asp Arg Ile Glu Asn Leu Tyr Glu
    1055                1060                1065

Phe Asp Ile Asp Tyr Ser Lys Phe Pro Arg Asn Val Ser Tyr Lys
    1070                1075                1080

Ser Lys Trp Thr Leu Cys Ser Tyr Gly Glu Arg Ile Glu Thr Phe
    1085                1090                1095

Lys Ser Pro Glu Gly Asn Asn Lys Tyr Asp Asn Arg Arg Ile Val
    1100                1105                1110

Leu Thr Asp Glu Phe Asp Lys Leu Phe Glu Arg Tyr Ser Ile Asn
    1115                1120                1125

Lys Tyr Ala Asp Leu Lys Pro Gln Leu Leu Ala Ile Glu Asp Lys
    1130                1135                1140

Glu Phe Tyr Lys Arg Phe Met Lys Leu Met Gly Leu Met Leu Gln
    1145                1150                1155

Leu Arg Asn Ser Val Lys Gly Ser Val Asp Glu Asp Tyr Ile Ile
    1160                1165                1170

Ser Pro Val Arg Asp Lys Asp Gly Glu Phe Phe Asp Ser Arg Leu
    1175                1180                1185

Lys Lys Asp Arg Met Pro Glu Asn Ala Asp Ala Asn Gly Ala Tyr
    1190                1195                1200

Asn Ile Ala Arg Lys Ala Leu Trp Ala Ile Glu Gln Ile Lys Ala
    1205                1210                1215

Ala Asp Gly Glu Asp Ile Lys Lys Val Arg Leu Ser Ile Lys Asn
    1220                1225                1230

Ser Glu Trp Leu Glu Arg Ala Gln Lys
    1235                1240
```

<210> SEQ ID NO 95
<211> LENGTH: 36
<212> TYPE: DNA
<213> ORGANISM: Unknown
<220> FEATURE:
<223> OTHER INFORMATION: bacterial

<400> SEQUENCE: 95
gataaatgat ccctttaaat ttctactgtt gtagat                                  36

<210> SEQ ID NO 96
<211> LENGTH: 62
<212> TYPE: RNA
<213> ORGANISM: Unknown
<220> FEATURE:
<223> OTHER INFORMATION: bacterial

<400> SEQUENCE: 96
uuugauauau uauaaaugau aaagggauug uuuaagacuc ugccugcaaa aaaacacagc        60
aa                                                                       62

<210> SEQ ID NO 97
<211> LENGTH: 19
<212> TYPE: DNA
<213> ORGANISM: Unknown
<220> FEATURE:
<223> OTHER INFORMATION: bacterial

<400> SEQUENCE: 97
aatttctact gttgtagat                                                     19

<210> SEQ ID NO 98
<211> LENGTH: 7
<212> TYPE: PRT
<213> ORGANISM: Unknown
<220> FEATURE:
<223> OTHER INFORMATION: bacterial

<400> SEQUENCE: 98

Ile Gly Ile Asp Arg Gly Glu
1               5

<210> SEQ ID NO 99
<211> LENGTH: 7
<212> TYPE: PRT
<213> ORGANISM: Unknown
<220> FEATURE:
<223> OTHER INFORMATION: bacterial

<400> SEQUENCE: 99

Ile Ala Leu Glu Glu Leu Asn
1               5

<210> SEQ ID NO 100
<211> LENGTH: 10
<212> TYPE: PRT
<213> ORGANISM: Unknown
<220> FEATURE:
<223> OTHER INFORMATION: bacterial

<400> SEQUENCE: 100

Pro Glu Asn Ala Asp Ala Asn Gly Ala Tyr
1               5                   10

<210> SEQ ID NO 101

```
<211> LENGTH: 1212
<212> TYPE: PRT
<213> ORGANISM: Unknown
<220> FEATURE:
<223> OTHER INFORMATION: bacterial

<400> SEQUENCE: 101

Met Asp Lys Val Leu Asp Asn Tyr Ile Gly Leu Tyr Pro Val Ser Lys
1               5                   10                  15

Thr Leu Arg Phe Gly Leu Val Pro Met Tyr Glu Thr Glu Glu Asn Ile
            20                  25                  30

Val Lys Tyr Gly Ile Leu Asp Lys Asp Gly Leu Lys Ala Glu Lys Tyr
        35                  40                  45

Gln His Ala Lys Lys Val Phe Asp Lys Cys His Lys Ala Tyr Met Glu
    50                  55                  60

Met Ala Leu Gly Glu Met Lys Ser Asp Lys Trp Asn Asp Leu Tyr Gln
65                  70                  75                  80

Ile Leu Gln Glu Ser Gln Lys Glu Lys Ser Asp Asp Phe Ser Lys Ala
            85                  90                  95

Ala Asp Ile Met Arg Lys Glu Val Ser Lys Glu Leu Lys Lys His Lys
            100                 105                 110

Asp Phe Glu Gln Leu Asn Pro Lys Asn Ile Ile Asn Ala Ala Val Lys
        115                 120                 125

Asn Asp Thr Ala Leu Tyr Lys Phe Ser Thr Glu Arg Glu Tyr Val
    130                 135                 140

Ala Ser Phe Asp Lys Phe Ala Thr Tyr Phe Gln Gly Tyr Ser Glu Asn
145                 150                 155                 160

Arg Asn Asn Ile Tyr Ser Glu Glu Gln Gly Ser Ile Ala Tyr Arg Leu
            165                 170                 175

Ile Asn Glu Asn Phe Pro Lys Phe Ala Gly Asn Ile Lys Ile Phe Glu
            180                 185                 190

Gln Leu Pro Ala Asp Ile Lys Thr Glu Ala Gln Glu Ala Leu Gln Asp
        195                 200                 205

Leu Leu Asp Gly Tyr Ala Leu Glu Glu Val Phe Ser Pro Gln Phe Tyr
210                 215                 220

Asn Val Val Leu Thr Gln Ala Gly Val Asp Phe Tyr Asn Arg Leu Leu
225                 230                 235                 240

Gly Gly Phe Ser Ala Asp Asp Arg Asn Lys Val Gln Gly Phe Asn Glu
            245                 250                 255

Phe Leu Asn Leu Gly Tyr Gln Gln Asn Lys Leu Gly Lys Lys Leu Lys
        260                 265                 270

Phe Thr Leu Leu Tyr Lys Gln Ile Leu Ser Glu Lys Glu Gln Ile Ser
    275                 280                 285

Phe Ile Pro Gln Ala Leu Asp Asp Lys Ala Val Ile Asp Glu Ile
    290                 295                 300

Thr Ala Tyr Ser Glu Thr Leu Ile Ser Leu Ile Asp Glu Thr Lys Gly
305                 310                 315                 320

Glu Leu Gln Asp Ala Phe Phe Ser Ala Asp Thr Asn Leu Glu Lys Ile
            325                 330                 335

Tyr Val Asp Lys Lys Gln Thr Ala Leu Leu Ser Gln Leu Leu Phe Glu
        340                 345                 350

Asn Asp Trp Arg Val Leu Lys Asp Leu Leu Lys Glu Asn Asp Ile Lys
    355                 360                 365

Glu Gln Lys Val Tyr Ser Leu Ser Val Leu Gln Lys Ala Thr Asp Lys
370                 375                 380
```

-continued

```
Asn Ile Leu Asp Leu Leu Trp Asn Lys Phe Glu Glu Ser Ile Thr Val
385                 390                 395                 400

Leu Lys Asp Arg Tyr Ser Leu Phe Gln Gln Ile Ala Ala Gly Glu Lys
            405                 410                 415

Ile Asn Ser Phe Asp Glu Ile Lys Ile Tyr Leu Asp Ser Val Gln Ser
        420                 425                 430

Ala Glu Lys Leu Leu Lys Ile Leu Ala Ala Glu Asp Val Asp Lys
            435                 440                 445

Asp Ile Val Phe Tyr Pro Val Phe Asp Leu Val Tyr Gly Ala Leu Arg
        450                 455                 460

Ala Asn Val Ser Val Tyr Asn Met Val Arg Asn Tyr Ala Thr Lys Lys
465                 470                 475                 480

Pro Tyr Ser Thr Glu Lys Phe Lys Leu Asn Phe Glu Asn Pro Thr Leu
            485                 490                 495

Ala Glu Gly Trp Asp Gln Asn Lys Glu Tyr Ser Tyr Asn Thr Met Leu
        500                 505                 510

Phe Ile Lys Asp Gly Phe Tyr Tyr Leu Gly Val Leu Asn Ala Lys Asn
            515                 520                 525

Lys Pro Lys Ile Lys Glu Ser Leu Gln Pro Val Glu Asp Ala Tyr Gln
530                 535                 540

Lys Met Val Tyr Lys Leu Leu Pro Gly Pro Asn Lys Met Leu Pro Lys
545                 550                 555                 560

Val Phe Leu Ser Lys Lys Gly Leu Glu Thr Phe Gly Ala Asn Asp Tyr
            565                 570                 575

Ile Val Gly Gly Tyr Lys Ala Glu Lys His Lys Lys Gly Ser Asn Phe
        580                 585                 590

Asp Ile Glu Phe Cys His Asp Leu Val Asp Phe Phe Lys Asp Cys Ile
            595                 600                 605

Asp Arg His Glu Asp Trp Ser Lys Phe Gly Phe Glu Phe Ser Asp Thr
        610                 615                 620

Asp Ala Tyr Lys Asp Ile Ser Glu Phe Tyr Asn Glu Ile Ser Ala Gln
625                 630                 635                 640

Asn Tyr Thr Ile Lys Phe Ser Tyr Val Asp Thr Ala Gln Leu His Gln
            645                 650                 655

Leu Val Lys Asp Gly Lys Leu Phe Leu Phe Lys Ile Tyr Ser Lys Asp
        660                 665                 670

Phe Ser Glu Tyr Ser Lys Gly Lys Pro Asn Leu Gln Thr Leu Tyr Trp
            675                 680                 685

Lys Glu Ile Phe Ser Glu Glu Asn Leu Thr Lys Ala Ile Phe Lys Leu
            690                 695                 700

Asn Gly Gly Ala Glu Leu Phe Tyr Arg Pro Ala Ser Val Asp Asn Pro
705                 710                 715                 720

Phe Val His Glu Lys Gly Ser Ile Leu Ala Ser Lys Asn Asp Lys Asn
            725                 730                 735

Arg Gln Pro Val Ser Glu Glu Val Tyr Glu Thr Ile Thr Glu Leu Ile
            740                 745                 750

Asn Asn Gly Ala Ser Ile Asn Gln Leu Gln Ala Glu Tyr Pro Asp Ile
            755                 760                 765

Val Phe Lys Thr Ala Glu His Asp Ile Ile Lys Asp Lys Arg Tyr Ser
        770                 775                 780

Lys Ala Ser Tyr His Phe His Val Pro Val Thr Ile Asn Tyr Gly Arg
785                 790                 795                 800
```

```
Asp Asn Lys Ala Asn Asn Ile Asn Lys Met Val Leu Asp Asp Ile Gly
                805                 810                 815
Trp Asn Lys Asp Val Asn Ile Ile Gly Ile Asp Arg Gly Glu Arg Asn
        820                 825                 830
Leu Ile Tyr Val Ser Val Ile Asn Gln Asn Gly Asp Ile Leu Lys Gln
            835                 840                 845
Lys Gln Phe Asn Thr Ile Asp Asn Ser Val Ser Ser Val Asn Tyr His
850                 855                 860
Lys Lys Leu Asp Asn Leu Glu Lys Ser Arg Asp Ala Ala Arg Lys Asn
865                 870                 875                 880
Trp Lys Lys Ile Asn Asn Ile Lys Glu Met Lys Glu Gly Tyr Leu Ser
                885                 890                 895
Ser Val Val Lys Glu Ile Ala Asp Met Met Val Glu Tyr Asn Ala Ile
            900                 905                 910
Ile Ala Met Glu Asp Leu Asn Ala Gly Phe Lys Arg Gly Arg Phe His
        915                 920                 925
Ile Glu Lys Gln Val Tyr Gln Lys Phe Glu Lys Met Leu Ile Asp Lys
    930                 935                 940
Leu Asn Tyr Phe Ala Asp Lys Asn Val Ala Leu Glu Asp Asn Gly Ser
945                 950                 955                 960
Ile Arg His Gly Tyr Gln Leu Thr Ala Pro Phe Thr Ser Phe Gln Lys
                965                 970                 975
Leu Gly Lys Gln Ser Gly Phe Val Phe Tyr Val Pro Ala Ala Tyr Thr
            980                 985                 990
Ser Lys Ile Asp Pro Thr Thr Gly Phe Val Asn Leu Phe Thr Ser Lys
        995                 1000                1005
Gln Leu Ser Ser Gln Asn Ser Val Ala Gln Ser Lys Glu Phe Ile
    1010                1015                1020
Lys Ala Phe Arg Asn Ile Ser Phe Asp Ser Ser Phe Asn Cys Phe
    1025                1030                1035
Arg Phe Asp Phe Ser Tyr Ser Asp Phe Asp Val Phe Lys Lys Asp
    1040                1045                1050
Tyr Thr Asp Ser Trp Ser Val Tyr Thr Tyr Gly Asp Asp Arg Ile
    1055                1060                1065
Val His Ser Lys Lys Asn Gly Tyr Asp Thr His Glu Lys Ile Asn
    1070                1075                1080
Val Thr Glu Glu Leu Ile Ala Leu Phe Lys Glu Tyr His Ile Asp
    1085                1090                1095
Cys Ser Lys Glu Asn Leu Ile Asp Asp Ile Leu Ala Val Glu Gln
    1100                1105                1110
Ser Ala Phe Ile Lys Lys Phe Leu Trp Leu Phe Lys Ala Val Val
    1115                1120                1125
Gln Leu Arg Tyr Glu Asp Lys Glu Asn Asp Phe Ile Leu Ser Pro
    1130                1135                1140
Val Gln Lys Asp Gly Val Phe Phe Asp Ser Arg Lys Ala Asp Ser
    1145                1150                1155
Ser Met Pro Ala Asp Gly Asp Ala Asn Gly Ala Tyr His Ile Ala
    1160                1165                1170
Leu Gln Gly Leu Arg Ile Leu Lys Thr Lys Ile Lys Asn Gly Lys
    1175                1180                1185
Ile Ala Pro Asp Lys Lys Gly Glu Gln Ala Tyr Ser Trp Phe Glu
    1190                1195                1200
```

Phe Val Gln Lys Lys Ala Tyr Arg Lys
            1205                1210

<210> SEQ ID NO 102
<211> LENGTH: 36
<212> TYPE: DNA
<213> ORGANISM: Unknown
<220> FEATURE:
<223> OTHER INFORMATION: bacterial

<400> SEQUENCE: 102
atttaataat ccttataaat ttctactaat gtagat                                    36

<210> SEQ ID NO 103
<211> LENGTH: 58
<212> TYPE: RNA
<213> ORGANISM: Unknown
<220> FEATURE:
<223> OTHER INFORMATION: bacterial

<400> SEQUENCE: 103
auguguuacc auuaauauua auaaggauua uuaaauugag uuuuuuguc agcugcaa            58

<210> SEQ ID NO 104
<211> LENGTH: 19
<212> TYPE: DNA
<213> ORGANISM: Unknown
<220> FEATURE:
<223> OTHER INFORMATION: bacterial

<400> SEQUENCE: 104
aatttctact aatgtagat                                                       19

<210> SEQ ID NO 105
<211> LENGTH: 7
<212> TYPE: PRT
<213> ORGANISM: Unknown
<220> FEATURE:
<223> OTHER INFORMATION: bacterial

<400> SEQUENCE: 105

Ile Gly Ile Asp Arg Gly Glu
1               5

<210> SEQ ID NO 106
<211> LENGTH: 7
<212> TYPE: PRT
<213> ORGANISM: Unknown
<220> FEATURE:
<223> OTHER INFORMATION: bacterial

<400> SEQUENCE: 106

Ile Ala Met Glu Asp Leu Asn
1               5

<210> SEQ ID NO 107
<211> LENGTH: 10
<212> TYPE: PRT
<213> ORGANISM: Unknown
<220> FEATURE:
<223> OTHER INFORMATION: bacterial

<400> SEQUENCE: 107

Pro Ala Asp Gly Asp Ala Asn Gly Ala Tyr
1               5                   10

-continued

```
<210> SEQ ID NO 108
<211> LENGTH: 1214
<212> TYPE: PRT
<213> ORGANISM: Unknown
<220> FEATURE:
<223> OTHER INFORMATION: bacterial

<400> SEQUENCE: 108
```

| | | | | | | | | | | | | | | |
|---|---|---|---|---|---|---|---|---|---|---|---|---|---|---|
| Met | Met | Ser | Ser | Ile | Ile | Ser | Asn | Tyr | Thr | Gly | Val | Tyr | Pro | Val | Ser |
| 1 | | | | 5 | | | | | 10 | | | | | 15 | |

Lys Thr Leu Arg Phe Ser Leu Ile Pro Met Phe Glu Thr Glu Asp Asn
                20                  25                  30

Ile Lys Lys Tyr Gly Ile Val Asp Asn Asp Ser Ala Arg Ala Lys Lys
            35                  40                  45

Tyr Gln Gln Val Lys Arg Val Phe Asp Asn Tyr Tyr Lys Ala Tyr Leu
    50                  55                  60

Glu Tyr Ala Leu Gln Asn Ile Ala Val Lys Asn Trp Asp Ser Leu Tyr
65                  70                  75                  80

Asn Ile Leu Leu Glu Ser Gln Lys Asn Lys Thr Asp Asn Phe Arg Ile
                85                  90                  95

Glu Ala Glu Lys Val Ile Lys Asp Leu Ala Lys Ser Leu Thr Lys Asn
            100                 105                 110

Asp Arg Tyr Lys Leu Leu Ala Pro Lys Glu Ile Ile Asp Ala Ala Asn
    115                 120                 125

Lys Gly Asn Ser Ala Leu Tyr Ser Phe Thr Ala Glu Glu Arg Glu Thr
130                 135                 140

Val Cys Ala Phe Asp Lys Phe Ser Ser Tyr Phe Gln Gly Tyr Tyr Glu
145                 150                 155                 160

Asn Arg Asn Asn Ile Phe Gly Glu Lys Gln Gly Ser Val Ala Tyr Arg
                165                 170                 175

Ile Ile Ser Glu Asn Phe Pro Lys Phe Ala Gly Asn Ile Lys Ile Phe
            180                 185                 190

Lys Gln Leu Pro Glu Asp Val Ile Asp Tyr Ala Gln Glu Met Leu Gln
    195                 200                 205

Glu Leu Leu Gly Gly Asn Lys Leu Glu Thr Val Phe Glu Pro Glu Phe
210                 215                 220

Tyr Asn Asn Ile Leu Thr Gln Ser Gly Ile Glu Phe Tyr Asn Asn Leu
225                 230                 235                 240

Leu Gly Gly Val Ser Leu Asp Glu Arg Thr Arg Ile Gln Gly Phe Asn
                245                 250                 255

Glu Val Leu Asn Leu Tyr Gln Gln His Arg Ile Asp Lys Lys Ile
            260                 265                 270

Lys Phe Thr Leu Leu Phe Lys Gln Ile Leu Asn Asp Arg Glu Gln Leu
    275                 280                 285

Ser Phe Ile Pro Gln Ala Leu Leu Thr Asp Thr Ala Val Ile Ala Glu
290                 295                 300

Ile Ser Glu Tyr Lys Thr Val Ile Glu Glu Leu Glu Asn Ser Met
305                 310                 315                 320

Gln Glu Leu Lys Glu Thr Phe Phe Ser Asp Asp Ile Asp Thr Asp Lys
                325                 330                 335

Ile Tyr Val Asp Lys Lys Gln Ile Ser Val Leu Ser Gln Ile Leu Phe
            340                 345                 350

Glu Asn Gln Trp His Val Ile Ser Asp Leu Leu Lys Glu His Lys Ile
    355                 360                 365

```
Lys Glu Gln Lys Tyr Tyr Ser Leu Asn Thr Leu Gln Gln Phe Thr Asp
    370                 375                 380

Asn Asn Ile Leu Glu Met Val Trp Asn Lys Phe Ala Glu Ser Leu Glu
385                 390                 395                 400

Val Met Asn Gln Lys Ser Glu Ala Val Lys Asn Val Leu Leu Gln Glu
            405                 410                 415

Lys Ile Thr Gly Tyr Asp Glu Ile Lys Glu Tyr Leu Asp Ser Val Gln
            420                 425                 430

Ser Ser Glu Lys Val Leu Lys Ile Leu Ala Ile Gly Glu Glu Ala Asp
        435                 440                 445

Lys Asp Ser Val Phe Tyr Pro Val Phe Glu Leu Val Tyr Gly Ala Leu
    450                 455                 460

Arg Ala Asn Val Ser Val Tyr Asn Met Val Arg Asn Tyr Ala Thr Lys
465                 470                 475                 480

Lys Pro Tyr Ser Thr Glu Lys Tyr Lys Leu Asn Phe Glu Asn Pro Thr
                485                 490                 495

Leu Ala Asn Gly Trp Asp Gln Asn Lys Glu Tyr Ser Tyr Asn Thr Met
            500                 505                 510

Leu Phe Ile Lys Asp Asn Phe Tyr Leu Gly Val Leu Asn Ala Lys
            515                 520                 525

Asn Lys Pro Lys Ile Lys Glu Ser Gln Thr Pro Thr Glu Asn Ser Tyr
    530                 535                 540

Arg Lys Met Ile Tyr Lys Leu Leu Pro Gly Pro Asn Lys Met Leu Pro
545                 550                 555                 560

Lys Val Phe Phe Ser Lys Lys Gly Leu Glu Thr Phe Glu Val Ser Asp
                565                 570                 575

Tyr Ile Leu Asp Gly Tyr Asn Glu Gly Lys His Lys Lys Gly Asp Asn
            580                 585                 590

Phe Asp Ile Lys Phe Cys His Asp Leu Ile Asp Phe Phe Lys Glu Ser
        595                 600                 605

Ile Glu Lys His Glu Asp Trp Ser Lys Phe Gly Phe Glu Phe Ser Asp
    610                 615                 620

Thr Ser Thr Tyr Lys Asp Ile Gly Ala Phe Tyr Ser Glu Ile Ser Ala
625                 630                 635                 640

Gln Asn Tyr Lys Val Ser Phe Ser Tyr Val Asp Glu Glu Gln Met Gln
                645                 650                 655

Gln Leu Val Lys Asp Gly Lys Leu Phe Leu Phe Lys Leu Tyr Asn Lys
            660                 665                 670

Asp Phe Ser Glu Tyr Ser Lys Gly Lys Pro Asn Leu His Thr Met Tyr
            675                 680                 685

Trp Lys Glu Leu Phe Ser Glu Glu Asn Leu Lys Arg Ala Ile Phe Lys
    690                 695                 700

Leu Asn Gly Glu Ala Glu Leu Phe Tyr Arg Pro Ala Ser Ile Glu Asn
705                 710                 715                 720

Pro Phe Val His Lys Lys Gly Ser Val Leu Val Ser Lys Asn Asp Ile
                725                 730                 735

Asn Lys His Pro Val Asp Glu Ala Leu Tyr Glu Ala Ile Ile Glu Lys
            740                 745                 750

Ile Lys Ser Gly Ala Glu Ile Glu Gln Leu Lys Ala Glu Tyr Pro His
        755                 760                 765

Ile Val Phe Lys Thr Ala Glu Tyr Asp Ile Ile Lys Asp Lys Arg Tyr
    770                 775                 780
```

```
Ser Lys Ala Ser Tyr Ser Phe His Val Pro Leu Thr Ile Asn Tyr Gly
785                 790                 795                 800

Cys Ala Asp Gly Ser Asn Thr Ile Asn Lys Met Val Leu Asp Asp Ile
                805                 810                 815

Ser Trp Asn Lys Asp Ile Asn Ile Ile Gly Ile Asp Arg Gly Glu Arg
            820                 825                 830

Asn Leu Ile Tyr Val Ser Val Ile Asn Gln Lys Gly Glu Ile Leu Lys
        835                 840                 845

Gln Lys Ser Phe Asn Val Val Glu Asn Glu Val Ser Ser Val Asn Tyr
    850                 855                 860

His Lys Lys Leu Asp Asn Leu Glu Lys Ser Arg Asp Asp Ala Arg Lys
865                 870                 875                 880

Asn Trp Lys Asn Ile Asn Asn Ile Lys Glu Met Lys Glu Gly Tyr Leu
                885                 890                 895

Ser Ala Val Val Lys Glu Ile Ala Asp Met Met Val Glu Tyr Asn Ala
            900                 905                 910

Ile Val Ala Met Glu Glu Leu Asn Tyr Gly Phe Lys Arg Gly Arg Phe
        915                 920                 925

His Ile Glu Lys Gln Val Tyr Gln Lys Phe Glu Lys Met Leu Ile Asp
    930                 935                 940

Lys Leu Asn Tyr Leu Ala Asp Lys Asn Ile Pro Val Ala Glu Thr Gly
945                 950                 955                 960

Ser Ile Arg His Gly Tyr Gln Leu Ser Ala Arg Phe Thr Ser Phe Asn
                965                 970                 975

Asp Leu Thr Arg Phe Lys Gln Ser Gly Phe Ile Phe Tyr Val Pro Ala
            980                 985                 990

Ala Tyr Thr Ser Lys Ile Cys Pro Val Thr Gly Phe Val Asn Leu Phe
        995                 1000                1005

Thr Ser Lys Gln Thr Thr Tyr Gln Asn Met Ser Gln Ala Lys Glu
    1010                1015                1020

Phe Ile Tyr Ser Phe His Asn Ile Cys Tyr Asp Glu Glu Phe Asn
    1025                1030                1035

Cys Tyr Arg Phe Asp Phe Ser Tyr Ser Asp Phe Asp Ile Tyr Lys
    1040                1045                1050

Lys Asp Tyr Thr Asn Asp Trp Ser Val Tyr Ser Tyr Gly Lys Asp
    1055                1060                1065

Arg Ile Val His Thr Arg Ile Asn Gly Arg Asp Ser Ser Glu Lys
    1070                1075                1080

Ile Asp Val Thr Ala Arg Leu Thr Ala Leu Phe Glu Ser Asn Gly
    1085                1090                1095

Ile Asn Ile Lys Ala Asp Asn Leu Ile Asp Ser Ile Asn Ala Val
    1100                1105                1110

Asp Asn Ser Ala Phe Phe Lys Glu Leu Leu Trp Leu Phe Lys Ala
    1115                1120                1125

Val Val Gln Ile Arg Tyr Glu Asp Lys Asp Asn Asp Phe Ile Leu
    1130                1135                1140

Ser Pro Thr Asn Lys Asn Gly Val Phe Phe Asp Ser Arg Thr Ala
    1145                1150                1155

Gly Lys Asp Met Pro Val Asp Gly Asp Ala Asn Gly Ala Tyr His
    1160                1165                1170

Ile Ala Leu Gln Gly Leu Arg Leu Ile Lys Thr Arg Ile Lys Asp
    1175                1180                1185
```

Lys Lys Ile Leu Ser Asp Lys Ala Gly Glu Gln Ala Tyr Asn Trp
    1190                1195                1200

Phe Lys Phe Val Gln Glu Lys Asn Tyr Arg Gln
    1205                1210

<210> SEQ ID NO 109
<211> LENGTH: 36
<212> TYPE: DNA
<213> ORGANISM: Unknown
<220> FEATURE:
<223> OTHER INFORMATION: bacterial

<400> SEQUENCE: 109
atttaataat ccttataaat ttctactaat gtagat                        36

<210> SEQ ID NO 110
<211> LENGTH: 63
<212> TYPE: RNA
<213> ORGANISM: Unknown
<220> FEATURE:
<223> OTHER INFORMATION: bacterial

<400> SEQUENCE: 110
guaucauuau agugaauaag gauuauuaaa uuagcagauu uagugcauuu uaaauaauug  60
uaa                                                              63

<210> SEQ ID NO 111
<211> LENGTH: 19
<212> TYPE: DNA
<213> ORGANISM: Unknown
<220> FEATURE:
<223> OTHER INFORMATION: bacterial

<400> SEQUENCE: 111
aatttctact aatgtagat                                           19

<210> SEQ ID NO 112
<211> LENGTH: 7
<212> TYPE: PRT
<213> ORGANISM: Unknown
<220> FEATURE:
<223> OTHER INFORMATION: bacterial

<400> SEQUENCE: 112

Ile Gly Ile Asp Arg Gly Glu
1               5

<210> SEQ ID NO 113
<211> LENGTH: 7
<212> TYPE: PRT
<213> ORGANISM: Unknown
<220> FEATURE:
<223> OTHER INFORMATION: bacterial

<400> SEQUENCE: 113

Val Ala Met Glu Glu Leu Asn
1               5

<210> SEQ ID NO 114
<211> LENGTH: 10
<212> TYPE: PRT
<213> ORGANISM: Unknown
<220> FEATURE:
<223> OTHER INFORMATION: bacterial -continued

<400> SEQUENCE: 114

Pro Val Asp Gly Asp Ala Asn Gly Ala Tyr
1               5                  10

<210> SEQ ID NO 115
<211> LENGTH: 1175
<212> TYPE: PRT
<213> ORGANISM: Unknown
<220> FEATURE:
<223> OTHER INFORMATION: bacterial

<400> SEQUENCE: 115

Met Asn Lys Glu Lys Phe Thr Asn Arg Asp Ser Ile Val Lys Ser Leu
1               5                   10                  15

Ser Leu Glu Met Ile Pro Gln Gly Arg Thr Leu Glu Asn Ile Lys Glu
                20                  25                  30

Asn Gly Val Phe Glu Phe Glu Thr Asp Ile Ala Asp Ala Ala Glu Thr
            35                  40                  45

Leu Lys Gly Met Tyr Asp Gln Phe Tyr Arg Ala Leu Thr Val Glu Leu
    50                  55                  60

Met Glu Thr Ala Asp Ile Pro Val Glu Leu Tyr Gln Ala Tyr Ile
65                  70                  75                  80

Asn Arg Lys Glu Glu Lys Glu Val Tyr Glu Ala Leu Lys Asn Thr
                85                  90                  95

Phe Asp Glu Phe Thr Val His Val Lys Ala Tyr Ile Glu Tyr Asn Tyr
            100                 105                 110

Lys Lys Met Asn Arg Ile Val Asp Gly Thr Phe Phe Lys Glu Ile Phe
        115                 120                 125

Pro Ala Tyr Ala Lys Glu His Phe Thr Glu Glu Glu Leu Lys Val Tyr
    130                 135                 140

Glu Lys Cys Lys Glu Lys Val Thr Gly Ser Asp Val Tyr Phe Lys Ser
145                 150                 155                 160

Tyr Thr Glu Asn Arg Glu Lys Met Phe Gly Ser Ala Glu His Gly Thr
                165                 170                 175

Ile Ala Ala Arg Thr Ile Leu Glu Asn Leu Pro Val Tyr Phe Gly Asn
            180                 185                 190

Ala Leu Ile Trp Glu Ser Ile Lys Asn Lys Ile Asp Thr Ser Glu Tyr
        195                 200                 205

Asp Ile Asp Glu Ala Ile Phe Ala Leu Asp Asp Val Leu Thr Tyr Met
    210                 215                 220

Thr Tyr Glu Gly Ile Glu Ser Tyr Asn Lys Thr Leu Gly Val Leu Asn
225                 230                 235                 240

Gln Leu Ile Asn Glu His Asn Gln Lys His Asp Asp Asn Val Lys Ser
                245                 250                 255

Phe Arg Asn Lys Leu Lys Val Gln Ile Leu Thr Val Arg Ala Lys Asp
            260                 265                 270

Asn Ile Lys Thr Ile Thr Ser Asp Ala Glu Ala Ala Thr Leu Leu Lys
        275                 280                 285

Asp Asn Cys Glu His Leu Ala Asp Thr Glu Ile Val Asp Asn Val Ile
    290                 295                 300

Met Met Leu Leu Asp Thr Val Asn Asn Arg Glu Leu Ser Gln Ile Tyr
305                 310                 315                 320

Ile Gly Gly Asn Ser Leu Ser Tyr Ile Ser His Leu Leu Thr Ser Lys
                325                 330                 335

```
Gly Asp Ser Tyr Arg Glu Asn Phe Arg Glu Ser Gly Ile Ser Met Lys
                340                 345                 350

Ala Pro Tyr Tyr Ser Leu Glu Glu Leu Glu Glu Asn Tyr Pro Asp Ala
            355                 360                 365

Gly Ser Phe Ala Glu Ser Met Glu Arg Val Leu Tyr Asp Tyr Ala Gln
        370                 375                 380

Arg Tyr Lys Thr Ala Leu Ala Asn Ile Thr Lys Ser Leu Asn Lys Pro
385                 390                 395                 400

Glu Phe Tyr Leu Asn Ala Glu Val Glu Ala Val Gln Glu Phe Phe Asp
                405                 410                 415

Cys Ile Thr Glu Leu Arg Arg Phe Val Lys Arg Phe Ala Pro Asn Asp
            420                 425                 430

Met Glu Asp Leu Glu Tyr Asp Ala Val Phe Tyr Glu Asn Leu Tyr Ala
        435                 440                 445

Leu Ile Glu Asp Leu Asp Glu Val Ala Tyr Thr Gln Ser Leu Ile Lys
        450                 455                 460

Arg Tyr Ala Thr Lys Ala Pro Lys Asp Met Thr Lys Lys Val Arg Asn
465                 470                 475                 480

Cys Leu Gly Ser Pro Ser Ile Tyr Ser Asn Gly Trp Asn Leu Gln Asp
                485                 490                 495

Lys Asp Lys Lys Val Leu Ala Pro Gly Glu Gln Thr Leu Leu Val Lys
            500                 505                 510

Asp Gly Lys Tyr Tyr Leu Lys Pro Ala Thr Gly Gln Lys Ile Ile
        515                 520                 525

Phe Arg Asp Glu Pro Met Glu Asp Ala Tyr Glu Lys Ile Ser Val Met
        530                 535                 540

Gln Leu Val Asn Ala Tyr Gln Asn Leu Pro Lys Trp Ile Phe Ser Lys
545                 550                 555                 560

Asp Ile Lys Ala Lys Leu Glu Ala Gly Glu Glu Tyr Val Thr Arg Asn
                565                 570                 575

Asp Thr Val Glu Pro Phe Thr Val Thr Lys Asp Glu Tyr Asp Arg Tyr
            580                 585                 590

Lys Ala Gly Leu Phe Lys Lys Asp Pro Glu Glu Leu Thr Lys Trp Ile
        595                 600                 605

Asp Leu Cys Lys Lys Phe Ile Arg Val Asn Lys Asn Phe Ile Arg Phe
610                 615                 620

Glu Ile Asp Val Asp Lys Met Arg Pro Ser Asn Glu Tyr Thr Asn Ser
625                 630                 635                 640

Gly Glu Phe Tyr Asn Glu Val Asp Ala Met Thr Tyr Arg Leu Tyr Lys
                645                 650                 655

Gln Tyr Ile Ala Ala Glu Thr Leu Glu Asn Met Val Glu Glu Gly Asn
            660                 665                 670

Ala Tyr Leu Phe Met Leu Asn Gly Lys Asn Met Tyr Arg Asp His Cys
        675                 680                 685

Asn Asn Asp Tyr Ala Asn Ile Phe Met Tyr Ile Val Ser Glu Lys Asn
        690                 695                 700

Met Gln Ser Gly Leu Val Arg Leu Ala Ser Thr Thr Glu Ile Thr His
705                 710                 715                 720

Arg Lys Ser Cys Lys Glu Lys Lys Leu Thr His Lys Lys Gly Ser Tyr
                725                 730                 735

Leu Leu Asn Arg Tyr Thr Phe Thr Gly Glu Arg Ile Pro Glu His Ile
            740                 745                 750
```

```
Tyr Arg Glu Ile Tyr Asn Tyr His Asn Gly Leu Ser Thr Thr Ile Gly
        755                 760                 765

Ser Val Ala Gln Thr Tyr Met Asp Glu Asn Phe Val Glu Val Lys Lys
        770                 775                 780

Ala Asp Arg Asn Leu Ile Lys Asp Arg Arg Tyr Thr Glu Asp Lys Trp
785                 790                 795                 800

Phe Ile Ser Leu Cys Tyr Lys Leu Asn Pro Thr Pro Glu Arg Lys Asp
                805                 810                 815

Lys Leu Asn Asp Ala Val Arg Glu Glu Phe Asn Leu Asp Asn Pro Asn
                820                 825                 830

Val Leu Thr Ile Ile Arg Gly Glu Lys Asn Leu Leu Tyr Tyr Thr Leu
                835                 840                 845

Thr Gly Pro Asp Val Asn Glu Lys Gly Ser Leu Asn Val Met Asn Gly
        850                 855                 860

Ile Asn Tyr Ala Glu Leu Ile Ala Lys Tyr Gly Lys Glu Arg His Glu
865                 870                 875                 880

Thr Gln Lys Asp Trp Asn Tyr Thr Lys Lys Val Ala Asn Tyr Lys Asp
                885                 890                 895

Ser Tyr Ile Gly Gln Ala Val Ser Trp Ile Val Lys Lys Ala Leu Glu
        900                 905                 910

His Asn Ala Val Ile Cys Ile Glu Asp Ile Ser Lys Asn Phe Lys Glu
        915                 920                 925

Arg Asn Lys Cys Ile Asp Asn Gln Val Tyr Glu Lys Phe Glu Gly Met
        930                 935                 940

Leu Met Lys Arg Leu Ala Cys Phe Thr Asp Ser Lys Ile Pro Met Gly
945                 950                 955                 960

Glu Ile Gly Ser Leu Val Arg Pro Leu Gln Leu Ala Ser Glu Arg Leu
                965                 970                 975

Ser Met Ala Arg Gln Asn Gly Ile Leu Phe Lys Val Asn Asn Ala Arg
                980                 985                 990

Thr Ala Met Val Asp Glu Glu Asn Gly Phe Thr Ser Met Phe Ser Phe
        995                 1000                1005

Gly Asn Ile Thr Thr Val Ser Gly Met Lys Asn Phe Leu Ala Lys
        1010                1015                1020

Phe Lys Asp Ile Tyr Val Asp His Lys Gly Val His Ile Cys Phe
        1025                1030                1035

Asn Tyr Ala Asp Phe Gly Ala Ser Glu Leu Ala Ala Asp Cys Lys
        1040                1045                1050

Asp Met Asp Lys Asp Trp Lys Leu Ile Ile Thr Gly Lys Arg Asn
        1055                1060                1065

Met Lys Asn Ser Val Gly Ile Met Glu Val Val Asp Ile Glu Gln
        1070                1075                1080

Glu Trp Cys Ser Phe Leu Thr Gly Ile Lys Cys Glu Glu Gly Lys
        1085                1090                1095

Ser Leu Leu Glu Gln Ile Thr Ser Asp Ser Ala Leu Ser Arg Asn
        1100                1105                1110

Thr Phe Glu Leu Ile Lys Ala Ser Leu Met Ser Lys Tyr Thr Asp
        1115                1120                1125

Asp Asp Glu Met Tyr Ile Ser Pro Val Thr Gly Arg Thr Glu Gly
        1130                1135                1140

Tyr Ser Glu His Ala Ala Lys Met Leu Glu Arg Lys Leu Arg His
        1145                1150                1155
```

```
Phe Tyr Leu Asp Gly Arg Pro Tyr Thr Ala Glu Glu Trp Phe Gly
    1160                1165                1170

Ser Phe
    1175

<210> SEQ ID NO 116
<211> LENGTH: 36
<212> TYPE: DNA
<213> ORGANISM: Unknown
<220> FEATURE:
<223> OTHER INFORMATION: bacterial

<400> SEQUENCE: 116
tctcaaaaag atataagaat atctacttgc gtagat                                 36

<210> SEQ ID NO 117
<211> LENGTH: 69
<212> TYPE: RNA
<213> ORGANISM: Unknown
<220> FEATURE:
<223> OTHER INFORMATION: bacterial

<400> SEQUENCE: 117
auaaauacau ggcaggauuu auggaauauu ucaaggaaaa ugauccgauu uauuaccagg        60
cuuuaaaaa                                                               69

<210> SEQ ID NO 118
<211> LENGTH: 20
<212> TYPE: DNA
<213> ORGANISM: Unknown
<220> FEATURE:
<223> OTHER INFORMATION: bacterial

<400> SEQUENCE: 118
gaatatctac ttgcgtagat                                                   20

<210> SEQ ID NO 119
<211> LENGTH: 7
<212> TYPE: PRT
<213> ORGANISM: Unknown
<220> FEATURE:
<223> OTHER INFORMATION: bacterial

<400> SEQUENCE: 119

Leu Thr Ile Ile Arg Gly Glu
1               5

<210> SEQ ID NO 120
<211> LENGTH: 7
<212> TYPE: PRT
<213> ORGANISM: Unknown
<220> FEATURE:
<223> OTHER INFORMATION: bacterial

<400> SEQUENCE: 120

Ile Cys Ile Glu Asp Ile Ser
1               5

<210> SEQ ID NO 121
<211> LENGTH: 10
<212> TYPE: PRT
<213> ORGANISM: Unknown
<220> FEATURE:
<223> OTHER INFORMATION: bacterial
```

```
<400> SEQUENCE: 121

Pro Lys Asp Ala Asp Ala Asn Gly Ala Tyr
1               5                   10
```